US007524638B1

(12) United States Patent
Griffin et al.

(10) Patent No.: US 7,524,638 B1
(45) Date of Patent: Apr. 28, 2009

(54) METHODS FOR IDENTIFICATION OF MODULATORS OF OSGPR114 OR OSGPR78 ACTIVITY, AND THEIR USE IN THE TREATMENT OF DISEASE

(75) Inventors: Graeme Griffin, Centereach, NY (US); Lambertus J. Oehlen, Old Bethpage, NY (US)

(73) Assignee: OSI Pharmaceuticals, Inc., Melville, NY (US)

( * ) Notice: Subject to any disclaimer, the term of this patent is extended or adjusted under 35 U.S.C. 154(b) by 0 days.

(21) Appl. No.: 10/877,850

(22) Filed: Jun. 25, 2004

Related U.S. Application Data

(60) Provisional application No. 60/482,964, filed on Jun. 27, 2003.

(51) Int. Cl.
 *G01N 33/567* (2006.01)
 *C07K 14/705* (2006.01)
(52) U.S. Cl. .................................... 435/7.21; 436/501
(58) Field of Classification Search ....................... None
 See application file for complete search history.

(56) References Cited

U.S. PATENT DOCUMENTS

| | | | | |
|---|---|---|---|---|
| 6,210,967 | B1 * | 4/2001 | Bard .......................... | 435/361 |
| 6,344,342 | B1 * | 2/2002 | Tsui et al. ................. | 436/69.1 |
| 6,380,177 | B1 | 4/2002 | Erickson .................... | 514/141 |
| 2003/0027800 | A1 | 2/2003 | Miller et al. ............... | 514/102 |

FOREIGN PATENT DOCUMENTS

| | | |
|---|---|---|
| EP | 1090926 A1 | 4/2001 |
| EP | 1258484 A1 | 11/2002 |
| WO | WO 96/30406 | 10/1996 |
| WO | WO 00/23588 | 4/2000 |
| WO | WO 00/31258 | 6/2000 |
| WO | WO 00/50458 | 8/2000 |
| WO | WO 01/02563 | 1/2001 |
| WO | WO 01/04292 | 1/2001 |
| WO | WO 01/31014 | 5/2001 |
| WO | WO 01/42288 | 6/2001 |
| WO | WO 01/48189 | 7/2001 |
| WO | WO 01/77326 | 10/2001 |
| WO | WO 01/87937 | 11/2001 |
| WO | WO 01/90187 | 11/2001 |
| WO | WO 02/29001 | 4/2002 |

OTHER PUBLICATIONS

Rocheville, M., et al. Receptors for dopamine and somatostatin: formation of hetero-oligomers with enhanced functional activity. Science. Apr. 7, 2000;288(5463):154-7.
Gether, U. Uncovering molecular mechanisms involved in activation of G protein-coupled receptors. Endoer Rev. Feb. 2000;21(1):90-113.
Luttrell, L.M., et al. Beta-arrestin-dependent formation of beta2 adrenergic receptor-Src protein kinase complexes. Science. Jan. 29, 1999;283(5402):655-61.
Wise, A., et al. Target validation of G-protein coupled receptors. Drug Discov Today. Feb. 15, 2002;7(4):235-46.
Kaplan, M.H., et al. Identification of a G protein coupled receptor induced in activated T cells. J Immunol. Jul. 15, 1993;151(2):628-36.
Webb, T.E., et al. Identification of 6H1 as a P2Y purinoceptor: P2Y5. Biochem Biophys Res Commun. Feb. 6, 1996;219(1):105-10.
Li, Q., et al. The 6H1 orphan receptor, claimed to be the p2y5 receptor, does not mediate nucleotide-promoted second messenger responses. Biochem Biophys Res Commun. Jul. 18, 1997;236(2):455-60.
Toguchida, J., et al. Complete genomic sequence of the human retinoblastoma susceptibility gene. Genomics. Sep. 1993;17(3):535-43.
Herzog, H., et al. Intron 17 of the human retinoblastoma susceptibility gene encodes an actively transcribed G protein-coupled receptor gene. Genome Res. Sep. 1996;6(9):858-61.
White, et al. (2000) Nat. Genet. 26, 345-348.
Lee, D.K., et al. Discovery and mapping of ten novel G protein-coupled receptor genes. Gene. Sep. 5, 2001;275(1):83-91.
Chun, J., et al. International Union of Pharmacology. XXXIV. Lysophospholipid receptor nomenclature. Pharmacol Rev. Jun. 2002;54(2):265-9.
Xu, Y., et al. Characterization of an ovarian cancer activating factor in ascites from ovarian cancer patients. Clin Cancer Res. Oct. 1995;1(10):1223-32.
Tanyi, J.L., et al. The human lipid phosphate phosphatase-3 decreases the growth, survival, and tumorigenesis of ovarian cancer cells: validation of the lysophosphatidic acid signaling cascade as a target for therapy in ovarian cancer. Cancer Res. Mar. 1, 2003;63(5):1073-82.
Fang, X., et al. Lysophospholipid growth factors in the initiation, progression, metastases, and management of ovarian cancer. Ann NY Acad Sci. Apr. 2000;905:188-208.
Fujita, T., et al. Expression of lysophosphatidic acid receptors and vascular endothelial growth factor mediating lysophosphatidic acid in the development of human ovarian cancer. Cancer Lett. Mar. 31, 2003;192(2):161-9.
Erickson, J.R., et al. Lysophosphatidic acid and ovarian cancer: a paradigm for tumorogenesis and patient management. Prostaglandins Other Lipid Mediat. Apr. 2001;64(1-4):63-81.
Daaka, Y. Mitogenic action of LPA in prostate. Biochim Biophys Acta. May 23, 2002;1582(1-3):265-9.
Fukushima, N., et al. Lysophospholipid receptors. Annu Rev Pharmacol Toxicol. 2001;41:507-34.
Noguchi et al. (2003) J. Biol. Chem. Apr. 30, electronic manuscript M302648200 ahead of print.

(Continued)

*Primary Examiner*—John D Ulm
(74) *Attorney, Agent, or Firm*—Alexander A. Stewart; OSI Pharmaceuticals, Inc

(57) ABSTRACT

This invention relates to the identification of LPA as a ligand for the G-protein coupled receptors OSGPR114 and OSGPR78. The invention is directed to new methods for screening candidate drugs for their ability to modulate the activity of OSGPR114 or OSGPR78, and new pharmaceutical agents identified by these methods. It is also directed to the use of such agents in the manufacture of medicaments for the treatment of OSGPR114 or OSGPR78 mediated diseases, and methods of treating diseases such as cancers by administering to an individual a therapeutic amount of a modulator of OSGPR114 or OSGPR78 identified by these methods.

36 Claims, 27 Drawing Sheets

OTHER PUBLICATIONS

Wu, J., et al. Trans-regulation of epidermal growth factor receptor by lysophosphatidic acid and G protein-coupled receptors. Biochem Biophys Acta. May 23, 2002;1582(1-3):100-6.

Fischer, D.J., et al., Short-chain phosphatidates are subtype-selective antagonists of lysophosphatidic acid receptors. Mol Pharmacol. Oct. 2001;60(4):776-84.

Hasegawa, Y., et al. Identification of a phosphothionate analogue of lysophosphatidic acid (LPA) as a selective agonist of the LPA3 receptor. J Biol Chem. Apr. 4, 2003;278(14):11962-9. Epub Jan. 27, 2003.

Heise, C.E., et al., Activity of 2-substituted lysophosphatidic acid (LPA) analogs at LPA receptors: discovery of a LPA1/LPA3 receptor antagonist. Mol Pharmacol. Dec. 2001;60(6):1173-80.

Hooks, S.B., et al. Lysophosphatidic acid-induced mitogenesis is regulated by lipid phosphate phosphatases and is Edg-receptor independent. J Biol Chem. Feb. 16, 2001;276(7):4611-21. Epub Oct. 19, 2000.

Hopper, D.W., et al. Structure—activity relationships of lysophosphatidic acid: conformationally restricted backbone mimetics. J Med Chem. Mar. 25, 1999;42(6):963-70.

Tigyi, G. Selective ligands for lysophosphatidic acid receptor subtypes: gaining control over the endothelial differentiation gene family. Mol Pharmacol. Dec. 2001;60(6):1161-4.

Yokoyama, K., et al. Stereochemical properties of lysophosphatidic acid receptor activation and metabolism. Biochim Biophys Acta. May 23, 2002;1582(1-3):295-308.

Gueguen, G., et al. Structure-activity analysis of the effects of lysophosphatidic acid on platelet aggregation. Biochemistry. Jun. 29, 1999;38(26):8440-50.

Lynch, K.R., et al. Structure-activity relationships of lysophosphatidic acid analogs. Biochim Biophys Acta. May 23, 2002;1582(1-3):289-94.

Sardar, V.M., et al. Molecular basis for lysophosphatidic acid receptor antagonist selectivity. Biochim Biophys Acta. May 23, 2002;1582(1-3):309-17.

Virag, T., et al. Fatty alcohol phosphates are subtype-selective agonists and antagonists of lysophosphatidic acid receptors. Mol Pharmacol. May 2003;63(5):1032-42.

Ye, X., et al. Lysophosphatidic acid as a novel cell survival/apoptotic factor. Biochim Biophys Acta. Dec. 30, 2002;1585(2-3):108-13.

GenBank Accession No. AJ272207.

GenBank Accession No. AF000546.

GenBank Accession No. AY255621.

GenBank Accession No. NM_175116.

Janssens, R., et al. Cloning of human heptahelical receptor closely related to the P2Y5 receptor. Biochem Biophys Res Commun. Jul. 9, 1997;236(1):106-12.

Mills, G.B., et al. The emerging role of lysophosphatidic acid in cancer. Nat Rev Cancer. Aug. 2003;3(8):582-91.

Marte, B.M., et al., PKB/Akt: connecting phosphoinositide 3-kinase to cell survival and beyond. Trends Biochem Sci. Sep. 1997;22(9):355-8.

* cited by examiner

Figure 1A.

OSGPR78

ATGGTAAGCGTTAACAGCTCCCACTGCTTCTATAATGACTCCTTTAAGTAC
ACTTTGTATGGGTGCATGTTCAGCATGGTGTTTGTGCTTGGGTTAGTATCC
AATTGTGTTGCCATATACATTTTCATCTGCGTCCTCAAAGTCCGAAATGAA
ACTACAACTTACATGATTAACTTGGCAATGTCAGACTTGCTTTTGTTTTA
CTTTACCCTTCAGGATTTTTTACTTCACAACACGGAATTGGCCATTTGGAG
ATTTACTTTGTAAGATTTCTGTGATGCTGTTTTATACCAACATGTACGGAA
GCATTCTGTTCTTAACCTGTATTAGTGTAGATCGATTTCTGGCAATTGTCTA
CCCATTTAAGTCAAAGACTCTAAGAACCAAAAGAAATGCAAAGATTGTTT
GCACTGGCGTGTGGTTAACTGTGATCGGAGGAAGTGCACCCGCCGTTTTT
GTTCAGTCTACCCACTCTCAGGGTAACAATGCCTCAGAAGCCTGCTTTGAA
AATTTTCCAGAAGCCACATGGAAAACATATCTCTCAAGGATTGTAATTTTC
ATCGAAATAGTGGGATTTTTTATTCCTCTAATTTTAAATGTAACTTGTTCTA
GTATGGTGCTAAAAACTTTAACCAAACCAGTTACATTAAGTAGAAGCAAA
ATAAACAAAACTAAGGTTTTAAAAATGATTTTTGTACATTTGATCATATTC
TGTTTCTGTTTTGTTCCTTACAATATCAATCTTATTTTATATTCTCTTGTGAG
AACACAAACATTTGTTAATTGCTCAGTAGTGGCAGCAGTAAGGACAATGT
ACCCAATCACTCTCTGTATTGCTGTTCCAACTGTTGTTTTGACCCTATAGT
TTACTACTTTACATCGGACACAATTCAGAATTCAATAAAAATGAAAAACT
GGTCTGTCAGGAGAAGTGACTTCAGATTCTCTGAAGTTCATGGTGCAGAG
AATTTTATTCAGCATAACCTACAGACCTTAAAAAGTAAGATATTTGACAAT
GAATCTGCTGCCTGA

Figure 1B.

OSGPR114

ATGTTAGCCAACAGCTCCTCAACCAACAGTTCTGTTCTCCCGTGTCCTGAC
TACCGACCTACCCACCGCCTGCACTTGGTGGTCTACAGCTTGGTGCTGGCT
GCCGGGCTCCCCCTCAACGCGCTAGCCCTCTGGGTCTTCCTGCGCGCGCTG
CGCGTGCACTCGGTGGTGAGCGTGTACATGTGTAACCTGGCGGCCAGCGA
CCTGCTCTTCACCCTCTCGCTGCCCGTTCGTCTCTCCTACTACGCACTGCAC
CACTGGCCCTTCCCCGACCTCCTGTGCCAGACGACGGGCGCCATCTTCCAG
ATGAACATGTACGGCAGCTGCATCTTCCTGATGCTCATCAACGTGGACCG
CTACGCCGCCATCGTGCACCCGCTGCGACTGCGCCACCTGCGGCGGCCCC
GCGTGGCGCGGCTGCTCTGCCTGGGCGTGTGGGCGCTCATCCTGGTGTTTG
CCGTGCCCGCCGCCCGCGTGCACAGGCCCTCGCGTTGCCGCTACCGGGAC
CTCGAGGTGCGCCTATGCTTCGAGAGCTTCAGCGACGAGCTGTGGAAAGG
CAGGCTGCTGCCCCTCGTGCTGCTGGCCGAGGCGCTGGGCTTCCTGCTGCC
CCTGGCGGCGGTGGTCTACTCGTCGGGCCGAGTCTTCTGGACGCTGGCGC
GCCCCGACGCCACGCAGAGCCAGCGGCGGCGGAAGACCGTGCGCCTCCTG
CTGGCTAACCTCGTCATCTTCCTGCTGTGCTTCGTGCCCTACAACAGCACG
CTGGCGGTCTACGGGCTGCTGCGGAGCAAGCTGGTGGCGGCCAGCGTGCC
TGCCCGCGATCGCGTGCGCGGGGTGCTGATGGTGATGGTGCTGCTGGCCG
GCGCCAACTGCGTGCTGGACCCGCTGGTGTACTACTTTAGCGCCGAGGGC
TTCCGCAACACCCTGCGCGGCCTGGGCACTCCGCACCGGGCCAGGACCTC
GGCCACCAACGGGACGCGGGCGGCGCTCGCGCAATCCGAAAGGTCCGCC
GTCACCACCGACGCCACCAGGCCGGATGCCGCCAGTCAGGGGCTGCTCCG
ACCCTCCGACTCCCACTCTCTGTCTTCCTTCACACAGTGTCCCCAGGATTC
CGCCCTCTGA

Figure 2

OSGPR78

MVSVNSSHCFYNDSFKYTLYGCMFSMVFVLGLVSNCVAIYIFICVLKVRNETT
TYMINLAMSDLLFVFTLPFRIFYFTTRNWPFGDLLCKISVMLFYTNMYGSILFL
TCISVDRFLAIVYPFKSKTLRTKRNAKIVCTGVWLTVIGGSAPAVFVQSTHSQ
GNNASEACFENFPEATWKTYLSRIVIFIEIVGFFIPLILNVTCSSMVLKTLTKPV
TLSRSKINKTKVLKMIFVHLIIFCFCFVPYNINLILYSLVRTQTFVNCSVVAAVR
TMYPITLCIAVSNCCFDPIVYYFTSDTIQNSIKMKNWSVRRSDFRFSEVHGAEN
FIQHNLQTLKSKIFDNESAA

OSGPR114

MLANSSSTNSSVLPCPDYRPTHRLHLVVYSLVLAAGLPLNALALWVFLRALR
VHSVVSVYMCNLAASDLLFTLSLPVRLSYYALHHWPFPDLLCQTTGAIFQMN
MYGSCIFLMLINVDRYAAIVHPLRLRHLRRPRVARLLCLGVWALILVFAVPA
ARVHRPSRCRYRDLEVRLCFESFSDELWKGRLLPLVLLAEALGFLLPLAAVV
YSSGRVFWTLARPDATQSQRRRKTVRLLLANLVIFLLCFVPYNSTLAVYGLLR
SKLVAASVPARDRVRGVLMVMVLLAGANCVLDPLVYYFSAEGFRNTLRGLG
TPHRARTSATNGTRAALAQSERSAVTTDATRPDAASQGLLRPSDSHSLSSFTQ
CPQDSAL

Figure 3
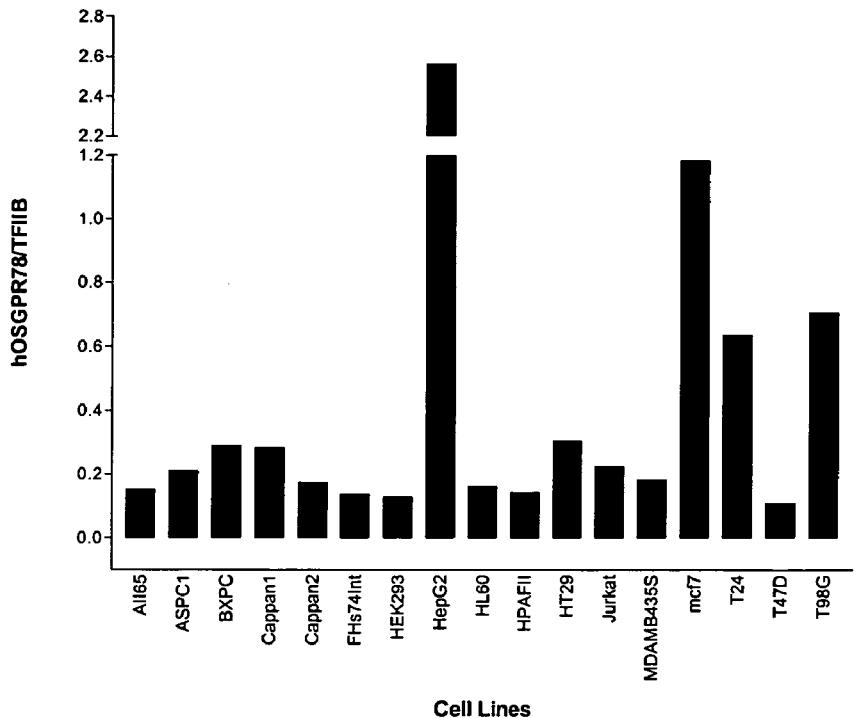
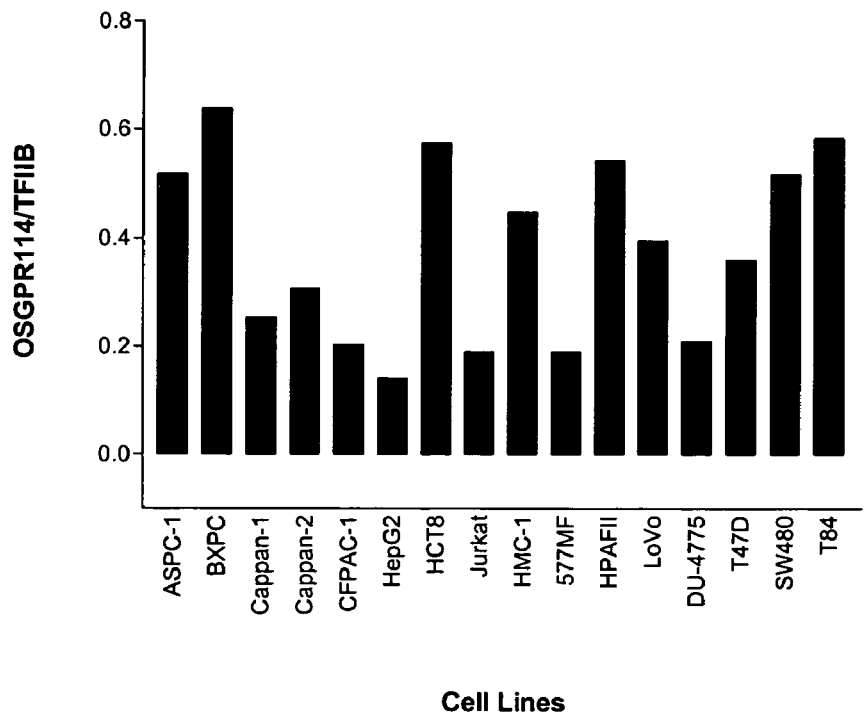

Figure 4
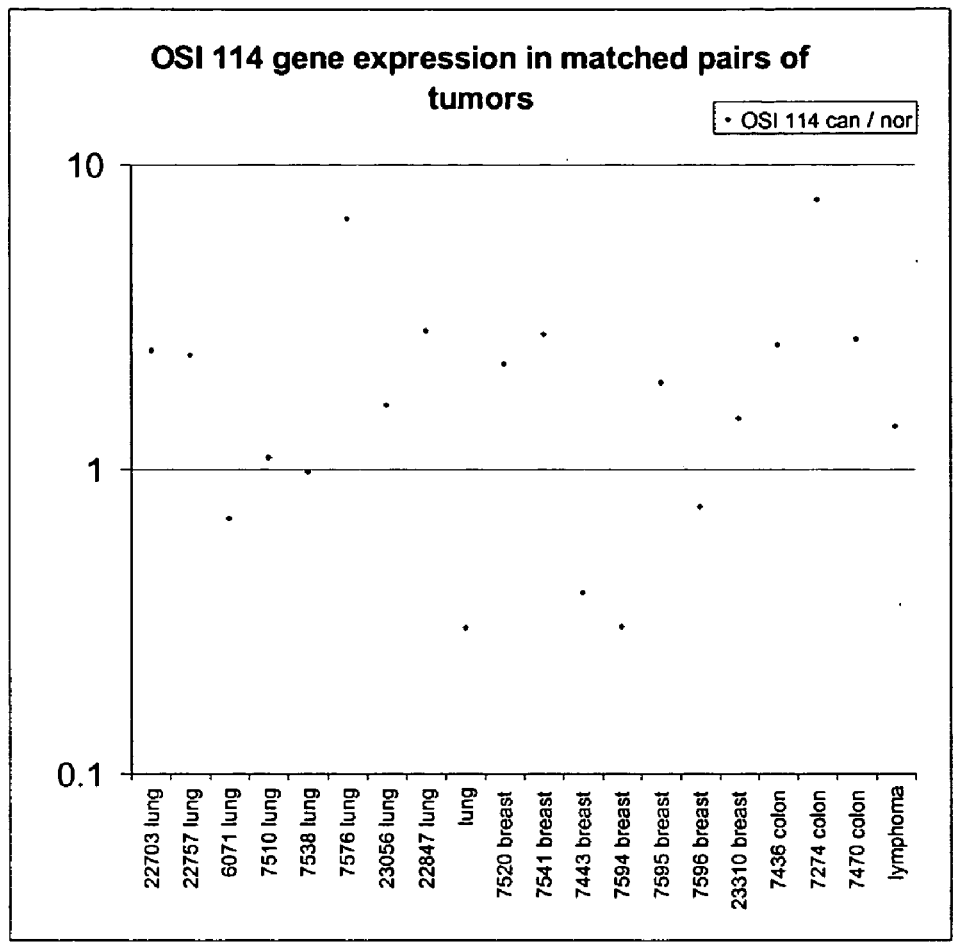
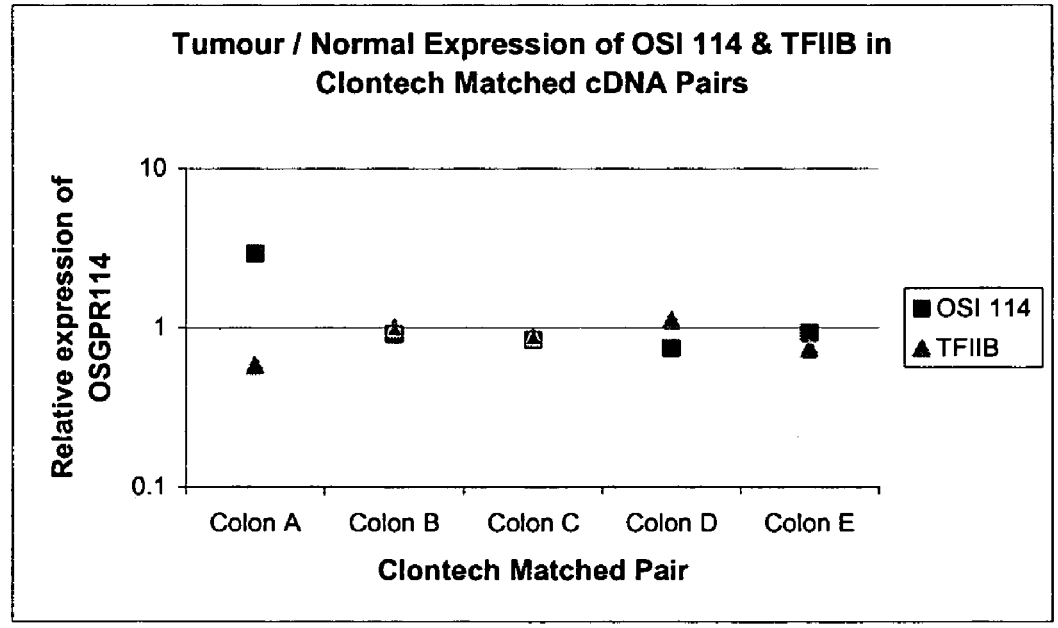

Figure 5
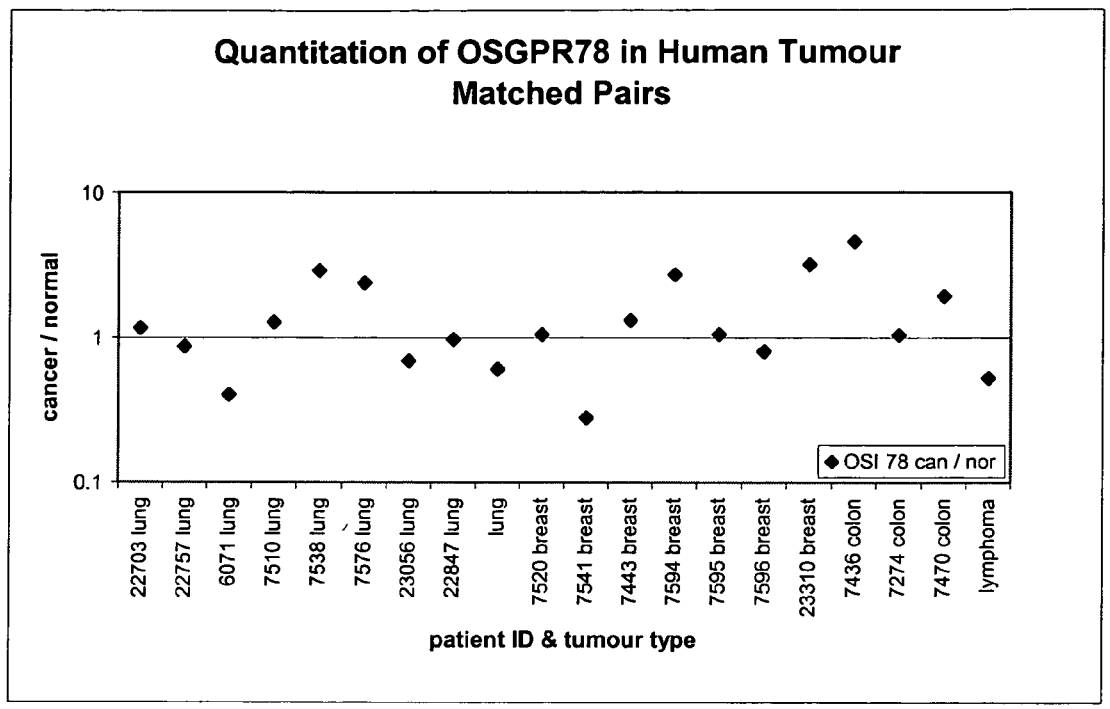
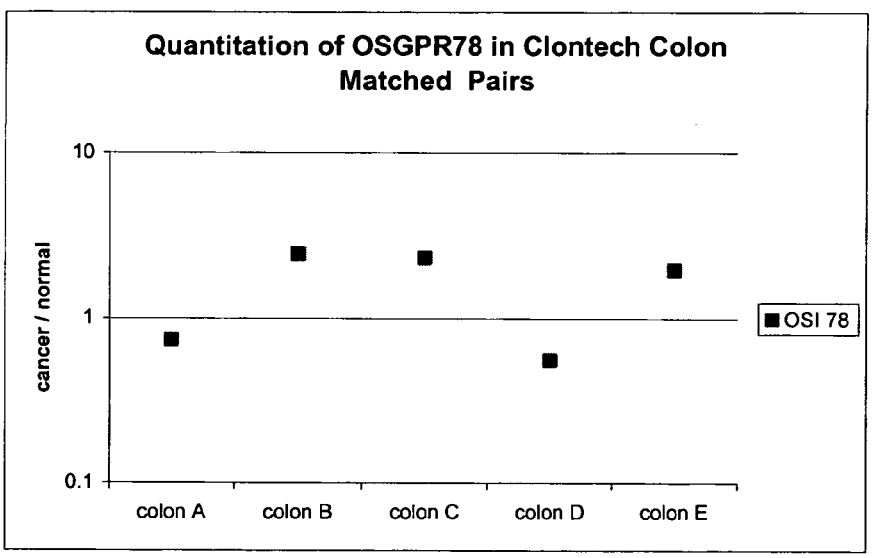

[³H]LPA binding to the membranes from CHO cells stably transfected with GPR114 (after normalized to CHO cells only, RT 1 hr incubation, ligand conc: 14 nM)

Figure 11

| Oligo Name | Oligo Sequence | Gene | Cloning Vector | Restriction Site |
|---|---|---|---|---|
| OS78NcoFWD | TGACTGCCATGGTAAGCGTTAACAGCTCCCAC | Human OSGPR78 | Yeast Cp4258 | NcoI |
| OS78XbaREV | GTCAGTTCTAGATTCAGGCAGCAGATTCATTGT | Human OSGPR78 | Yeast Cp4258 | Xba |
| OS114-Eco31F | CTTCTTGGTCTCACATGTTAGCCAACAGCTCCTCAACCAACAG | Human OSGPR114 | Yeast Cp4258 | EcoR1 |
| OS114-XbaR | CTTCTCTCTAGAGTTCAGAGGGCGGAATCCTGGGGAC | Human OSGPR114 | Yeast Cp4258 | Xba |

Figure 12

| Oligo Name | Oligo Sequence | Gene |
|---|---|---|
| OSGPR114-F1 | TTAGCCAACAGCTCCTCAACCAAC | OSGPR114 |
| OSGPR114-R1 | ACCAAGTGCAGGCGGTGG | OSGPR114 |
| OSGPR114-Tqn1 | TCTGTTCTCCCGTGTCCTGACTACCGACC | OSGPR114 |
| OSGPR78-F1 | AAATGAAAAACTGGTCTGTCAGGAG | OSGPR78 |
| OSGPR78-R1 | AGGTCTGTAGGTTATGCTGAATAAAATTC | OSGPR78 |
| OSGPR78-Tqn1 | TGACTTCAGATTCTCTGAAGTTCATGGTGCA | OSGPR78 |
| TFIIB-F1 | CAGTGTGGATTTGATTACAACTGGG | TFIIB |
| TFIIB-R1 | TGTAGCTGCCATCTGTACTTGTTTAGG | TFIIB |
| TFIIB-Tqn1 | CTTCATGTCCAGGTTCTGTTCCAACCTTTGTC | TFIIB |

Figure 13

| Tissue | OSGPR78 | OSGPR114 | Tissue | OSGPR78 | OSGPR114 |
|---|---|---|---|---|---|
| Adipose | 1.519 | 0.152 | Colon | 1.019 | 0.040 |
| Liver | 0.295 | 0.164 | Lung | 1.224 | 0.318 |
| Pancreas | 0.655 | 0.090 | Trachea | 1.909 | 0.085 |
| Sk. Muscle | 0.551 | 0.033 | Leukocyte | 0.791 | 0.369 |
| Heart | 2.103 | 0.078 | Spleen | 2.150 | 0.019 |
| Aorta | 1.868 | 0.262 | Thymus | 1.723 | 0.100 |
| Brain | 0.616 | 0.046 | Adrenal | 0.968 | 0.027 |
| Hypothalamus | 0.846 | 0.030 | Kidney | 1.238 | 0.397 |
| Cerebellum | 0.825 | 0.138 | Bladder | 1.385 | 0.095 |
| Hippocampus | 0.341 | 0.138 | Breast | 1.800 | 0.054 |
| Pituitary | 0.589 | ND | Ovary | 1.421 | 0.145 |
| Spinal Cord | 1.885 | 0.031 | Placenta | 1.969 | 0.039 |
| Stomach | 1.199 | 0.025 | Uterus | 1.752 | 0.012 |
| Intestine_small | 1.630 | 0.082 | | | |

SEQUENCE LISTING

```
<160> NUMBER OF SEQ ID NOS: 17

<210> SEQ ID NO 1
<211> LENGTH: 1035
<212> TYPE: DNA
<213> ORGANISM: Homo sapiens

<400> SEQUENCE: 1
atggtaagcg ttaacagctc ccactgcttc tataatgact cctttaagta cactttgtat      60
gggtgcatgt tcagcatggt gtttgtgctt gggttagtat ccaattgtgt tgccatatac     120
attttcatct gcgtcctcaa agtccgaaat gaaactacaa cttacatgat taacttggca     180
atgtcagact tgcttttgt ttttacttta cccttcagga ttttttactt cacaacacgg     240
```

-continued

```
aattggccat ttggagattt actttgtaag atttctgtga tgctgtttta taccaacatg      300
tacggaagca ttctgttctt aacctgtatt agtgtagatc gatttctggc aattgtctac      360
ccatttaagt caaagactct aagaaccaaa agaaatgcaa agattgtttg cactggcgtg      420
tggttaactg tgatcggagg aagtgcaccc gccgttttg ttcagtctac ccactctcag       480
ggtaacaatg cctcagaagc ctgctttgaa aattttccag aagccacatg gaaaacatat      540
ctctcaagga ttgtaatttt catcgaaata gtgggatttt ttattcctct aattttaaat     600
gtaacttgtt ctagtatggt gctaaaaact ttaaccaaac cagttacatt aagtagaagc      660
aaaataaaca aaactaaggt tttaaaaatg atttttgtac atttgatcat attctgtttc      720
tgttttgttc cttacaatat caatcttatt ttatattctc ttgtgagaac acaaacattt      780
gttaattgct cagtagtggc agcagtaagg acaatgtacc caatcactct ctgtattgct      840
gtttccaact gttgtttga ccctatagtt tactacttta catcggacac aattcagaat       900
tcaataaaaa tgaaaaactg gtctgtcagg agaagtgact tcagattctc tgaagttcat      960
ggtgcagaga atttattca gcataaccta cagaccttaa aaagtaagat atttgacaat      1020
gaatctgctg cctga                                                     1035
```

<210> SEQ ID NO 2
<211> LENGTH: 1119
<212> TYPE: DNA
<213> ORGANISM: Homo sapiens

<400> SEQUENCE: 2

```
atgttagcca acagctcctc aaccaacagt tctgttctcc cgtgtcctga ctaccgacct       60
acccaccgcc tgcacttggt ggtctacagc ttggtgctgg ctgccgggct cccctcaac      120 gcgctagccc tctgggtctt cctgcgcgcg ctgcgcgtgc actcggtggt gagcgtgtac      180
atgtgtaacc tggcggccag cgacctgctc ttcaccctct cgctgcccgt tcgtctctcc      240
tactacgcac tgcaccactg gcccttcccc gacctcctgt gccagacgac gggcgccatc      300
ttccagatga acatgtacgg cagctgcatc ttcctgatgc tcatcaacgt ggaccgctac      360
gccgccatcg tgcacccgct gcgactgcgc cacctgcggg gccccgcgt ggcgcggctg       420 ctctgcctgg gcgtgtgggc gctcatcctg gtgtttgccg tgcccgccgc ccgcgtgcac      480
aggccctcgc gttgccgcta ccgggacctc gaggtgcgcc tatgcttcga gagcttcagc      540
gacgagctgt ggaaaggcag gctgctgccc ctcgtgctgc tggccgaggc gctgggcttc      600
ctgctgcccc tggcggcggt ggtctactcg tcgggccgag tcttctggac gctggcgcgc      660
cccgacgcca cgcagagcca gcggcggcgg aagaccgtgc gcctcctgct ggctaacctc      720
gtcatcttcc tgctgtgctt cgtgcccac aacagcacgc tggcggtcta cgggctgctg      780
cggagcaagc tggtggcggc cagcgtgcct gccgcgatc gcgtgcgcgg ggtgctgatg      840
gtgatggtgc tgctggccgg cgccaactgc gtgctgaccc gctggtgta ctactttagc      900 gccgagggct ccgcaacac cctgcgcggc ctgggcactc cgcaccgggc caggacctcg      960
gccaccaacg ggacgcgggc ggcgctcgcg caatccgaaa ggtccgccgt caccaccgac     1020
gccaccaggc cggatgccgc cagtcagggg ctgctccgac cctccgactc ccactctctg     1080
tcttccttca cacagtgtcc ccaggattcc gccctctga                            1119
```

<210> SEQ ID NO 3
<211> LENGTH: 344
<212> TYPE: PRT
<213> ORGANISM: Homo sapiens

<400> SEQUENCE: 3

```
Met Val Ser Val Asn Ser Ser His Cys Phe Tyr Asn Asp Ser Phe Lys
1               5                   10                  15

Tyr Thr Leu Tyr Gly Cys Met Phe Ser Met Val Phe Val Leu Gly Leu
            20                  25                  30

Val Ser Asn Cys Val Ala Ile Tyr Ile Phe Ile Cys Val Leu Lys Val
        35                  40                  45

Arg Asn Glu Thr Thr Thr Tyr Met Ile Asn Leu Ala Met Ser Asp Leu
    50                  55                  60

Leu Phe Val Phe Thr Leu Pro Phe Arg Ile Phe Tyr Phe Thr Thr Arg
65                  70                  75                  80

Asn Trp Pro Phe Gly Asp Leu Leu Cys Lys Ile Ser Val Met Leu Phe
                85                  90                  95

Tyr Thr Asn Met Tyr Gly Ser Ile Leu Phe Leu Thr Cys Ile Ser Val
            100                 105                 110

Asp Arg Phe Leu Ala Ile Val Tyr Pro Phe Lys Ser Lys Thr Leu Arg
        115                 120                 125

Thr Lys Arg Asn Ala Lys Ile Val Cys Thr Gly Val Trp Leu Thr Val
    130                 135                 140

Ile Gly Gly Ser Ala Pro Ala Val Phe Val Gln Ser Thr His Ser Gln
145                 150                 155                 160

Gly Asn Asn Ala Ser Glu Ala Cys Phe Glu Asn Phe Pro Glu Ala Thr
                165                 170                 175

Trp Lys Thr Tyr Leu Ser Arg Ile Val Ile Phe Ile Glu Ile Val Gly
            180                 185                 190

Phe Phe Ile Pro Leu Ile Leu Asn Val Thr Cys Ser Ser Met Val Leu
        195                 200                 205

Lys Thr Leu Thr Lys Pro Val Thr Leu Ser Arg Ser Lys Ile Asn Lys
    210                 215                 220

Thr Lys Val Leu Lys Met Ile Phe Val His Leu Ile Ile Phe Cys Phe
225                 230                 235                 240

Cys Phe Val Pro Tyr Asn Ile Asn Leu Ile Leu Tyr Ser Leu Val Arg
                245                 250                 255

Thr Gln Thr Phe Val Asn Cys Ser Val Val Ala Ala Val Arg Thr Met
            260                 265                 270

Tyr Pro Ile Thr Leu Cys Ile Ala Val Ser Asn Cys Cys Phe Asp Pro
        275                 280                 285

Ile Val Tyr Tyr Phe Thr Ser Asp Thr Ile Gln Asn Ser Ile Lys Met
    290                 295                 300

Lys Asn Trp Ser Val Arg Arg Ser Asp Phe Arg Phe Ser Glu Val His
305                 310                 315                 320

Gly Ala Glu Asn Phe Ile Gln His Asn Leu Gln Thr Leu Lys Ser Lys
                325                 330                 335

Ile Phe Asp Asn Glu Ser Ala Ala
            340
```

<210> SEQ ID NO 4
<211> LENGTH: 372
<212> TYPE: PRT
<213> ORGANISM: Homo sapiens

<400> SEQUENCE: 4

```
Met Leu Ala Asn Ser Ser Thr Asn Ser Ser Val Leu Pro Cys Pro
1               5                   10                  15
```

```
Asp Tyr Arg Pro Thr His Arg Leu His Leu Val Val Tyr Ser Leu Val
             20                  25                  30

Leu Ala Ala Gly Leu Pro Leu Asn Ala Leu Ala Leu Trp Val Phe Leu
         35                  40                  45

Arg Ala Leu Arg Val His Ser Val Val Ser Val Tyr Met Cys Asn Leu
 50                  55                  60

Ala Ala Ser Asp Leu Leu Phe Thr Leu Ser Leu Pro Val Arg Leu Ser
 65                  70                  75                  80

Tyr Tyr Ala Leu His His Trp Pro Phe Pro Asp Leu Leu Cys Gln Thr
                 85                  90                  95

Thr Gly Ala Ile Phe Gln Met Asn Met Tyr Gly Ser Cys Ile Phe Leu
            100                 105                 110

Met Leu Ile Asn Val Asp Arg Tyr Ala Ala Ile Val His Pro Leu Arg
            115                 120                 125

Leu Arg His Leu Arg Arg Pro Arg Val Ala Arg Leu Leu Cys Leu Gly
        130                 135                 140

Val Trp Ala Leu Ile Leu Val Phe Ala Val Pro Ala Ala Arg Val His
145                 150                 155                 160

Arg Pro Ser Arg Cys Arg Tyr Arg Asp Leu Glu Val Arg Leu Cys Phe
                165                 170                 175

Glu Ser Phe Ser Asp Glu Leu Trp Lys Gly Arg Leu Leu Pro Leu Val
            180                 185                 190

Leu Leu Ala Glu Ala Leu Gly Phe Leu Leu Pro Leu Ala Ala Val Val
        195                 200                 205

Tyr Ser Ser Gly Arg Val Phe Trp Thr Leu Ala Arg Pro Asp Ala Thr
    210                 215                 220

Gln Ser Gln Arg Arg Arg Lys Thr Val Arg Leu Leu Leu Ala Asn Leu
225                 230                 235                 240

Val Ile Phe Leu Leu Cys Phe Val Pro Tyr Asn Ser Thr Leu Ala Val
                245                 250                 255

Tyr Gly Leu Leu Arg Ser Lys Leu Val Ala Ala Ser Val Pro Ala Arg
            260                 265                 270

Asp Arg Val Arg Gly Val Leu Met Val Met Val Leu Leu Ala Gly Ala
        275                 280                 285

Asn Cys Val Leu Asp Pro Leu Val Tyr Tyr Phe Ser Ala Glu Gly Phe
    290                 295                 300

Arg Asn Thr Leu Arg Gly Leu Gly Thr Pro His Arg Ala Arg Thr Ser
305                 310                 315                 320

Ala Thr Asn Gly Thr Arg Ala Ala Leu Ala Gln Ser Glu Arg Ser Ala
                325                 330                 335

Val Thr Thr Asp Ala Thr Arg Pro Asp Ala Ala Ser Gln Gly Leu Leu
            340                 345                 350

Arg Pro Ser Asp Ser His Ser Leu Ser Ser Phe Thr Gln Cys Pro Gln
        355                 360                 365

Asp Ser Ala Leu
    370

<210> SEQ ID NO 5
<211> LENGTH: 32
<212> TYPE: DNA
<213> ORGANISM: Artificial
<220> FEATURE:
<223> OTHER INFORMATION: probe/primer

<400> SEQUENCE: 5
```
tgactgccat ggtaagcgtt aacagctccc ac                                   32

<210> SEQ ID NO 6
<211> LENGTH: 33
<212> TYPE: DNA
<213> ORGANISM: Artificial
<220> FEATURE:
<223> OTHER INFORMATION: probe/primer

<400> SEQUENCE: 6
gtcagttcta gattcaggca gcagattcat tgt                                  33

<210> SEQ ID NO 7
<211> LENGTH: 43
<212> TYPE: DNA
<213> ORGANISM: Artificial
<220> FEATURE:
<223> OTHER INFORMATION: probe/primer

<400> SEQUENCE: 7
cttcttggtc tcacatgtta gccaacagct cctcaaccaa cag                       43

<210> SEQ ID NO 8
<211> LENGTH: 37
<212> TYPE: DNA
<213> ORGANISM: Artificial
<220> FEATURE:
<223> OTHER INFORMATION: probe/primer

<400> SEQUENCE: 8
cttctctcta gagttcagag ggcggaatcc tggggac                              37

<210> SEQ ID NO 9
<211> LENGTH: 24
<212> TYPE: DNA
<213> ORGANISM: Artificial
<220> FEATURE:
<223> OTHER INFORMATION: probe/primer

<400> SEQUENCE: 9
ttagccaaca gctcctcaac caac                                            24

<210> SEQ ID NO 10
<211> LENGTH: 18
<212> TYPE: DNA
<213> ORGANISM: Artificial
<220> FEATURE:
<223> OTHER INFORMATION: probe/primer

<400> SEQUENCE: 10
accaagtgca ggcggtgg                                                   18

<210> SEQ ID NO 11
<211> LENGTH: 29
<212> TYPE: DNA
<213> ORGANISM: Artificial
<220> FEATURE:
<223> OTHER INFORMATION: probe/primer

<400> SEQUENCE: 11
tctgttctcc cgtgtcctga ctaccgacc                                       29

<210> SEQ ID NO 12
<211> LENGTH: 25
<212> TYPE: DNA

-continued

```
<213> ORGANISM: Artificial
<220> FEATURE:
<223> OTHER INFORMATION: probe/primer

<400> SEQUENCE: 12
aaatgaaaaa ctggtctgtc aggag                                    25

<210> SEQ ID NO 13
<211> LENGTH: 29
<212> TYPE: DNA
<213> ORGANISM: Artificial
<220> FEATURE:
<223> OTHER INFORMATION: probe/primer

<400> SEQUENCE: 13
aggtctgtag gttatgctga ataaaattc                                29

<210> SEQ ID NO 14
<211> LENGTH: 31
<212> TYPE: DNA
<213> ORGANISM: Artificial
<220> FEATURE:
<223> OTHER INFORMATION: probe/primer

<400> SEQUENCE: 14
tgacttcaga ttctctgaag ttcatggtgc a                             31

<210> SEQ ID NO 15
<211> LENGTH: 25
<212> TYPE: DNA
<213> ORGANISM: Artificial
<220> FEATURE:
<223> OTHER INFORMATION: probe/primer

<400> SEQUENCE: 15
cagtgtggat ttgattacaa ctggg                                    25

<210> SEQ ID NO 16
<211> LENGTH: 27
<212> TYPE: DNA
<213> ORGANISM: Artificial
<220> FEATURE:
<223> OTHER INFORMATION: probe/primer

<400> SEQUENCE: 16
tgtagctgcc atctgtactt gtttagg                                  27

<210> SEQ ID NO 17
<211> LENGTH: 32
<212> TYPE: DNA
<213> ORGANISM: Artificial
<220> FEATURE:
<223> OTHER INFORMATION: probe/primer

<400> SEQUENCE: 17
cttcatgtcc aggttctgtt ccaacctttg tc                            32
```

METHODS FOR IDENTIFICATION OF MODULATORS OF OSGPR114 OR OSGPR78 ACTIVITY, AND THEIR USE IN THE TREATMENT OF DISEASE

CROSS-REFERENCE TO RELATED APPLICATIONS

This application claims the benefit of U.S. Provisional Application No. 60/482,964, filed Jun. 27, 2003, which is herein incorporated by reference in its entirety.

STATEMENT REGARDING FEDERALLY SPONSORED RESEARCH OR DEVELOPMENT

Not applicable.

REFERENCE TO SEQUENCE LISTING

A complete sequence listing section is included herein.

BACKGROUND OF THE INVENTION

This invention relates to the identification of lysophosphatidic acid (LPA) as a ligand for the G-protein coupled receptors OSGPR114 and OSGPR78, and is directed to in vitro methods for screening candidate drugs for their ability to modulate the activity of OSGPR114 or OSGPR78, and to methods of treating disease by administering to an individual a therapeutic amount of a modulator of OSGPR114 or OSGPR78.

G-protein coupled receptors (GPCRs) are a super-family of membrane receptors that mediate a wide variety of biological functions. Upon binding of extracellular ligands, GPCRs interact with a specific subset of heterotrimeric G proteins that can, in their activated forms, inhibit or activate various effector enzymes and/or ion channels. All GPCRs are predicted to share a common molecular architecture consisting of seven transmembrane helices linked by alternating intracellular and extracellular loops. The extracellular receptor surface has been shown to be involved in ligand binding whereas the intracellular portions are involved in G-protein recognition and activation. Different G-protein alpha-subunits, and beta-gamma subunit complexes, preferentially stimulate or inhibit particular effector molecules to modulate various biological functions in a cell. Typical effector molecules include adenylate cyclase, phospholipases C and A2, cGMP phosphodiesterase-γ, and potassium, sodium and calcium channels. Additional regulation of GPCR activity is thought to occur via receptor oligomerization and interaction with the protein β-arrestin (e.g. see Rocheville, M. et. al. (2000) Science 288:154-157; Gether, U. (2000) Endocrine Reviews 21:90-113; Luttrel, L. M. et. al. (1999) Science 283:655-661). G-protein coupled receptors are found ubiquitously in all cell types within mammalian organisms. Many therapeutic agents targeting GPCR receptors have been successfully introduced onto the market, thereby establishing their value as targets for drug discovery and development (e.g. Wise, A. et al. 2002, DDT, 7:235-246). Over 30% of clinically marketed drugs are active on GPCRs.

It has been estimated that for about 40% of GPCRs in the human genome (excluding sensory receptors) the ligand remains unknown. Such GPCRs are commonly referred to as "orphan" receptors. For example, the primary structures of a human isoform of the orphan GPCRs OSGPR114 and OSGPR78, or closely related GPCRs, have been described in recent patent applications (e.g. OSGPR114 in WO 01/90187, WO 01/87937, WO 01/42288, WO 01/77326, WO 01/48189, WO 01/31014, WO 01/04292, WO 01/02563, WO 00/23588, WO 00/31258, WO 00/50458 and EP 1090926 A1; and OSGPR78 in WO 96/30406). The DNA and amino acid sequences for OSGPR114 and OSGPR78 have also been described in the scientific literature. A chicken homolog of OSGPR78 was originally identified in chicken activated T-cells and named 6H1 by Kaplan (Kaplan et. al. (1993) J. Immunol. 151(2):628-636). Webb (Webb et. al. (1996) Biochem. Biophys. Res. Commun. 219(1):105-110) followed the disclosure of the sequence with a proposal that the receptor bound to ATP, and therefore named it P2Y5 as the fifth member of the purinergic GPCR P2Y family. However, subsequent studies (Li et. al. (1997) Biochem. Biophys. Res. Commun. 236(2):455-60); and experiments described herein) could not find evidence that the receptor was in fact activated by nucleotides, thus calling into question the classification as a P2Y receptor. The human OSGPR78 was sequenced earlier, while sequencing the complete genomic sequence of the human retinoblastoma susceptibility gene (Toguchida et al. (1993) Genomics 17: 535-543), but it was not appreciated until later that the human P2Y5 receptor is encoded in the intron 17 of the retinoblasoma gene (Herzog et al. 1996, Genome research 6: 858-61; Bohm et al. 1997, Genbank entry locus AAB62190, direct submission to Genbank). In the scientific literature, OSGPR114 was originally identified by White (White et. al. (2000) Nat. Genet. 26, 345-348) and named gpr92. Lee (Lee et. al. (2001) Gene 275(1):83-91) also disclosed the sequence.

No information outwith nucleic acid and amino acid sequence homologies and expression patterns for OSGPR114 or OSGPR78 have been described in the scientific literature, e.g. no activating ligand has been identified. Similarly, in the above patent applications OSGPR114 and OSGPR78 are described as tools for identifying drugs for the treatment of a variety of pathophysiological conditions. However, none of these applications identify a function for either of these GPCRs, or describes a ligand that binds to either receptor and modulates its activity.

It has been previously shown that LPA has the ability to modulate cell motility and growth and to stimulate tumor growth; to modulate the development and regulation of the cardiovascular system including a contribution to artherosclerosis and a role in wound healing and tissue regeneration; to regulate the differentiation of multiple cell types including the induction of differentiation of preadipocytes into adipocytes; and to have influence over the physiology and pathophysiology of the reproductive tracts of males and of females. Prior to the work described herein, the effects of LPA in these and other systems were thought to be exclusively the result of interaction with the LPA receptors LPA-1, -2 and -3, previously known as Edg-2, -4 and -7 (Chun, J., et al. (2002) Pharmacol. Reviews 54:265-269).

LPA is one of the simplest phospholipids found in nature and consists of a glycerol moiety with a fatty acid backbone at the sn1 (or sn2) position, a phosphate group at the sn3 position and a hydroxyl at the sn2 (or sn1) site. It has been shown that endogenous LPA species can contain multiple fatty acids. These fatty acids may vary in their chain length, the amount of unsaturation/saturation and may consist of an acyl or alkyl linkage. It has been shown that in some cases, the predominant species of LPA may vary between tissues and/or cell types and is influenced by the available precursor lipids within a particular cell or tissue. The biosynthetic pathways and metabolic pathways of LPA may also vary between cells and are only moderately well characterized. Intracellular and extracelullar synthetic and degradative pathways for LPA are also different, as are the physiological roles of LPA on either side of the cell membrane.

Amongst the multiple known biological roles of LPA, much of the scientific literature attention has been focused on the ability of LPA to act as a proliferative signal to cells of multiple origins, especially malignant cells. In addition to acting as a growth stimulator to cancer cells, LPA has been demonstrated by multiple studies to act as a motility factor and an angiogenic factor in carcinogenesis and cancer progression. It has been shown to increase the invasive capacity of cancer cells, and to have an important role in increasing the metastatic potential of tumors. It is therefore known that LPA is strongly implicated in controlling and contributing towards virtually all aspects of malignant disease. One of the original studies on the role of LPA in cancer identified "ovarian cancer activating factor" as LPA (Xu et. al. 1995 Clin. Cancer Res. 1(10): 1223-32). Additionally, increased tumor production of LPA has been observed and the enzyme responsible for this shown to be upregulated in multiple cancers. Further validation of the role of LPA in cancer disease is shown by the fact that induction or expression of enzymes that degrade LPA do not only prevent the activity of LPA in disease progression in vitro, but also dramatically reduce tumor growth in vivo (Tanyi et. al. 2003 Cancer Res. 63(5):1073-1082). Additionally, LPA levels in the blood, and in ascites, have been shown to be significantly higher in patients with ovarian cancer than in patients who do not have ovarian cancer. The degree of this elevation in blood LPA has been correlated with tumor malignancy. As well as inducing the growth of ovarian cancer cells, LPA also increases their motility and invasiveness and at concentrations present in ascites, prevents cisplatin-induced apoptosis. In summary, there is an extensive body of public literature that conclusively demonstrates that LPA signaling is aberrant in multiple cancers. Cancer types that have been implicated as involving dysregulated LPA signaling, in addition to ovarian cancer, include cancers of the lung, prostate, pancreas, colon, breast, esophagus, kidney and stomach, and glioma, lymphoma, leukemia and melanoma.

The molecular mechanisms behind the involvement of LPA in cancer are the subject of multiple reviews (e.g. Fang et. al. (2000) Ann. N.Y. Acad. Sci. 905:188-208; Fujita et. al. (2003) Cancer Letts 192:161-9; Erickson et. al. (2001) Prostaglandins and other Lipid Mediators 64: 63-81; Daaka (2002) Biochim. Biophys. Acta 1582: 265-269; Fukushima et. al. (2001) Ann. Rev. Pharm. Toxicol. 41:507-34). Although LPA is known to act as both an intracellular and extracellular signaling moiety, most studies investigating the role of LPA in cancer have focused on its role as an autocrine and paracrine growth factor, predominantly stimulating the growth of cancer cells and tumors. Such extracellular signaling pathways have also been shown to be intimately involved in increases in cancer cell motility, invasiveness, angiogenesis and metastasis resulting from LPA administration to cancer cells. The extracellular signaling of LPA is known to be transduced to the cell interior via LPA specific GPCRs. Such receptors have been described in the literature, and there are three that have been well characterized to date, LPA1, LPA2 and LPA3. They were previously named Edg2, Edg4 and Edg7 due to their high homology with other phospholipid receptors Edg 1, 3, 5, 6 and 8, (which are now known as Sphingosine 1-phosphate (SIP) receptors 1 to 5). Edg is an acronym for "endothelial differentiation gene". Very recently a fourth LPA receptor, p2y9/GPR23, has also been reported (Noguchi et. al. (2003) J. Biol. Chem. April 30, electronic manuscript M302648200 ahead of print). p2y9/GPR23 is only distantly related to LPA1, LPA2 and LPA3. Additionally, activation of GPCRs by LPA is also known to transactivate other growth factors involved in cancer development, such as the epidermal growth factor receptor and the platelet-derived growth factor receptor (for review see Wu and Cunnick (2002) Biochim. Biophys. Acta. 1582(1-3): 100-106). The effects of LPA on mitogenesis and survival likely involve activation of ERK and transactivation of other growth factor receptors, whereas the effects on motility and invasion probably occur through Rho-based signaling, probably via coupling of the receptor to Galpha 12/13. The effects on angiogenesis probably occur through the induction of proangiogenic factors such as VEGF.

Despite the considerable body of literature in this area, a complete understanding of LPA action in modulating cell proliferation and tumor growth at the molecular level has not yet been achieved. Consequently, without a full understanding of its mechanism of action, there are considerable problems associated with developing compounds that antagonize such effects of LPA. To help alleviate this problem, the surprising discovery described herein that certain LPA compounds are ligands of OSGPR114 and OSGPR78, and therefore that the latter are novel members of the family of LPA-activated GPCRs, suggests that the effect of LPA as a physiological modulator of various physiological systems is not limited to interaction with the previously known LPA receptors. Thus, this discovery provides an additional mechanism of action for LPA, additional targets for therapeutic modulation, and thus a basis for further assay and drug development. Several compounds are already under development as modulators of the activity of other LPA receptors (e.g. EP 1258484 A1, WO 02/29001, US 2003/0027800 A1 and U.S. Pat. No. 6,380,177; Fischer, D. J., et al. (2001) Mol Pharmacol. 60(4):776-84; Hasegawa, Y., et al. (2003) J. Biol. Chem. 278(14):11962-9; Heise, C. E., et al. (2001) Mol. Pharmacol. 60(6):1173-80; Hooks, S. B., et al. (2001) J Biol. Chem. 276(7):4611-21; Hopper, D. W., et al. (1999) J. Med. Chem. 42(6):963-70; Tigyi, G. (2001) Mol Pharmacol. 60(6): 1161-4; Yokoyama, K., et al. (2002). Biochim. Biophys. Acta 1582 (1-3): 295-308; Gueguen, G., et al. (1999) Biochemistry 38(26): 8440-50; Lynch, K. R. and T. L. Macdonald (2002). Biochim. Biophys. Acta 1582(1-3): 289-94; Sardar, V. M., et al. (2002) Biochim. Biophys. Acta 1582: 309-307 and Virag, T., et al. (2003) Mol Pharmacol. 63(5):1032-42). Some of these compounds have been found to have selective activity on one or more LPA receptors, while others have equivalent activity on all LPA receptors tested.

SUMMARY OF THE INVENTION

The present invention is based on the finding that both of the G-protein coupled receptors OSGPR114 and OSGPR78 are able to act as receptors for lysophosphatidic acid (LPA) and that cells transfected to express OSGPR114 or OSGPR78 gain the ability to elicit Gi/o (i.e. Gi and/or Go) or other G-protein mediated responses following exposure to LPA. Suitable LPA compounds include, but are not limited to, myristoyl lysophosphatidic acid, oleoyl lysophosphatidic acid, palmitoyl lysophosphatidic acid, and stearoyl lysophosphatidic acid, or a functional analog or homolog of one of these compounds. Identification of a ligand for OSGPR114 or OSGPR78 therefore facilitates the development of screening methods for identifying modulators of the OSGPR114 or OSGPR78 receptor.

Accordingly the invention further provides a method for identifying agents which modulate the activity of OSGPR114 or OSGPR78 receptor, which comprises determining whether the test agent interacts with OSGPR114 or OSGPR78. The method may comprise the use of OSGPR114 or OSGPR78 in combination with an LPA ligand. The invention further comprises the use of agents identified using the method of the invention in the treatment of diseases mediated by OSGPR114 or OSGPR78 and their use in the manufacture of a medicament for the treatment of OSGPR114 or OSGPR78 mediated diseases. Accordingly, the invention further provides a method of treatment of diseases or conditions mediated by OSGPR114 or OSGPR78 in an individual, which comprises the administration of a therapeutically effective amount of an OSGPR114 or OSGPR78 receptor modulator. The invention also provides the use of a modulator of OSGPR114 or OSGPR78 in the manufacture of a medicament for the treatment of diseases or conditions mediated by OSGPR114 or OSGPR78.

BRIEF DESCRIPTION OF THE FIGURES

FIG. 1: Nucleotide sequence encoding human OSGPR114 (FIG. 1A, SEQ I.D. NO:1) and OSGPR78 (FIG. 1B, SEQ I.D. NO:2) receptors.

FIG. 2: Deduced amino acid sequence of human OSGPR114 (SEQ I.D. NO:3) and OSGPR78 (SEQ I.D. NO:4) receptors FIG. 3: OSGPR78 and OSGPR114 expression profile in human cell lines. Data is expressed as a ratio of TFIIB expression levels in the same cell lines and the experiment conducted as detailed in the Materials and Methods section.

FIG. 4: OSGPR114 gene expression in matched pairs of human tumors. Data is expressed as a ratio of TFIIB expression levels in the same tissues and the experiment conducted as detailed in the Materials and Methods section.

FIG. 5: OSGPR78 gene expression in matched pairs of human tumors. Data is expressed as a ratio of TFIIB expression levels in the same tissues and the experiment conducted as detailed in the Materials and Methods section.

FIG. 11: Oligonucleotides designed for PCR cloning of human OSGPR114 and OSGPR78 (SEQ I.D. NOS:5-8). Oligonucleotides for the human homolog were based on the predicted sequence based on human genomic sequencing information.

FIG. 12: Oligonucleotides designed for quantitative RT-PCR using fluorogenic probe for OSGPR114, OSGPR78 and TFIIB (SEQ I.D. NOS:9-17).

FIG. 13: OSGPR114 and OSGPR78 expression profile in normal human tissues. Data is expressed as a ratio of TFIIB expression levels in the same tissues and the experiment conducted as detailed in the Materials and Methods section.

DETAILED DESCRIPTION OF THE INVENTION

Figure 6:
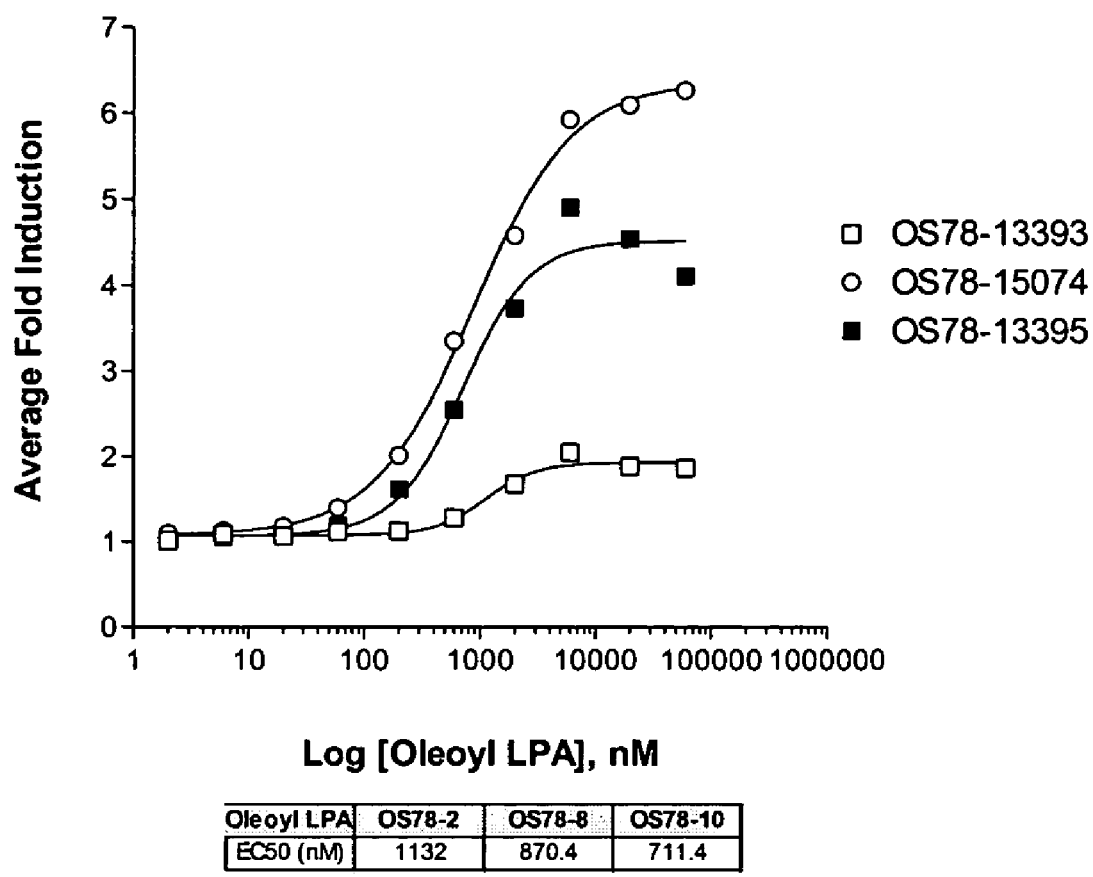
FIG. 6: Effects of LPA at OSGPR78. The experiment was conducted as detailed in the Materials and Methods section. Briefly, engineered yeast cells expressing different Galpha chimeric subunits and two reporter genes, URA-Fus1p-LacZ and TRP-Fus1p-LacZ were incubated with LPA. The yeast cells were tested with and without OSGPR78 expression. β-galactosidase activity was measured and the result expressed as a fold-induction over basal β-galactosidase activity. LPA stimulation of fluorescence was only observed in receptor transformed yeast cells and not in vector transformed yeast cells or in yeast cells of similar chimeric backgrounds expressing other receptors.

This invention relates to the identification of LPA, including, but not limited to myristoyl lysophosphatidic acid, oleoyl lysophosphatidic acid, palmitoyl lysophosphatidic acid, and stearoyl lysophosphatidic acid, or a functional analog or homolog of one of these compounds, as ligands of the G-protein coupled receptor OSGPR114 or OSGPR78, and is directed to in vitro methods for screening candidate drugs for their ability to modulate the activity of OSGPR114 or OSGPR78, and to methods of treating disease by administering to an individual a therapeutic amount of a modulator of OSGPR114 or OSGPR78.

The discovery that OSGPR114 or OSGPR78 is a physiological target protein of LPA, a compound known to stimulate proliferation of many cell types, in addition to other activities, will allow for the identification and development of new drugs that also act via this protein, and for the identification of other targets in the OSGPR114 or OSGPR78 signal transduction pathways that can themselves be a target for new drugs. This invention is the first demonstration of an activation of the OSGPR114 or OSGPR78 receptor by LPA. Several physiological target proteins for LPA have been described previously, but the ability of LPA to act as a ligand for the GPCR proteins OSGPR114 or OSGPR78 was unknown until the discovery described herein. Without knowledge of the target protein for compounds such as LPA it is very difficult and expensive to develop effective compounds with either similar or antagonistic activity. By providing alternative targets that LPA can act through, the invention described herein provides a new approach to the development of such compounds. Although one could have previously designed screens using recombinant OSGPR114 and OSGPR78, there would have been little motivation to do so, as there was no indication that such compounds could be used to modulate physiological and pathological processes that involve LPA signaling, such as tumor growth. Furthermore, without the knowledge that LPA is the activating ligand for OSGPR114 and OSGPR78, the development of antagonists, or other modulators that inhibit the activity of these receptors, would have been an extremely difficult task.

This invention thus facilitates the design of simple and relatively inexpensive screens to identify novel compounds that act via OSGPR114 or OSGPR78, and that have potential as modulators of cell growth and as anti-cancer agents. Furthermore, the recognition that OSGPR114 or OSGPR78 is a potential target for anti-cancer drugs will lead to the identification of other proteins in the OSGPR114 or OSGPR78 signal transduction pathway that can themselves be targets for potential anti-cancer agents.

Prior to this invention, the utility of the OSGPR114 or OSGPR78 receptor was unknown. The discovery that LPA, including myristoyl lysophosphatidic acid, oleoyl lysophosphatidic acid, palmitoyl lysophosphatidic acid, and stearoyl lysophosphatidic acid, can act as ligands for these GPCR proteins indicates that diseases or conditions mediated by OSGPR114 or OSGPR78 include cancer (including, but not limited to, ovarian cancer and other gynecological cancers (e.g. endometrial, cervical), cancers of the lung, prostate, pancreas, colon, breast, esophagus, kidney and stomach, and glioma, multiple myeloma, lymphoma, leukemia and melanoma), obesity, certain diseases of the cardiovascular and respiratory systems, including artherosclerosis, restenosis and acetylcholine-induced airway hyperresponsiveness, wound healing, osteoporosis, inflammation, reproductive function, abnormal immune system regulation, abnormalities in neuronal growth, survival and signaling, renal failure associated with renal ischemia, and additionally those affected by or induced by obesity, including diabetes, dyslipidemia and cardiovascular disease associated with obesity, including atherosclerosis, arteriosclerosis, hypercholesteremia and hypertriglyceridemia, type 2 diabetes, type 1 diabetes, insulin resistance, metabolic syndrome (syndrome X) and hyperlipidemia. By the term OSGPR114 or OSGPR78-mediated disease, it is meant those diseases or conditions where the modulation of OSGPR114 or OSGPR78 by agonists or antagonists results in a beneficial modification of the disease state or condition.

Of the above conditions and diseases, antagonists, inverse agonists, partial inverse agonists and allosteric or allotopic antagonists of OSGPR114 should generally be useful for treating certain cancers (e.g. ovarian cancer and other gynecological cancers, cancers of the lung, prostate, pancreas, colon, breast, esophagus, kidney and stomach, and glioma, lymphoma, leukemia and melanoma), obesity, atherosclerosis, restenosis, renal ischemia, and certain reproductive disorders. Agonists, partial agonists and allosteric or allotopic agonists of OSGPR114 should generally be useful for treating wound healing and immune system disorders requiring activation of immune system cells (e.g. T-cells). Additionally, inhibition of OSGPR114 or OSGPR78 (e.g. by antagonists, inhibition of gene expression, inhibition of downstream signaling pathways) will be useful in other conditions in which LPA is implicated as a causative factor. Similarly, in diseases where LPA may be beneficial (e.g. neuron growth, obesity), specific activators of OSGPR114 or OSGPR78 or their signaling pathways could prove therapeutically beneficial.

In the case of neuronal disorders, LPA has been shown to have both proliferative and apoptotic effects depending on the cell type (e.g. Xiaoqin Y., et. al. (2002) Biochem. Biophys. Acta 1585:108-113). Thus the type of compound required for therapy of neural cells will depend on the cell type and whether activation of inhibition of growth is desired (e.g. growth inhibition would be desirable in cancers of the CNS, but growth stimulation may be desirable in neural diseases where CNS regeneration is required). Furthermore, in certain other cell types where LPA is found to have an effect opposite to that normally encountered for that cell type, due perhaps to a different G-protein coupling mechanism, the type of modulator required to treat a condition or disease may be the opposite of that normally required for that cell type. Modulators of OSGPR114 or OSGPR78 that affect OSGPR114 or OSGPR78 oligomerization (e.g. homodimerization or heterodimerization) or interaction with other GPCRs may also be useful for treating the conditions and diseases listed above.

In addition to the effects of LPA mentioned above, increased OSGPR114 or OSGPR78 expression in certain cancer types (e.g. lung, breast and colon) provides additional evidence of involvement of OSGPR114 or OSGPR78 in cancers of these tissues. Thus, modulation of OSGPR114 or OSGPR78 activity by antagonists of these LPA activated receptors may result in a beneficial modification of these disease states or conditions.

OSGPR114 or OSGPR78 may therefore be used as a screening target for the identification and development of novel pharmaceutical agents for use in the methods of the invention. A modulator of OSGPR114 or OSGPR78 may be identified by contacting a cell expressing on its surface the receptor OSGPR114 or OSGPR78, said receptor being associated with a second component capable of providing a detectable signal in response to the binding of an agent to said receptor, with an agent to be screened under conditions to permit binding to the receptor; and determining whether the agent binds to, and activates, or inhibits, the receptor, by detecting the presence or absence of a signal generated from the interaction of the compound with the receptor and thereby determining whether the test agent modulates OSGPR114 or OSGPR78 activity. This may be carried out in the presence of a labeled or unlabeled ligand, e.g. LPA, including, but are not limited to, myristoyl lysophosphatidic acid, oleoyl lysophosphatidic acid, palmitoyl lysophosphatidic acid, and stearoyl lysophosphatidic acid, or a functional analog or homolog of one of these compounds.

An agent, or pharmaceutical agent, that can be tested for activity on the OSGPR114 or OSGPR78 receptor includes any chemical compound, including small molecules (<approx. 5000 Daltons molecular weight) and macromolecules (e.g. a polypeptide or protein, nucleic acid, glycoprotein, complex carbohydrate, synthetic or natural polymer etc.). Thus, an agent may be selected from combinatorial libraries, defined chemical entities, peptide and peptide mimetics, oligonucleotides and natural product libraries, and other entities such as display (e.g. phage display libraries) and antibody products. In one embodiment, the test agent is an LPA, or a closely related compound. Thus an agent that modulates the activity of OSGPR114 or OSGPR78 can be any chemical compound that binds to and modulates the activity of OSGPR114 or OSGPR78. Such agents that modulate the activity of OSGPR114 or OSGPR78 can additionally be test agents for use in further methods or processes to determine their effects on cells or subjects, including animal models or patients.

This invention thus provides a method for identifying agents that modulate the activity of the OSGPR114 or OSGPR78 receptor, which comprises determining whether the agent interacts with OSGPR114 or OSGPR78 in a preparation comprising OSGPR114 or OSGPR78 receptor protein. The method may be carried out in combination with a ligand for OSGPR114 or OSGPR78, wherein the ligand is an LPA, or a functional analog or homolog of such a compound. In one embodiment the lysophosphatidic acid is selected from 1-myristoyl lysophosphatidic acid, 1-oleoyl lysophosphatidic acid, 1-palmitoyl lysophosphatidic acid, and 1-stearoyl lysophosphatidic acid. In an alternative embodiment, the ligand may be a compound that activates LPA receptors other than OSGPR114 or OSGPR78, such as the Edg receptors LPA1, LPA2, and LPA3, including, for example, but not limited to, those described in WO 02/29001; US 2003/0027800 A1; U.S. Pat. No. 6,380,177; Hasegawa, Y., et al. (2003) J. Biol. Chem. 278(14):11962-9; Heise, C. E., et al. (2001) Mol. Pharmacol 60(6):1173-80; Hooks, S. B., et al. (2001) J Biol. Chem. 276(7):4611-21; Hopper, D. W., et al. (1999) J. Med. Chem. 42(6):963-70; Tigyi, G. (2001) Mol Pharmacol. 60(6):1161-4; Yokoyama, K., et al. (2002). Biochim. Biophys. Acta 1582(1-3): 295-308; Gueguen, G., et al. (1999). Biochemistry 38(26): 8440-50; Lynch, K. R. and T. L. Macdonald (2002). Biochim. Biophys. Acta 1582(1-3): 289-94; Sardar, V. M., et al. (2002) Biochim. Biophys. Acta 1582: 309-307 and Virag, T., et al. (2003) Mol Pharmacol. 63(5): 1032-42.

Furthermore, in any of the methods, processes or screening assays described herein as embodiments of this invention for identifying compounds which bind to or are modulators of OSGPR114 or OSGPR78 activity, where a ligand or compound known to bind to or activate the OSGPR114 or OSGPR78 receptor is included in the method, process or assay (e.g. a competitive binding assay, or an assay for identifying antagonists), the ligand may be an LPA. In the context of this invention LPA (lysophosphatidic acid) is defined as a compound comprising a glycerol moiety with a fatty acid group at the sn1 (or sn2) position, a phosphate group at the sn3 position and a hydroxyl group at the sn2 (or sn1) site (e.g. Formula 1, 1-fatty acyl-LPA). The fatty acid group may vary in the carbon chain length from C14 (myristoyl) through C22 (docosatetraenoyl), i.e. can be selected from carbon chain lengths of C14, C15, C16, C17, C18, C19, C20, C21 and C22.

The fatty acid may be saturated or unsaturated. In one embodiment, the degree of unsaturation may vary from one to six carbon double bonds. For example, suitable fatty acid groups include, but are not limited to, palmitoyl (C16:0), linoleoyl (C18:2), oleoyl (C18:1), stearoyl (C18:0) and arachidonyl (C20:4). Included within the definition of LPA are compounds in which the fatty acid ester linkage is replaced by an alkyl ether or alkenyl ether linkage, at either the sn1 or sn2 position. (e.g. formula 2). In these alkyl or alkenyl ether compounds the carbon chain length may vary from C14 through C22, i.e. can be selected from carbon chain lengths of C14, C15, C16, C17, C18, C19, C20, C21 and C22. In one embodiment, the degree of unsaturation in the alkenyl compounds may vary from one to six carbon double bonds.

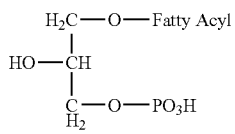
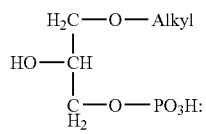

Formula 1: 1-fatty acyl-LPA          Formula 2

Thus in one embodiment of this invention lysophosphatidic acid is selected from myristoyl lysophosphatidic acid, oleoyl lysophosphatidic acid, palmitoyl lysophosphatidic acid, stearoyl lysophosphatidic acid, linoleoyl lysophosphatidic acid, linolenoyl lysophosphatidic acid, arachidonoyl lysophosphatidic acid, myristoyl lysophosphatidic acid, elaidoyl lysophosphatidic acid, palmitoleoyl lysophosphatidic acid, petroselinoyl lysophosphatidic acid, palmitvaccenoyl lysophosphatidic acid, vaccenoyl lysophosphatidic acid, erucoyl lysophosphatidic acid, brassidoyl lysophosphatidic acid, clupanodonoyl lysophosphatidic acid, eleostearoyl lysophosphatidic acid, behenoyl lysophosphatidic acid, pentadecanoyl lysophosphatidic acid, heptadecanoyl (i.e. margaroyl) lysophosphatidic acid, nonadecanoyl lysophosphatidic acid, and henicosanoyl lysophosphatidic acid.

In an alternative embodiment the lysophosphatidic acid is selected from 1-myristoyl lysophosphatidic acid, 1-oleoyl lysophosphatidic acid, 1-palmitoyl lysophosphatidic acid, and 1-stearoyl lysophosphatidic acid.

In yet another embodiment, in any of the methods, processes or screening assays described herein as embodiments of this invention for identifying compounds which bind to or are modulators of OSGPR114 or OSGPR78 activity, where a ligand or compound known to bind to or activate the OSGPR114 or OSGPR78 receptor is included in the method, process or assay (e.g. a competitive binding assay, or an assay for identifying antagonists), the ligand may be a homolog or analog of LPA as defined above.

Furthermore, in an alternative embodiment, in any of the methods, processes or screening assays described herein as embodiments of this invention for identifying compounds which bind to or are modulators of OSGPR114 or OSGPR78 activity, where a ligand or compound known to bind to or activate the OSGPR114 or OSGPR78 receptor is included in the method, process or assay (e.g. a competitive binding assay, or an assay for identifying antagonists), the ligand may be a compound that activates LPA receptors other than OSGPR114 or OSGPR78, such as the Edg receptors LPA1, LPA2, and LPA3, including, for example, but not limited to, those described in WO 02/29001; US 2003/0027800 A1; U.S. Pat. No. 6,380,177 Hasegawa, Y., et al. (2003) J. Biol. Chem. 278(14):11962-9; Heise, C. E., et al. (2001) Mol. Pharmacol 60(6):1173-80; Hooks, S. B., et al. (2001) J Biol. Chem. 276(7):4611-21; Hopper, D. W., et al. (1999) J. Med. Chem. 42(6):963-70; Tigyi, G. (2001) Mol Pharmacol. 60(6):1161-4; Yokoyama, K., et al. (2002). Biochim. Biophys. Acta 1582 (1-3): 295-308; Gueguen, G., et al. (1999). Biochemistry 38(26): 8440-50; Lynch, K. R. and T. L. Macdonald (2002). Biochim. Biophys. Acta 1582(1-3): 289-94; Sardar, V. M., et al. (2002) Biochim. Biophys. Acta 1582: 309-307 and Virag, T., et al. (2003) Mol Pharmacol. 63(5): 1032-42 as compounds that are activators of LPA receptors (edg receptors). The ligand may be specific compounds as described therein, or specific examples of structures that are encompassed by a structure that defines a genus.

Furthermore, in any of the methods, processes or screening assays described herein as embodiments of this invention for identifying compounds which bind to or are modulators of OSGPR114 or OSGPR78 activity, where a ligand or compound known to bind to or activate the OSGPR114 or OSGPR78 receptor is included in the method, process or assay, in one embodiment a ligand concentration is selected that produces a submaximal activation of OSGPR114 or OSGPR78 (e.g. 5%, 10%, 20%, or 50% of maximal response) in order to identify agonists, partial agonists or allosteric or allotopic agonists. Identification of allosteric or allotopic agonists will be dependent on the presence of such an activating ligand, and would not have been possible prior to the identification of LPA as a ligand for OSGPR114 or OSGPR78 as described herein.

For example, a method for identification of an agent that modulates OSGPR114 or OSGPR78 comprises (i) contacting a test agent with a cell (including but not limited to cells such as a breast, colon, lung or ovarian cell, or other cells known to express OSGPR114 or OSGPR78) which expresses OSGPR114 or OSGPR78 or a variant thereof that is capable of coupling to a G-protein; and (ii) monitoring for OSGPR114 or OSGPR78 activity in the presence of a G protein; thereby determining whether the test agent modulates OSGPR114 or OSGPR78 activity.

The test agent may be contacted in step (i) with cells that express OSGPR114 or OSGPR78 or a variant thereof. Alternatively, the test agent may be contacted in step (i) with membranes obtained from such cells. In one embodiment, a modulator of OSGPR114 or OSGPR78 may be identified by determining the inhibition of binding of a ligand to cells which have the receptor on the surface thereof, or to cell membranes containing the receptor, in the presence of a candidate compound, under conditions to permit binding to the receptor, and determining the amount of ligand bound to the receptor, such that a compound capable of causing reduction of binding of a ligand is an agonist or antagonist, in which method the ligand is an LPA compound, including, but not limited to, myristoyl lysophosphatidic acid, oleoyl lysophosphatidic acid, palmitoyl lysophosphatidic acid, and stearoyl lysophosphatidic acid, or a functional analog or homolog of one of these compounds.

This invention thus provides a method of identifying a modulator of OSGPR114 or OSGPR78 activity, comprising (a) providing a OSGPR114 or OSGPR78 receptor, (b) incubating the OSGPR114 or OSGPR78 receptor with an test agent to be screened under conditions to permit binding of the test agent to the receptor; and (c) determining whether the test agent binds to, and activates, or inhibits, the receptor, by detecting the presence or absence of a signal generated from the interaction of the agent with the receptor, and thereby determining whether the test agent modulates OSGPR114 or OSGPR78 activity.

This invention thus also provides a method of identifying a modulator of OSGPR114 or OSGPR78, comprising (a) providing a cell expressing on its surface the receptor OSGPR114 or OSGPR78, said receptor being associated with a second component capable of providing a detectable signal in response to the binding of an agent to said receptor, (b) contacting with an test agent to be screened under conditions to permit binding to the receptor; and (c) determining whether the agent binds to, and activates, or inhibits, the receptor, by detecting the presence or absence of a signal generated from the interaction of the compound with the receptor and thereby determining whether the test agent modulates OSGPR114 or OSGPR78 activity.

This invention further provides the above methods wherein the step of incubating or contacting with the test agent (step b) is carried out in combination with (i.e. in the presence of; or by also contacting the cells with) a ligand for the OSGPR114 or OSGPR78 receptor, in which method the ligand is an LPA, including, but not limited to, myristoyl lysophosphatidic acid, oleoyl lysophosphatidic acid, palmitoyl lysophosphatidic acid, and stearoyl lysophosphatidic acid, or a functional analog or homolog of one of these compounds.

In the practice of this invention the OSGPR114 or OSGPR78 receptor can be from any species, or a functional variant thereof, as described herein. In one embodiment, the OSGPR114 or OSGPR78 receptor is selected from human, mammalian, rodent, murine, rat, dog, rabbit and monkey receptors. The cells of this invention can be any cells expressing OSGPR114 or OSGPR78 receptor or a functional variant thereof. Suitable cells are colon, lung, ovarian, breast, prostate, pancreas, esophagus, kidney, stomach, glioma, leukocyte, lymphocyte, melanocyte, and adipocyte cells, or cells where the OSGPR114 or OSGPR78 receptor expressed by the cell is a recombinant receptor, including CHO, CHO-K1, RH7777, Jurkat, HCT4, RBL243, HeLa, ASPC-1, HEK-293, and COS7 cells.

Cells can be provided as a differentiated cell line, or can be primary cells harvested from a human or animal donor. In the methods of this invention, where the OSGPR114 or OSGPR78 is associated with a second component capable of providing a detectable signal, that second component may be a G-protein, for example a Gi or a Go-protein, or a G-protein with a promiscuous G-alpha subunit (e.g. $G_{16}$, $G_{15}$). In an alternative embodiment that second component may be a Gs, Gq or $G_{12-13}$ protein. In a further embodiment the second component can be β-arrestin. In one embodiment, where OSGPR114 is associated with a second component capable of providing a detectable signal, that second component is a Gi-protein or a Go-protein. In one embodiment, where OSGPR78 is associated with a second component capable of providing a detectable signal, that second component is a Gs-protein.

The invention also provides a test kit suitable for identification of an agent that modulates OSGPR114 or OSGPR78 activity, which kit comprises (a) OSGPR114 or OSGPR78 or a variant thereof which is capable of coupling to a G-protein; and (b) means for monitoring OSGPR114 or OSGPR78 activity. The G-protein may be selected from Gi, Go, $G_{16}$, $G_{15}$, Gs, Gq and $G_{12-13}$, or any other G-protein that is activated by OSGPR114 or OSGPR78 under the conditions employed in the test kit. In one embodiment, component (a) comprises cells which express OSGPR114 or OSGPR78, or a variant thereof. In one embodiment the means for monitoring OSGPR114 or OSGPR78 activity of component (b) is an assay system for monitoring a signal transduction pathway or cellular activity activated by the coupling of OSGPR114 or OSGPR78 or a variant thereof to a G-protein. Several such assay systems are described herein, or are well known by one of ordinary skill in the art. In one embodiment component (b) comprises a means for determining whether Gi/o is activated.

This invention also provides a method for identification of an agent that modulates a cellular activity regulated by activation of OSGPR114 or OSGPR78 in a cell, which method comprises contacting a test cell with a test agent that modulates OSGPR114 or OSGPR78 activity, and which has been identified by the method of the invention (e.g. an assay method or process described herein), monitoring a change in the cellular activity, and thereby determining whether the test substance is a modulator of the cellular activity. This method can also be performed where the step of contacting a test cell with a test agent is carried out in combination with a ligand for the OSGPR114 or OSGPR78 receptor. The invention further provides this method but wherein the test agent is not known to modulate OSGPR114 or OSGPR78 activity, and wherein the step of contacting a test cell with a test agent is carried out in combination with a ligand for the OSGPR114 or OSGPR78 receptor. In these methods the ligand is an LPA compound, including, but not limited to, myristoyl lysophosphatidic acid, oleoyl lysophosphatidic acid, palmitoyl lysophosphatidic acid, and stearoyl lysophosphatidic acid, or a functional analog or homolog of one of these compounds. Competition of the test agent with the ligand will identify agents (e.g. antagonists, reverse agonists) that can modulate regulation of the cellular activity by the ligand.

In the preceding methods for identification of an agent that modulates a cellular activity regulated by activation of OSGPR114 or OSGPR78 in a cell, the cellular activity can be, but is not limited to, cell proliferation, apoptosis, anoikis (in endothelial or epithelial cells), proangiogenic factor secretion, cell invasion, cell motility, chemotaxis, insulin secretion, ion flux across cell membranes (e.g. $Ca^{2+}$, $K^+$, $Na^+$), cellular aggregation, closure of gap junctions, neurite retraction, changes in cytoskeletal architecture, ERK activation, c-fos gene induction, cellular LPA production, metalloproteinase activity (e.g. MMP2, MMP9), urokinase plasminogen activator (uPA) production, urokinase plasminogen activator activity, lipid metabolism, storage or transport, and glucose metabolism or transport. In one embodiment the cell is a colon, lung, ovarian, breast, prostate, pancreas, esophagus, kidney, stomach, glioma, leukocyte, lymphocyte, or melanocyte cell. In an alternative embodiment the cell is an adipocyte, a pancreatic cell, a renal cell, a hepatocyte, or a skeletal muscle cell.

This invention also provides a method for identification of an agent that inhibits tumor growth, which method comprises contacting a test subject with a test agent which modulates OSGPR114 or OSGPR78 activity, and monitoring tumor growth, thereby determining whether the test substance is an inhibitor of tumor growth.

This invention also provides a method for identification of an agent that inhibits tumor growth, which method comprises contacting a test subject with a test agent which inhibits LPA-activated OSGPR114 or OSGPR78 activity, and monitoring tumor growth or tumor size, thereby determining whether the test substance is an inhibitor of tumor growth.

This invention also provides a method for identification of an agent that inhibits cell proliferation, which method comprises contacting a cell with a test agent which modulates OSGPR114 or OSGPR78 activity, and monitoring cell proliferation, thereby determining whether the test substance is an inhibitor of cell proliferation.

This invention also provides a method for identification of an agent that inhibits cell proliferation, which method comprises contacting a cell with a test agent which inhibits LPA-activated OSGPR114 or OSGPR78 activity, and monitoring cell proliferation, thereby determining whether the test substance is an inhibitor of cell proliferation.

This invention also provides a method for identification of an agent that stimulates cell proliferation, which method comprises contacting a cell with a test agent which modulates OSGPR114 or OSGPR78 activity, and monitoring cell proliferation, thereby determining whether the test substance is a stimulator of cell proliferation.

This invention also provides a method for identification of an agent that stimulates cell proliferation, which method comprises contacting a cell with a test agent which further activates or enhances LPA-activated OSGPR114 or OSGPR78 activity, and monitoring cell proliferation, thereby determining whether the test substance is a stimulator of cell proliferation. An example of a test substance that would further activate or enhance LPA-activated OSGPR114 or OSGPR78 activity would be an allosteric agonist.

This invention also provides a method for identification of an agent that inhibits tumor growth, which method comprises contacting a test subject with a test agent which modulates OSGPR114 or OSGPR78 activity, and which has been identified by any method or process of the invention, and monitoring tumor growth or tumor size, thereby determining whether the test substance is an inhibitor of tumor growth.

This invention also provides a method for identification of an agent that inhibits tumor growth, which method comprises contacting a test subject with a test agent which inhibits LPA-activated OSGPR114 or OSGPR78 activity, and which has been identified by any method or process of the invention, and monitoring tumor growth or tumor size, thereby determining whether the test substance is an inhibitor of tumor growth.

This invention also provides a method for identification of an agent that inhibits cell proliferation, which method comprises contacting a cell with a test agent which modulates OSGPR114 or OSGPR78 activity, and which has been identified by any method or process of the invention, and monitoring cell proliferation, thereby determining whether the test substance is an inhibitor of cell proliferation.

This invention also provides a method for identification of an agent that inhibits cell proliferation, which method comprises contacting a cell with a test agent which inhibits LPA-activated OSGPR114 or OSGPR78 activity, and which has been identified by any method or process of the invention, and monitoring cell proliferation, thereby determining whether the test substance is an inhibitor of cell proliferation.

This invention also provides a method for identification of an agent that stimulates cell proliferation, which method comprises contacting a cell with a test agent which modulates OSGPR114 or OSGPR78 activity, and which has been identified by any method or process of the invention, and monitoring cell proliferation, thereby determining whether the test substance is a stimulator of cell proliferation.

This invention also provides a method for identification of an agent that stimulates cell proliferation, which method comprises contacting a cell with a test agent which further activates or enhances LPA-activated OSGPR114 or OSGPR78 activity, and which has been identified by any method or process of the invention, and monitoring cell proliferation, thereby determining whether the test substance is a stimulator of cell proliferation. An example of a test substance that would further activate or enhance LPA-activated OSGPR114 or OSGPR78 activity would be an allosteric agonist.

This invention also provides a method for identification of an agent that causes an activation of cell apoptosis, which method comprises contacting a cell with a test agent which modulates OSGPR114 or OSGPR78 activity, identified by any method or process of the invention, and monitoring cell apoptosis, thereby determining whether the test agent is an activator of apoptosis.

This invention also provides a method for identification of an agent that causes an inhibition of cell apoptosis, which method comprises contacting a cell with a test agent which modulates OSGPR114 or OSGPR78 activity, identified by any method or process of the invention, and monitoring cell apoptosis, thereby determining whether the test agent is an inhibitor of apoptosis.

This invention also provides a method for identification of an agent that causes a reduction in cell motility, which method comprises contacting a cell with a test agent which modulates OSGPR114 or OSGPR78 activity, identified by any method or process of the invention, and monitoring cell motility, thereby determining whether the test agent is an inhibitor of cell motility.

This invention also provides a method for identification of an agent that causes an increase in cell motility, which method comprises contacting a cell with a test agent which modulates OSGPR114 or OSGPR78 activity, identified by any method or process of the invention, and monitoring cell motility, thereby determining whether the test agent is an activator of cell motility.

This invention also provides a method for identification of an agent that causes a reduction in cell invasion, which method comprises contacting a cell with a test agent which modulates OSGPR114 or OSGPR78 activity, identified by any method or process of the invention, and monitoring cell invasion, thereby determining whether the test agent is an inhibitor of cell invasion.

This invention also provides a method for identification of an agent that causes an increase in cell invasion, which method comprises contacting a cell with a test agent which modulates OSGPR114 or OSGPR78 activity, identified by any method or process of the invention, and monitoring cell invasion, thereby determining whether the test agent is an stimulator of cell invasion.

This invention also provides a method for identification of an agent that causes an increase in proangiogenic factor secretion from cells, which method comprises contacting a cell with a test agent which modulates OSGPR114 or OSGPR78 activity, identified by any method or process of the invention, and monitoring proangiogenic factor secretion, thereby determining whether the test agent is an activator of proangiogenic factor secretion.

This invention also provides a method for identification of an agent that causes a decrease in proangiogenic factor secretion from cells, which method comprises contacting a cell with a test agent which modulates OSGPR114 or OSGPR78 activity, identified by any method or process of the invention, and monitoring proangiogenic factor secretion, thereby determining whether the test agent is an inhibitor of proangiogenic factor secretion.

This invention also provides a method for identification of an agent that causes an activation of cell apoptosis in a subject, which method comprises contacting a subject with a test agent which modulates OSGPR114 or OSGPR78 activity, identified by any method or process of the invention, and monitoring cell apoptosis, thereby determining whether the test agent is an activator of apoptosis.

This invention also provides a method for identification of an agent that causes an inhibition of cell apoptosis in a subject, which method comprises contacting a subject with a test agent which modulates OSGPR114 or OSGPR78 activity, identified by any method or process of the invention, and monitoring cell apoptosis, thereby determining whether the test agent is an inhibitor of apoptosis.

This invention also provides a method for identification of an agent that causes a reduction in cell motility in a subject, which method comprises contacting a subject with a test agent which modulates OSGPR114 or OSGPR78 activity, identified by any method or process of the invention, and monitoring cell motility, thereby determining whether the test agent is an inhibitor of cell motility.

This invention also provides a method for identification of an agent that causes a increase in cell motility in a subject, which method comprises contacting a subject with a test agent which modulates OSGPR114 or OSGPR78 activity, identified by any method or process of the invention, and monitoring cell motility, thereby determining whether the test agent is an activator of cell motility.

This invention also provides a method for identification of an agent that causes a reduction in cell invasion in a subject, which method comprises contacting a subject with a test agent which modulates OSGPR114 or OSGPR78 activity, identified by any method or process of the invention, and monitoring cell invasion, thereby determining whether the test agent is an inhibitor of cell invasion.

This invention also provides a method for identification of an agent that causes a increase in cell invasion in a subject, which method comprises contacting a subject with a test agent which modulates OSGPR114 or OSGPR78 activity, identified by any method or process of the invention, and monitoring cell invasion, thereby determining whether the test agent is an stimulator of cell invasion.

This invention also provides a method for identification of an agent that causes a increase in proangiogenic factor secretion from cells in a subject, which method comprises contacting a subject with a test agent which modulates OSGPR114 or OSGPR78 activity, identified by any method or process of the invention, and monitoring proangiogenic factor secretion, thereby determining whether the test agent is an activator of proangiogenic factor secretion.

This invention also provides a method for identification of an agent that causes a decrease in proangiogenic factor secretion from cells in a subject, which method comprises contacting a subject with a test agent which modulates OSGPR114 or OSGPR78 activity, identified by any method or process of the invention, and monitoring proangiogenic factor secretion, thereby determining whether the test agent is an inhibitor of proangiogenic factor secretion.

This invention also provides a method for identification of an agent that causes a reduction in angiogenesis in a subject, which method comprises contacting a subject with a test agent which modulates OSGPR114 or OSGPR78 activity, identified by any method or process of the invention, and monitoring angiogenesis, thereby determining whether the test agent is an inhibitor of angiogenesis.

This invention also provides a method for identification of an agent that causes a increase in angiogenesis in a subject, which method comprises contacting a subject with a test agent which modulates OSGPR114 or OSGPR78 activity, identified by any method or process of the invention, and monitoring angiogenesis, thereby determining whether the test agent is an activator of angiogenesis.

This invention also provides a method for identification of an agent that causes a reduction in metastasis in a subject, which method comprises contacting a subject with a test agent which modulates OSGPR114 or OSGPR78 activity, identified by any method or process of the invention, and monitoring metastasis, thereby determining whether the test agent is an inhibitor of metastasis.

In all the preceding methods for identification of agents, the test agent can be an antagonist, an inverse agonist, a partial inverse agonist, an allosteric or allotopic antagonist, an agonist, a partial agonist, or an allosteric or allotopic agonist.

This invention also provides any of the above methods involving contacting a cell, wherein the cell is a colon, lung, ovarian, breast, prostate, pancreas, esophagus, kidney, stomach, glioma, leukocyte, lymphocyte, melanocyte, or adipocyte cell.

This invention also provides any of the above methods for identification of an agent that inhibits tumor growth, wherein the tumor is a colon, lung, cervical, ovarian, endometrial, breast, prostate, pancreas, esophagus, kidney, stomach, glioma, myeloma or melanoma tumor.

This invention also provides a modulator of OSGPR114 or OSGPR78 activity, or a modulator of cell proliferation or tumor growth, identified by a method of the invention, and their use in therapy and pharmaceutical compositions comprising them.

This invention also provides a method of inhibiting tumor growth in a mammal in recognized need of such treatment, said method comprising administering to said mammal in recognized need of such treatment, an antagonist or inverse agonist of OSGPR114 or OSGPR78 activity, wherein said administering is in an effective amount to inhibit tumor growth in said mammal.

This invention also provides a method of inhibiting tumor growth in a mammal in recognized need of such treatment, said method comprising administering to said mammal in recognized need of such treatment, an antagonist of the LPA-dependent or LPA-activated activity of OSGPR114 or OSGPR78, wherein said administering is in an effective amount to inhibit tumor growth in said mammal.

In the above methods of inhibiting tumor growth, the antagonist may be a small molecule that competes with the LPA ligand on the OSGPR114 or OSGPR78 receptor. Alternatively, the antagonist may be an agent that reduces the level of OSGPR114 or OSGPR78 receptor protein in the tumor cells, e.g. an antisense molecule, or a small inhibitory RNA (i.e. RNA interference). Methods for designing and using effective molecules of this type for genes whose sequence is known are well known in the art, as described in references cited herein (see p. 33-34).

This invention also provides a method of inhibiting tumor growth in a mammal in recognized need of such treatment, said method comprising administering to said mammal in recognized need of such treatment, an agonist or allosteric agonist of an LPA-activated mammalian OSGPR114 or OSGPR78 receptor, wherein said administering is in an effective amount to reduce tumor growth in said mammal.

In one embodiment of the preceding methods the tumor is a colon, lung, cervical, ovarian, endometrial, breast, prostate, pancreas, esophagus, kidney, stomach, glioma, myeloma or melanoma tumor.

This invention also provides a method of reducing abnormal cell growth or abnormal cell proliferation in a mammal in recognized need of such treatment, said method comprising administering to said mammal in recognized need of such treatment, an antagonist of an LPA-activated mammalian OSGPR114 or OSGPR78 receptor, wherein said administering is in an effective amount to reduce abnormal cell growth in said mammal. In one embodiment of this method the cell is a colon, lung, ovarian, breast, prostate, cervical, pancreas, esophagus, kidney, stomach, glioma, leukocyte, lymphocyte, or melanocyte cell.

"Abnormal cell growth" or "abnormal cell proliferation", as used herein, refers to cell growth that is independent of normal regulatory mechanisms (e.g. as relected by loss of contact inhibition of cells grown in culture in vitro), including the abnormal growth of normal cells and the growth of abnormal cells. This includes, but is not limited to, the abnormal growth of tumor cells (tumors), both benign and malignant, and the growth of cells in diseases associated with benign cell proliferation, e.g. atherosclerosis, restenosis.

This invention also provides a method of stimulating apoptosis of cells in a mammal in recognized need of such treatment, said method comprising administering to said mammal in recognized need of such treatment, an antagonist of an LPA-activated mammalian OSGPR114 or OSGPR78 receptor, wherein said administering is in an effective amount to stimulate apoptosis in said mammal. In one embodiment of this method the cells are colon, lung, ovarian, breast, prostate, pancreas, esophagus, kidney, stomach, glioma, leukocyte, lymphocyte, or melanocyte cells.

This invention also provides a method of inhibiting angiogenesis in a mammal in recognized need of such treatment, said method comprising administering to said mammal in recognized need of such treatment, an antagonist of an LPA-activated mammalian OSGPR114 or OSGPR78 receptor, wherein said administering is in an effective amount to inhibit angiogenesis in said mammal.

This invention also provides a method of stimulating angiogenesis in a mammal in recognized need of such treatment, said method comprising administering to said mammal in recognized need of such treatment, an agonist of a mammalian OSGPR114 or OSGPR78 receptor, wherein said administering is in an effective amount to stimulate angiogenesis in said mammal.

This invention also provides a method of inhibiting metastasis in a mammal in recognized need of such treatment, said method comprising administering to said mammal in recognized need of such treatment, an antagonist of an LPA-activated mammalian OSGPR114 or OSGPR78 receptor, wherein said administering is in an effective amount to inhibit metastasis in said mammal.

In the above methods of reducing abnormal cell growth or abnormal cell proliferation, stimulating angiogenesis, or inhibiting metastasis, the antagonist may be a small molecule that competes with the LPA ligand on the OSGPR114 or OSGPR78 receptor. Alternatively, the antagonist may be an agent that reduces the level of OSGPR114 or OSGPR78 receptor protein in the tumor cells, e.g. an antisense molecule, or a small inhibitory RNA (i.e. RNA interference). Methods for designing and using effective molecules of this type for genes whose sequence is known are well known in the art, as described in references cited herein (see p. 33-34).

This invention also provides a modulator (e.g. an activator or an inhibitor) of OSGPR114 or OSGPR78 activity, or a modulator (e.g. an activator or an inhibitor) of cell proliferation or tumor growth, identified by a method of the invention, or a polynucleotide which encodes OSGPR114 or OSGPR78 or a variant polypeptide, for use in a method of treatment of the human or animal body by therapy; and use of such a modulator (e.g. activator, inhibitor) or polynucleotide in the manufacture of a medicament for the treatment of diseases or conditions modulated by OSGPR114 or OSGPR78, for example, cancer, obesity, certain diseases of the cardiovascular and respiratory systems, including artherosclerosis, restenosis and acetylcholine induced airway hyperresponsiveness, wound healing, reproductive function, abnormal immune system regulation, abnormalities in neuronal growth, survival and signaling, and renal failure associated with renal ischemia.

This invention also provides an inhibitor of cell proliferation, apoptosis, cell motility, cell invasion, proangiogenic factor secretion, angiogenesis, tumor growth, or metastasis identified by a method of this invention. This invention further provides the use of the inhibitor in the manufacture of a medicament for the treatment of abnormal cell proliferation or cancer. In one embodiment the inhibitor of proliferation, apoptosis, cell motility, cell invasion, proangiogenic factor secretion, angiogenesis, tumor growth, or metastasis is for use in the treatment of abnormal cell proliferation or cancer. In one embodiment the abnormal cell proliferation or cancer is selected from cancers of the colon, lung, ovarian, breast, prostate, pancreas, esophagus, kidney, and stomach, and glioma, leukemia, lymphoma, and melanoma.

This invention also provides an activator of cell proliferation, apoptosis, cell motility, cell invasion, proangiogenic factor secretion, or angiogenesis identified by a method of this invention. This invention further provides the use of the activator in the manufacture of a medicament for the treatment of abnormal cell proliferation or cancer. In one embodiment the activator of apoptosis is for use in the treatment of abnormal cell proliferation or cancer. In one embodiment the abnormal cell proliferation or cancer is selected from cancers of the colon, lung, ovarian, breast, prostate, pancreas, esophagus, kidney, and stomach, and glioma, leukemia, lymphoma, and melanoma.

This invention further provides the use of a modulator of OSGPR114 or OSGPR78 for the manufacture of a medicament for the treatment of OSGPR114 or OSGPR78 mediated diseases. In one embodiment the OSGPR114 or OSGPR78 mediated disease is selected from cancers of the colon, lung, ovarian, breast, prostate, pancreas, esophagus, kidney, and stomach, and glioma, leukemia, lymphoma, and melanoma.

The invention also provides a method of treating OSGPR114 or OSGPR78 mediated disease in an individual which comprises administering to the individual a therapeutic amount of a modulator of OSGPR114 or OSGPR78 activity. In one embodiment the OSGPR114 or OSGPR78 mediated disease is selected from cancers of the colon, lung, ovarian, breast, prostate, pancreas, esophagus, kidney, and stomach, and glioma, leukemia, lymphoma, and melanoma.

This invention further provides a method of treating an OSGPR114 or OSGPR78 mediated disease in an individual which comprises administering to the individual a therapeutic amount of a modulator of OSGPR114 in combination with a therapeutic amount of a modulator of OSGPR78 activity. In one embodiment the OSGPR114 or OSGPR78 mediated disease is selected from cancers of the colon, lung, ovarian, breast, prostate, pancreas, esophagus, kidney, and stomach, and glioma, leukemia, lymphoma, and melanoma.

This invention provides a method for inhibiting tumor growth that is modulated by the LPA-activated activity of the OSGPR114 or OSGPR78 receptor, the method comprising reducing the LPA-activated activity of OSGPR114 or OSGPR78 in the tumor such that tumor growth is inhibited.

In one embodiment of this method for inhibiting tumor growth, the tumor is selected from a colon, lung, ovarian, breast, prostate, pancreas, esophagus, kidney, stomach, glioma, or melanoma tumor.

This invention provides a method for inhibiting angiogenesis in a subject that is modulated by the LPA-activated activity of the OSGPR114 or OSGPR78 receptor, the method comprising reducing the LPA-activated activity of OSGPR114 or OSGPR78 in the subject such that angiogenesis is inhibited.

This invention provides a method for inhibiting metastasis in a subject that is modulated by the LPA-activated activity of the OSGPR114 or OSGPR78 receptor, the method comprising reducing the LPA-activated activity of OSGPR114 or OSGPR78 in the subject such that metastasis is inhibited.

This invention provides a method for inhibiting a cellular activity that is modulated by the LPA-activated activity of the OSGPR114 or OSGPR78 receptor, the method comprising reducing the LPA-activated activity of OSGPR114 or OSGPR78 in the cell such that the cellular activity is inhibited. The cellular activity includes, but is not limited to, cell proliferation, apoptosis, cell motility, cell invasion, and proangiogenic factor secretion.

In one embodiment of the above methods wherein the LPA-activated activity of OSGPR114 or OSGPR78 activity is reduced, the activity is reduced by contacting the tumor, subject or cell with a small molecule inhibitor (e.g. an antagonist) of the LPA-activated activity of OSGPR114 or OSGPR78. In another embodiment of the above methods wherein the LPA-activated activity of OSGPR114 or OSGPR78 activity is reduced, the activity is reduced by specifically inhibiting transcription or gene expression from the OSGPR114 or OSGPR78 gene. In one embodiment, gene expression can be reduced by contacting the tumor, subject or cell with a double stranded RNA (dsRNA), or a vector or construct causing the production of double stranded RNA, such that expression of the OSGPR114 or OSGPR78 receptor is specifically inhibited (i.e. RNA interference or RNAi). Methods for selecting an appropriate dsRNA or dsRNA-encoding vector are well known in the art for genes whose sequence is known (e.g. see Tuschi, T., et al. (1999) Genes Dev. 13(24):3191-3197; Elbashir, S. M. et al. (2001) Nature 411:494-498; Hannon, G. J. (2002) Nature 418:244-251; McManus, M. T. and Sharp, P. A. (2002) Nature Reviews Genetics 3:737-747; Bremmelkamp, T. R. et al. (2002) Science 296:550-553; U.S. Pat. No. 6,573,099; WO 01/36646; WO 99/32619; U.S. Pat. No. 6,506,559; WO 01/68836). In another embodiment, gene expression can be reduced by contacting the tumor, subject or cell with a specific small molecule inhibitor of transcription. Methods for identifying compounds that are specific modulators of transcription are well known in the art (e.g. U.S. Pat. No. 5,776,502, U.S. Pat. No. 5,665,543). In another embodiment, gene expression can be reduced by contacting the tumor, subject or cell with an antisense molecule. Methods for using antisense techniques for specifically inhibiting gene expression of genes whose sequence is known are also well known in the art (e.g. see U.S. Pat. Nos. 6,566,135; 6,566,131; 6,365,354; 6,410,323; 6,107,091; 6,046,321; and 5,981,732).

This invention provides a method for stimulating a cellular activity that is modulated by the LPA-activated activity of the OSGPR114 or OSGPR78 receptor, the method comprising increasing the LPA-activated activity of OSGPR114 or OSGPR78 in the cell such that the cellular activity is stimulated. The cellular activity includes, but is not limited to, cell proliferation, apoptosis, cell motility, cell invasion, and proangiogenic factor secretion.

In one embodiment of the above methods wherein the LPA-activated activity of OSGPR114 or OSGPR78 activity is stimulated, the activity is increased by contacting the tumor, subject or cell with a small molecule inhibitor (e.g. an agonist, an allosteric agonist) of the LPA-activated activity of OSGPR114 or OSGPR78, or the activity is increased by specifically stimulating transcription from the OSGPR114 or OSGPR78 gene.

In one embodiment of the above methods for stimulating a cellular activity that is modulated by the LPA-activated activity of the OSGPR114 or OSGPR78 receptor, the cell is a colon, lung, ovarian, breast, prostate, pancreas, esophagus, kidney, stomach, glioma, leukocyte, lymphocyte, or melanocyte cell. In an alternative embodiment the cell is an adipocyte, a pancreatic cell, a renal cell, a hepatocyte, or a skeletal muscle cell.

Figure 10:
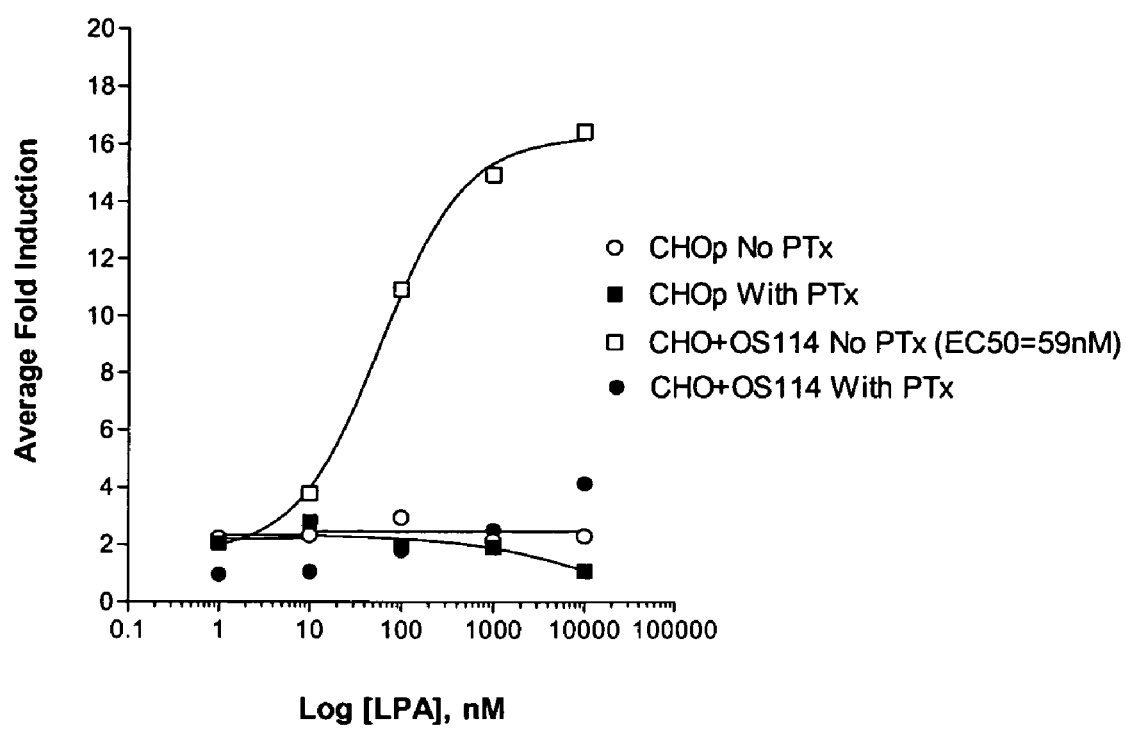
FIG. 10: Effects of LPA on intracellular calcium levels in CHO-K1 and CHO-OSGPR114 cells. The experiments were conducted in the presence and absence of pertussis toxin and as described in the Materials and Methods section.
Figure 14:
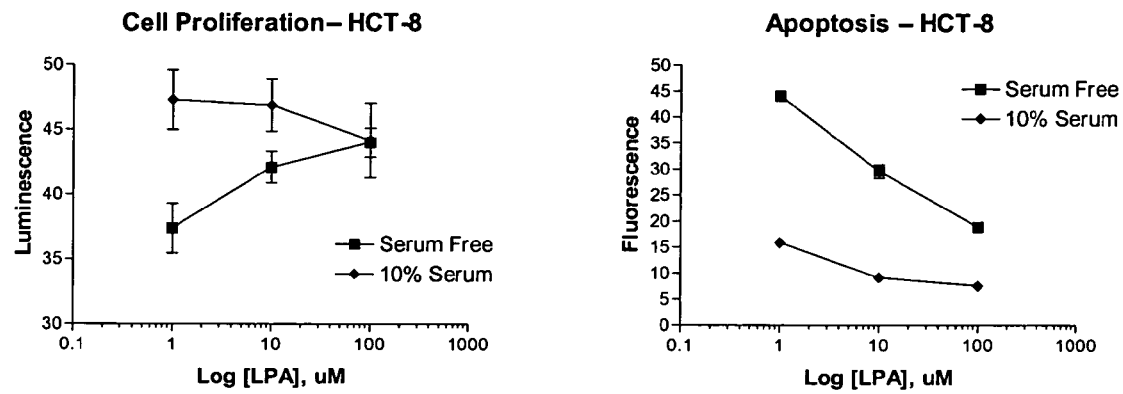
FIG. 14: Effect of LPA on proliferation and survival in HCT-8 cells in the presence and absence of serum. Data are means+/−s.e. calculated from two experiments conducted in triplicate. The y-axis units are a standardized expression of fluorescence or luminescence counts.
Figure 15:
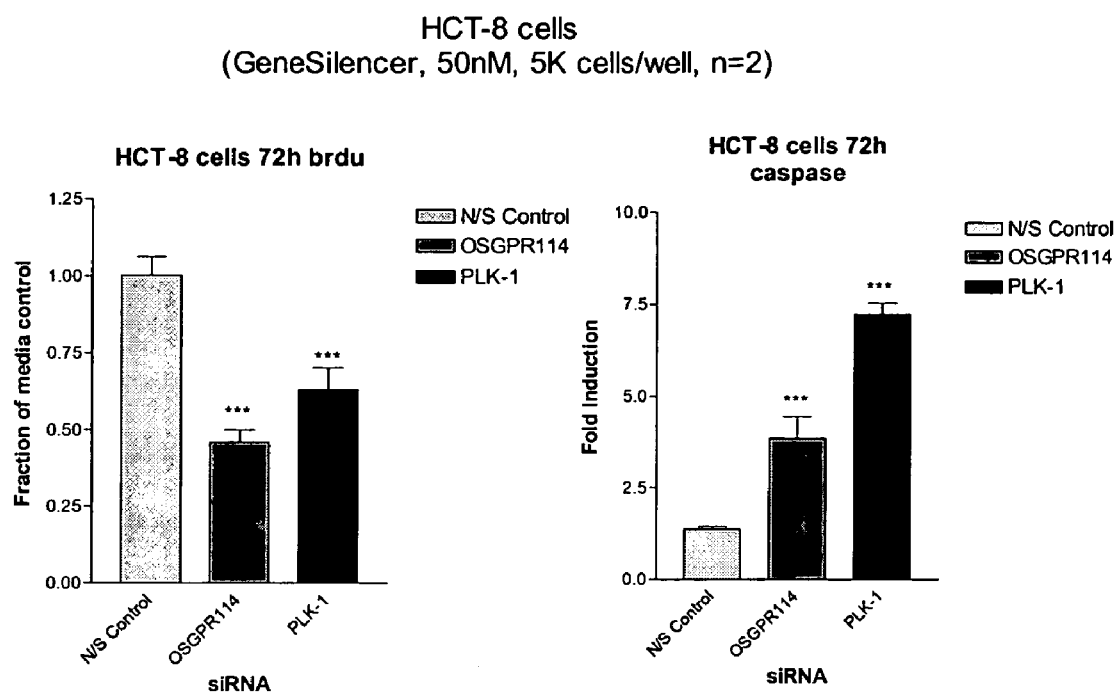
FIG. 15: Effect of transfection of non-specific, OSGPR114 and PLK1 siRNAs on HCT-8 cell proliferation and apoptosis as measured using BrDU and Apo-One caspase assays respectively. All data are normalized to cells not treated with siRNA, which was defined as equal to 1, and statistical comparisons (One-way ANOVA, Dunnett's post-hoc) were made between transfection of target genes and transfection of non-specific siRNA controls. Compared to non-specific siRNA, both OSGPR114 siRNA and the positive control PLK1 siRNA inhibited proliferation and induced apoptosis in HCT-8 cells 72 h after transfection.
Figure 16:
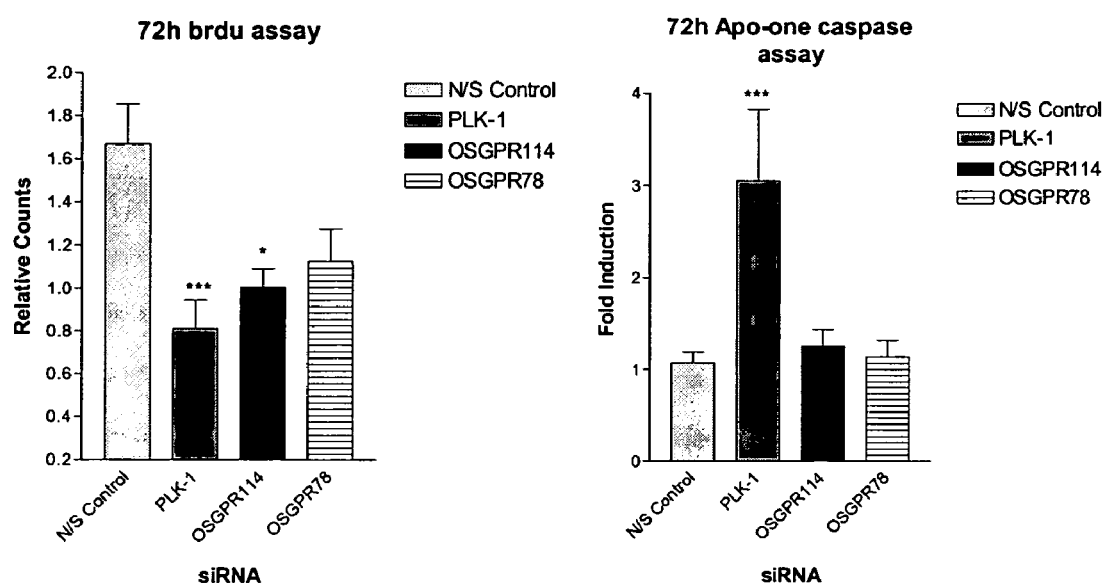
FIG. 16: Effect of transfection of non-specific, OSGPR114, OSGPR78 and PLK1 siRNAs on KLE cell proliferation and apoptosis as measured using BrDU and Apo-One caspase assays respectively. All data are normalized to cells not treated with siRNA, which was defined as equal to 1, and statistical comparisons (One-way ANOVA, Dunnett's post-hoc) were made between transfection of target genes and transfection of non-specific siRNA controls. Compared to non-specific siRNA, OSGPR114 siRNA and PLK1 significantly inhibited proliferation in KLE cells 72 h after transfection. OSGPR78 siRNA also inhibited proliferation in these cells although the difference was not significant statistically. Additionally PLK1 siRNA induced apoptosis of KLE cells whereas OSGPR114 and OSGPR78 had no statistical effect.
Figure 17:
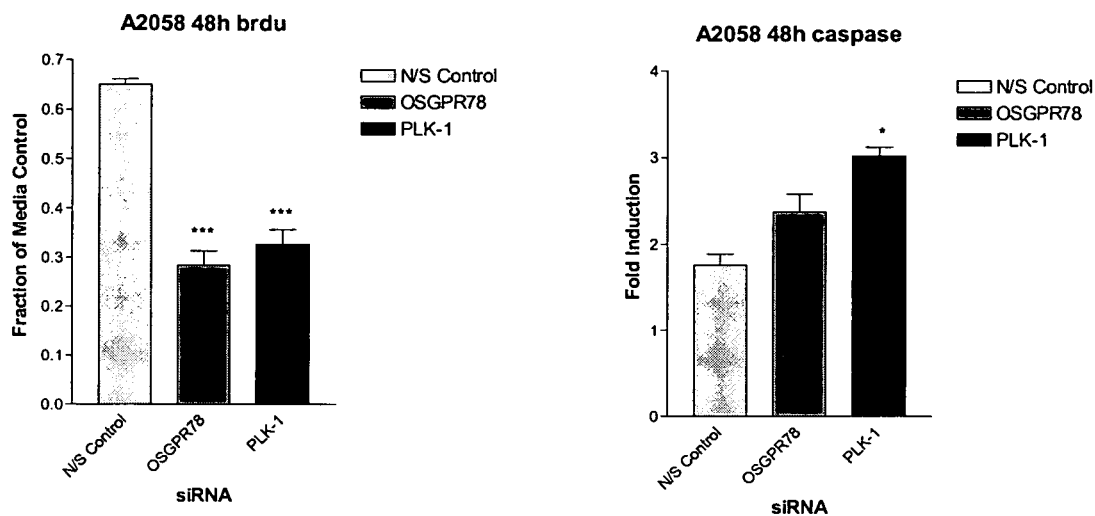
FIG. 17: Effect of transfection of non-specific, OSGPR78 and PLK1 siRNAs on A2058 cell proliferation and apoptosis as measured using BrDU and Apo-One caspase assays respectively. All data are normalized to cells not treated with siRNA, which was defined as equal to 1, and statistical comparisons (One-way ANOVA, Dunnett's post-hoc) were made between transfection of target genes and transfection of non-specific siRNA controls. Compared to non-specific siRNA, OSGPR78 and PLK1 siRNAs significantly inhibited proliferation in A2058 cells 48 h after transfection. Both siRNAs induced apoptosis though only PLK1 was significantly significant.
Figure 18:
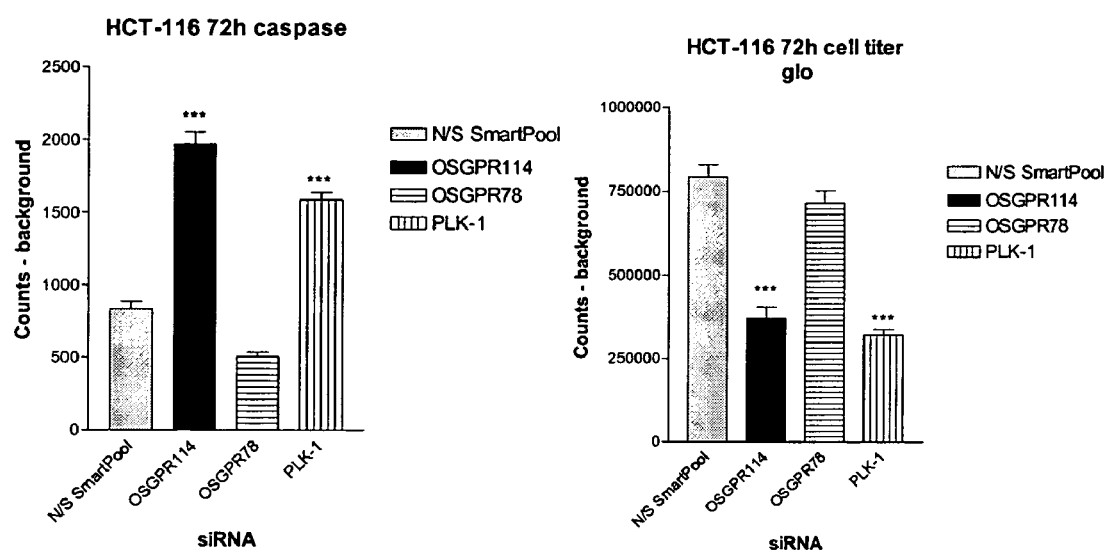
FIG. 18: Effect of transfection of non-specific, OSGPR114, OSGPR78 and PLK1 siRNAs on HCT-116 cell proliferation and apoptosis as measured using Cell-titer Glo and Apo-One caspase assays respectively. All data are normalized to cells not treated with siRNA, which was defined as equal to 1, and statistical comparisons (One-way ANOVA, Dunnett's post-hoc) were made between transfection of target genes and transfection of non-specific siRNA controls. Compared to non-specific siRNA, OSGPR114 and PLK1 siRNAs significantly inhibited proliferation and induced apoptosis in HCT-116 cells 72 h after transfection.
Figure 19:
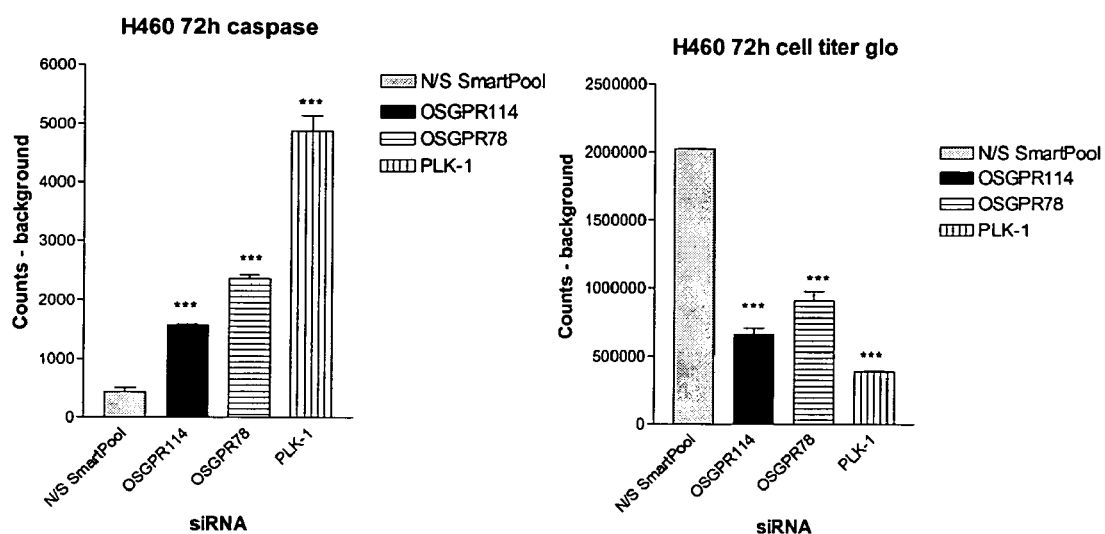
FIG. 19: Effect of transfection of non-specific, OSGPR114, OSGPR78 and PLK1 siRNAs on H460 cell proliferation and apoptosis as measured using Cell-titer Glo and Apo-One caspase assays respectively. All data are normalized to cells not treated with siRNA, which was defined as equal to 1, and statistical comparisons (One-way ANOVA, Dunnett's post-hoc) were made between transfection of target genes and transfection of non-specific siRNA controls. Compared to non-specific siRNA, OSGPR114, OSGPR78 and PLK1 siRNAs significantly inhibited proliferation and induced apoptosis in H460 cells 72 h after transfection.
Figure 20:
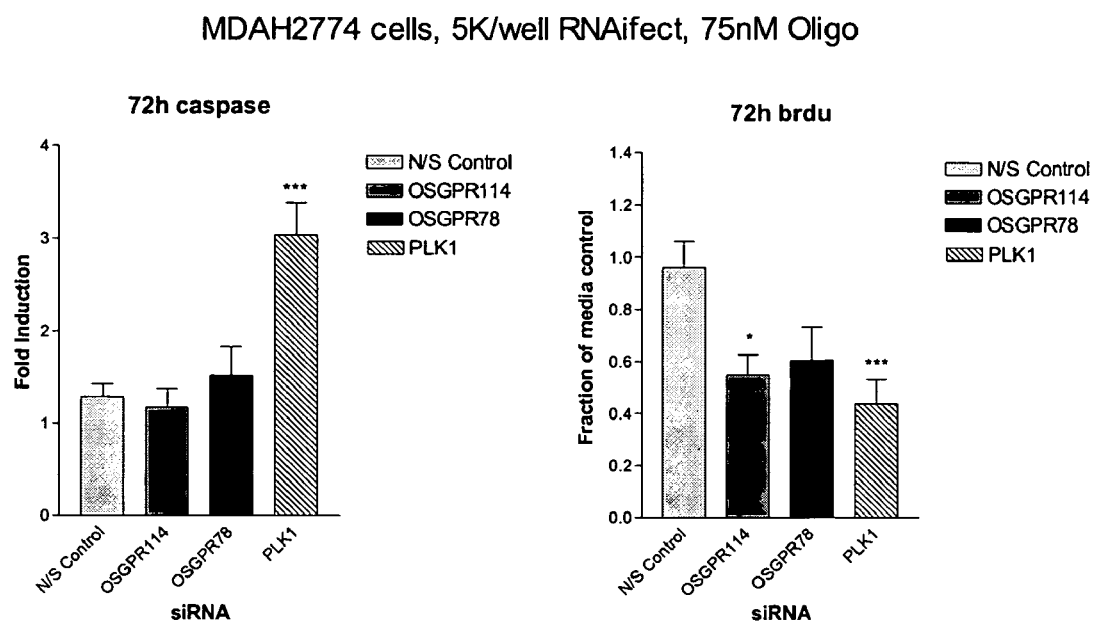
FIG. 20: Effect of transfection of non-specific, OSGPR114, OSGPR78 and PLK1 siRNAs on MDAH-2774 cell proliferation and apoptosis as measured using BrDU and Apo-One caspase assays respectively. All data are normalized to cells not treated with siRNA, which was defined as equal to 1, and statistical comparisons (One-way ANOVA, Dunnett's post-hoc) were made between transfection of target genes and transfection of non-specific siRNA controls. Compared to non-specific siRNA, OSGPR114, OSGPR78 and PLK1 siRNA inhibited proliferation in MDAH-2774 cells 72 h after transfection. The effect of OSGPR78 siRNA was not significant statistically.
Figure 21:
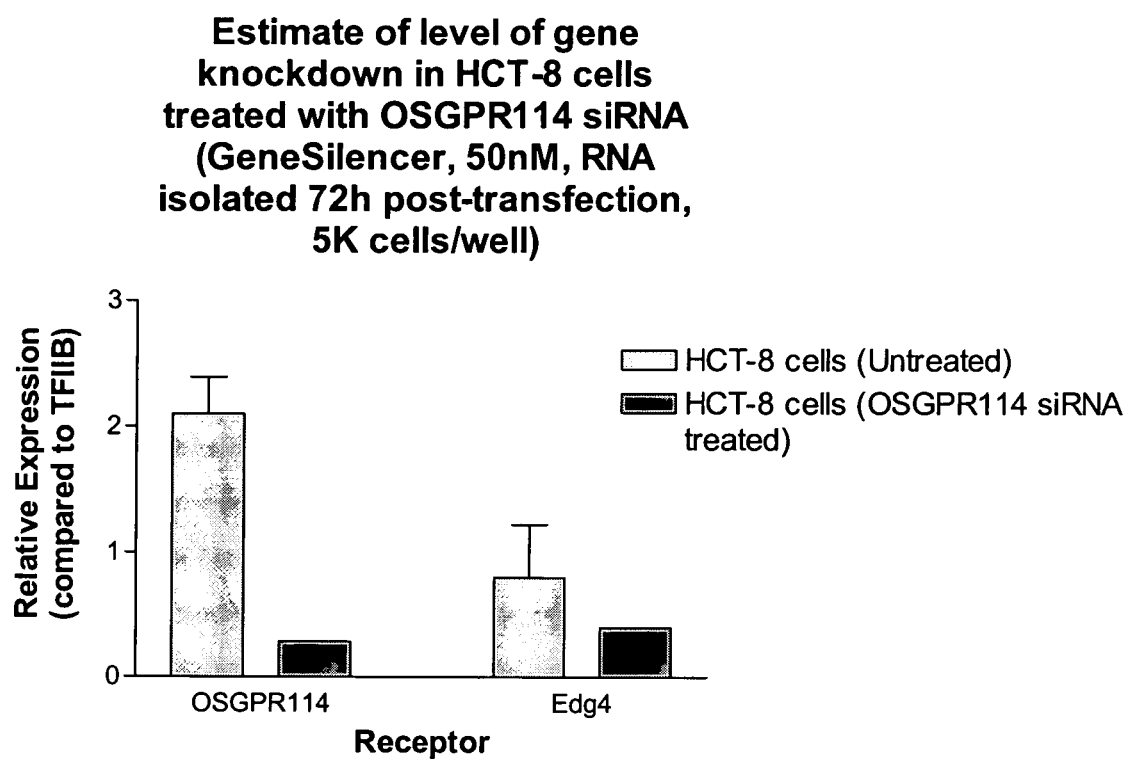
FIG. 21: Measurement of gene knockdown of OSGPR114 by OSGPR114 siRNA as measured by quantitative RT-PCR. OSGPR114 mRNA was reduced approximately 86% whereas Edg4, another LPA receptor expressed by HCT-8 cells was not significantly affected. Measurement of protein knockdown was not possible since an antibody for OSGPR114 does not presently exist. However, using an identical transfection protocol in HCT-8 cells, Lamin B2 siRNA reduced Lamin B2 protein by approximately 60% as measured by Western Blot analysis (Data not shown).
Figure 22:
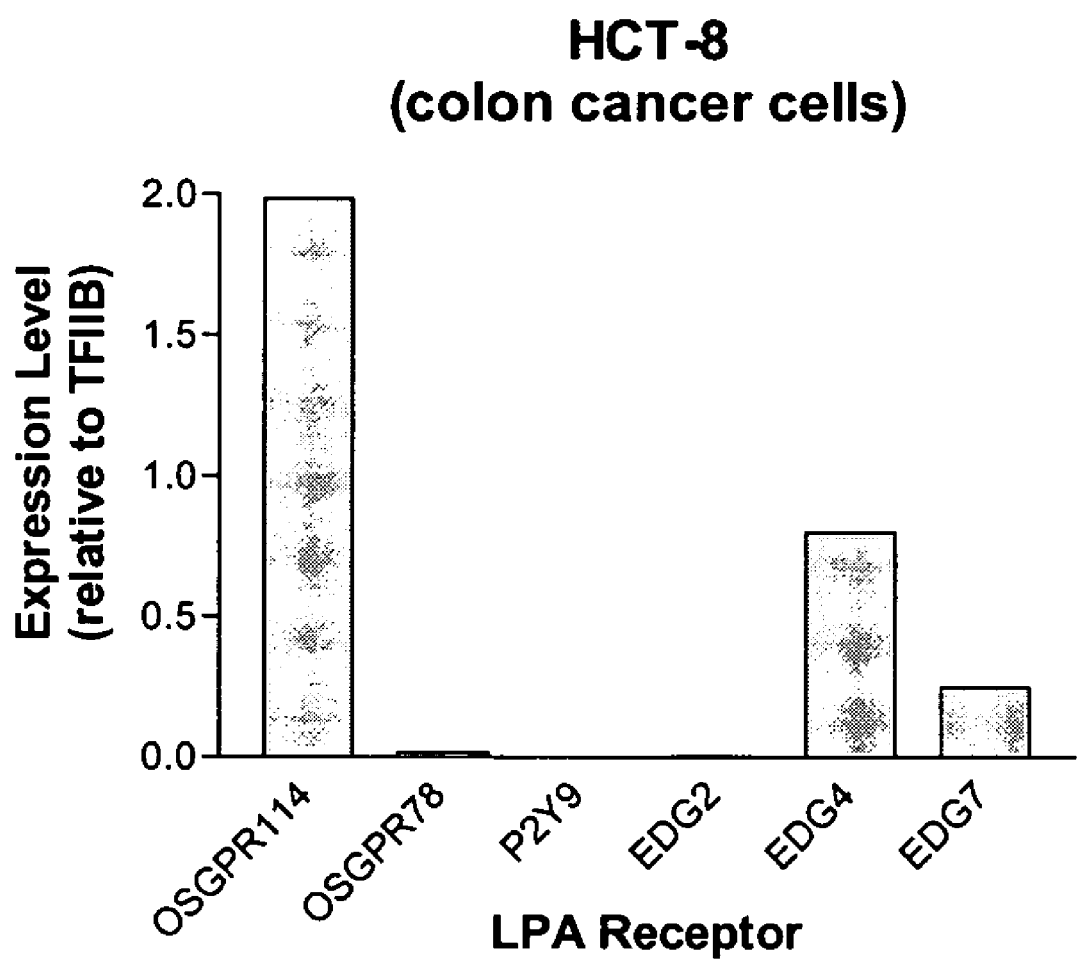
FIG. 22: Relative expression of LPA Receptors in HCT-8 cells. Data are expressed as a fraction of TFIIB levels using earlier defined methodologies.
Figure 23:
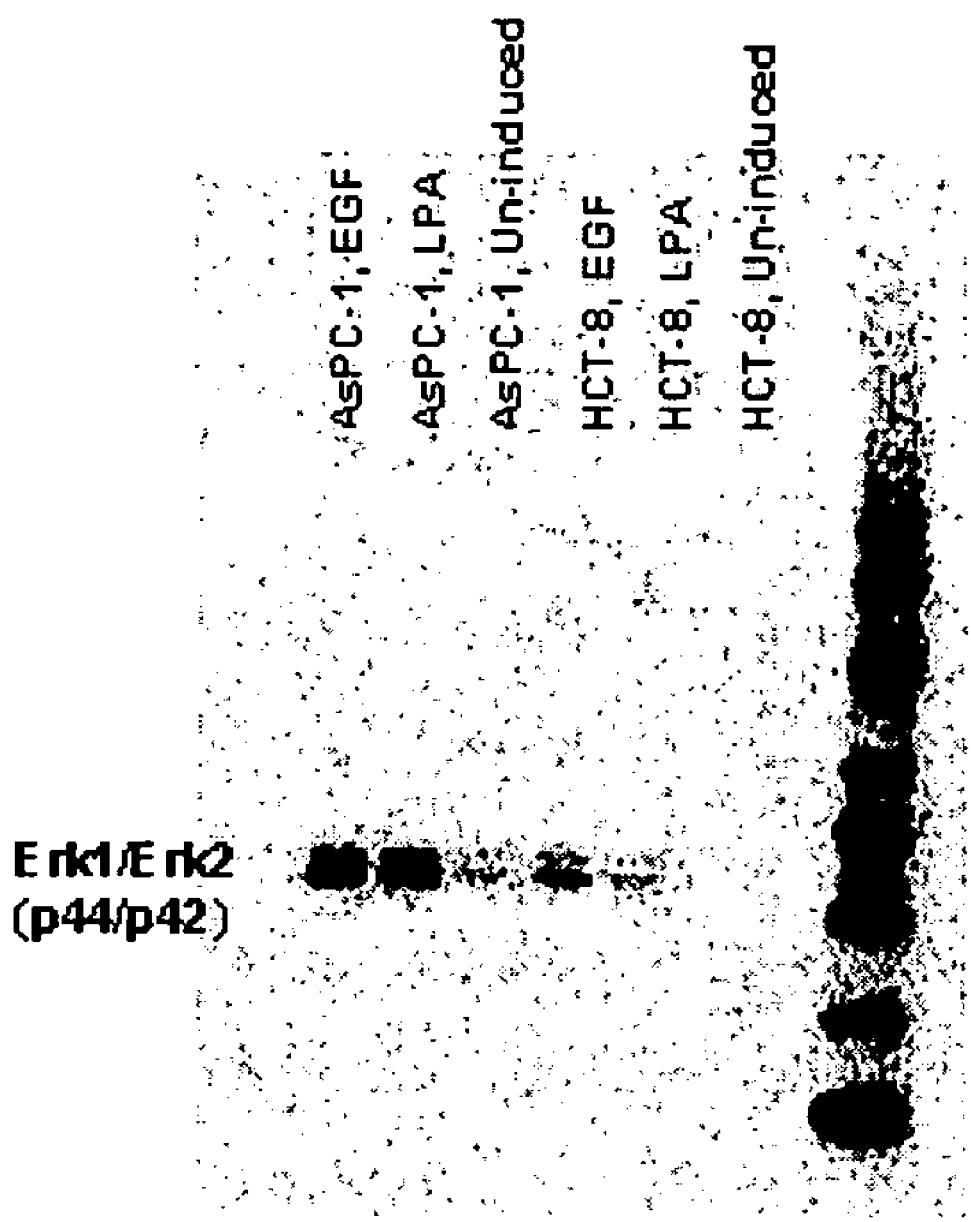
FIG. 23: Ability of LPA to phosphorylate ERK in cell lines known to express OSGPR114. 10 µM LPA and 1 µM EGF were used for this experiment, and the cells were stimulated with ligand for 3 mins prior to lysing.
Figure 24:
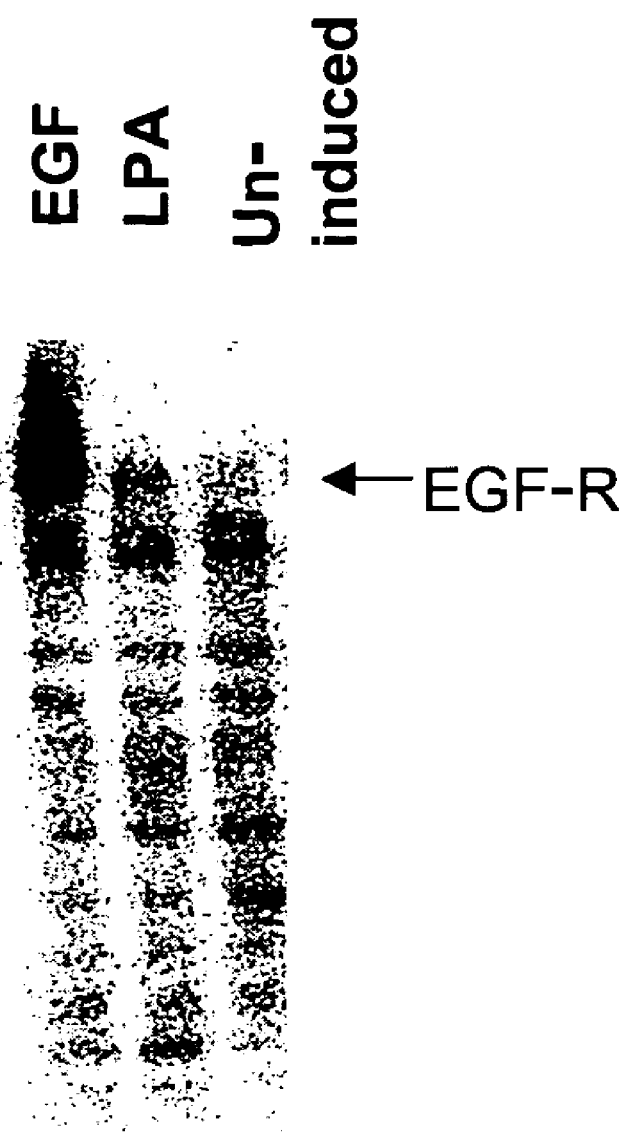
FIG. 24: Western blot showing the ability of LPA to transactivate EGFR in HCT-8 cells, as assessed using a phosphotyrosine specific antibody.
Figure 25:
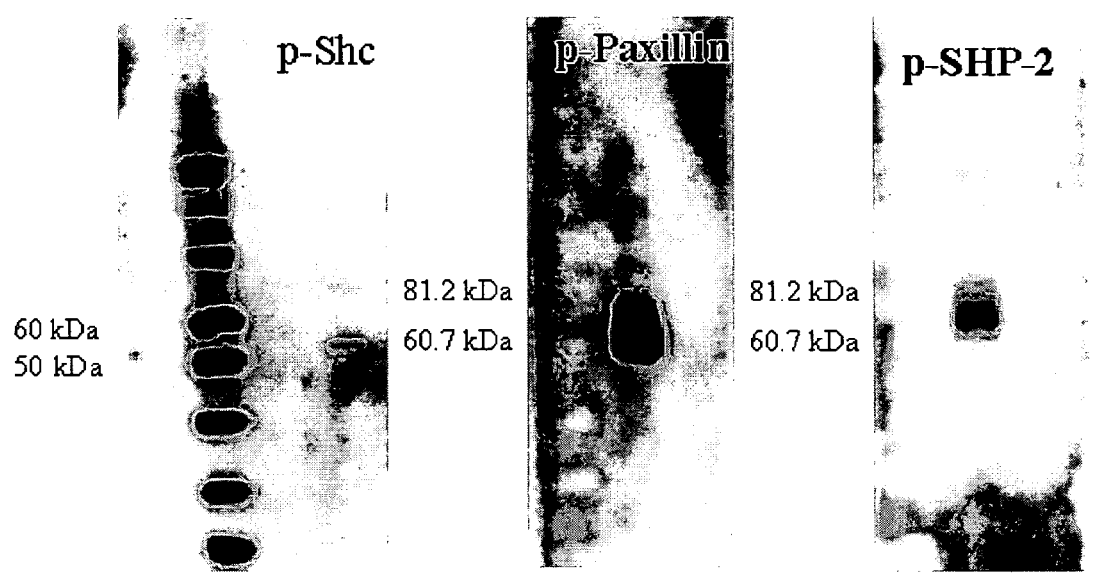
FIG. 25. LPA (10 uM) activation of Shc, paxillin and SHP-2 in HCT-8 cell lysates. Phospho-specific antibodies were used to detect the activated proteins.
Figure 26:
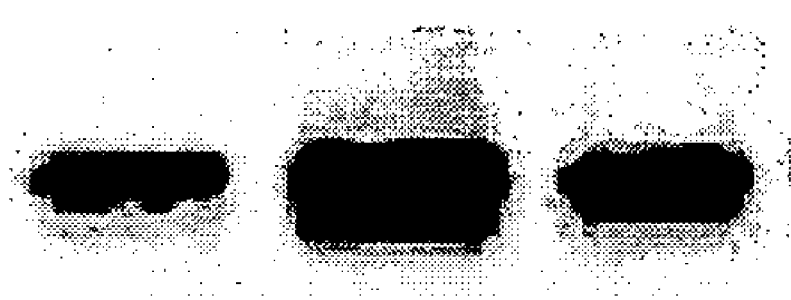
FIG. 26. Effect of LPA (10 µM), EGF (1 µM) and DMSO on levels of phospho-Akt as a in a CHO-K1 cell line stably transfected with OSGPR114.

The present invention relates to the use of the human G-protein coupled receptor OSGPR114 or OSGPR78, and variants thereof. Human and mouse OSGPR114 or OSGPR78 have been cloned previously. Human OSGPR114 and OSGPR78 receptor encoding DNA have the GenBank Accession numbers AJ272207 and AF000546 respectively. Mouse OSGPR114 and OSGPR78 receptor encoding DNA have the GenBank Accession numbers AY255621 and NM_175116 respectively. The term OSGPR114 or OSGPR78 as used herein incorporates variants of OSGPR114 or OSGPR78. OSGPR114 or OSGPR78 receptors for use in the screening methods of the invention include all species orthologues, e.g., may be mammalian, rodent, mouse, rat, rabbit, dog, monkey or human. Human nucleic acid and amino acid sequences are depicted in FIGS. 1-2. Human OSGPR114 or OSGPR78 is preferred. The term "variant" refers to a polypeptide which has the same essential character or basic biological functionality as OSGPR114 or OSGPR78. The essential character of OSGPR114 or OSGPR78 can be defined as that of a G-protein coupled receptor of similar structure that is activated by LPA as described herein. Thus, the term "variant" refers with respect to OSGPR114 in particular to a GPCR polypeptide of similar structure that activates a Gi/o G-protein response in response to LPA under the experimental conditions described herein (e.g. see FIG. 10).

To determine whether a candidate variant has the same function as OSGPR114 or OSGPR78, the ability of the variant to activate Gi/o-protein or other G-proteins can be determined. The effect of the candidate variant on Gi/o activation can be monitored. This can be carried out, for example, by contacting cells expressing the candidate variant with a ligand which activates Gi/o-protein when contacted with cells that express OSGPR114 or OSGPR78, and measuring a Gi/o-coupled readout. A control experiment is typically also carried out in which cells of the same type as those expressing the candidate variant, but expressing OSGPR114 or OSGPR78 instead, are contacted with the ligand and a corresponding Gi/o-coupled readout is measured. The effect attained by the candidate variant can then be directly compared with that attained by OSGPR114 or OSGPR78. It should be noted that, although OSGPR114 or OSGPR78 may activate a Gi/o-protein or other G-protein response under the experimental conditions employed herein (e.g. see FIG. 10 for OSGPR114 activation), under different experimental conditions OSGPR114 or OSGPR78 may activate other G-proteins. Thus, when different experimental conditions are employed the G-protein activated by OSGPR114 or OSGPR78 may have to be re-determined prior to comparison with a candidate variant.

Alternatively, a variant polypeptide is one of similar structure which binds to the same ligand as OSGPR114 or OSGPR78. That can be determined directly by contacting a candidate variant with a radiolabelled ligand that binds to OSGPR114 or OSGPR78 and monitoring binding of the ligand to the variant. Typically, the radiolabelled ligand can be incubated with cell membranes containing the candidate variant. The membranes can then be separated from non-bound ligand and dissolved in scintillation fluid to allow the radioactivity of the membranes to be determined by scintillation counting. Non-specific binding of the candidate variant may also be determined by repeating the experiment in the presence of a saturating concentration of non-radioactive ligand. Preferably a binding curve is constructed by repeating the experiment with various concentrations of the candidate variant. The ability of OSGPR114 or OSGPR78 to bind a ligand may also be determined indirectly as described below. Surface plasmon resonance methodology can also be utilized, with the advantage that radiolabelling is not required (e.g. see technology reviews as published by Biacore, in print and on their website; Myszka, D. G. and Rich, R. L. (2000) Pharmaceutical Science and Technology Today, 3:310-317; Quinn, J. G. et. al. (2000) Anal. Biochem. 281:135-143; Williams, C. (2000) Current Opinion Biotech. 11:42-46). Additional methods of determining and characterizing ligand binding are well known in the art (e.g. see Kenakin, T. (1997) Molecular Pharmacology, A Short Course. p. 1-235, Blackwell Science).

Typically, polypeptides with more than about 65% identity, preferably at least 80% or at least 90% and particularly preferably at least 95%, at least 97% or at least 99% identity, with the amino acid sequences of human or mouse OSGPR114 or OSGPR78 sequences as described in the Genbank database, or more preferably over a region of at least 20, preferably at least 30, at least 40, at least 60 or at least 100 contiguous amino acids or over the full length of the amino acid sequences are considered as OSGPR114 or OSGPR78 variants. The UWGCG Package provides the BESTFIT program which can be used to calculate identity (for example used on its default settings) (Devereau et al (1984) Nucleic Acid Research 12, p 387-395). The PILEUP and BLAST algorithms can be used to calculate identity or line up sequences (typically on their default settings), for example as described in Altschul S. F. (1993) J. Mol. Evol. 36: 290-300 and Altschul, S. F. et. al. (1990) J. Mol. Biol. 215:403. Software for performing BLAST analyses is publicly available through the National Center for Biotechnology Information (e.g. via their website).

Variant polypeptides therefore include naturally occurring allelic variants. An allelic variant will generally be of human or non-human mammal origin, such as bovine or porcine origin. Alternatively, a variant polypeptide can be a non-naturally occurring sequence. A non-naturally occurring variant may thus be a modified version of OSGPR114 or OSGPR78.

The amino acid sequence of OSGPR114 or OSGPR78 may be modified by deletion and/or substitution and/or addition of single amino acids or groups of amino acids as long as the modified polypeptide retains the capability to function as a G-protein coupled receptor. Such amino acid changes may occur in one, two or more of the intracellular domains of OSGPR114 or OSGPR78 and/or one, two or more of the extracellular domains of OSGPR114 or OSGPR78 and/or one, two or more of the transmembrane domains of OSGPR114 or OSGPR78.

Amino acid substitutions may thus be made, for example from 1, 2, 3, 4 or 5 to 10, 20 or 30 substitutions. Conservative substitutions may be made, for example according to the following Table. Amino acids in the same block in the second column and preferably in the same line in the third column may be substituted for each other.

| ALIPHATIC | Non-polar | G A P |
| | | I L V |
| | Polar-uncharged | C S T M |
| | | N Q |
| | Polar-charged | D E |
| | | K R |
| AROMATIC | | H F W Y |

A variant polypeptide may be a shorter polypeptide. For example, a polypeptide of at least 20 amino acids or up to 50, 60, 70, 80, 100, 150, 200, 250, or 300 amino acids in length may constitute a variant polypeptide as long as it demonstrates the functionality of OSGPR114 or OSGPR78. A variant polypeptide may therefore lack one, two or more intracellular domains and/or one, two or more extracellular domains and/or one, two or more transmembrane domains. A variant polypeptide may thus be a fragment of the full-length polypeptide. A shortened polypeptide may comprise a ligand-binding region (N-terminal extracellular domain) and/or an effector binding region (C-terminal intracellular domain). Such fragments can be used to construct chimeric receptors, preferably with another 7-transmembrane G-protein coupled receptor.

Variant polypeptides include polypeptides that are chemically modified, e.g. post-translationally modified. For example, such variant polypeptides may be glycosylated or comprise modified amino acid residues, e.g. phospho-amino acids. They may also be modified by the addition of histidine residues, for example 6 or 8 His residues, or an epitope tag, for example a T7, HA, myc or flag tag, to assist their purification or detection. They may be modified by the addition of a signal sequence to promote insertion into the cell membrane.

The invention also utilizes nucleotide sequences that encode OSGPR114 or OSGPR78 or variants thereof as well as nucleotide sequences which are complementary thereto. The nucleotide sequence may be RNA or DNA, including genomic DNA, synthetic DNA or cDNA. Preferably the nucleotide sequence is a DNA sequence, and most preferably, a cDNA sequence. Such nucleotides can be isolated from human cells or synthesized according to methods well known in the art, as described by way of example in Sambrook et. al., Molecular Cloning: A Laboratory Manual, $2^{nd}$ edition, Cold Spring Harbour Laboratory Press, 1989. Typically a useful polynucleotide comprises a contiguous sequence of nucleotides which is capable of hybridizing under selective conditions to the coding sequence or the complement of the coding sequences of OSGPR114 or OSGPR78.

A polynucleotide can hydridize to the coding sequence or the complement of the coding sequences of OSGPR114 or OSGPR78 at a level significantly above background. Background hybridization may occur, for example, because of other cDNAs present in a cDNA library. The signal level generated by the interaction between a polynucleotide and the coding sequence or complement of the coding sequence of OSGPR114 or OSGPR78 is typically at least 10 fold, preferably at least 100 fold, as intense as interactions between other polynucleotides and the coding sequence of OSGPR114 or OSGPR78. The intensity of interaction may be measured, for example, by radiolabelling the probe, e.g. with $^{32}P$ Selective hybridization may typically be achieved using conditions of low stringency (0.3 M sodium chloride and 0.03 M sodium citrate at about 40° C., medium stringency (for example, 0.3 M sodium chloride and 0.03 M sodium citrate at about 50° C., or high stringency (for example, 0.03 M sodium chloride and 0.003 M sodium citrate at about 60° C.

The coding sequences of OSGPR114 or OSGPR78 may be modified by one or more nucleotide substitutions, for example from 1, 2, 3, 4 or 5 to 10, 25, 50 or 100 substitutions. The polynucleotides of OSGPR114 or OSGPR78 may alternatively or additionally be modified by one or more insertions and/or deletions and/or by an extension at either or both ends. The modified polynucleotides generally encode polypeptides which have G-protein coupled receptor activity or inhibit the activity of OSGPR114 or OSGPR78. Degenerate substitutions may be made and/or substitutions may be made which would result in a conservative amino acid substitution when the modified sequences are translated, for example as shown in the Table above.

A nucleotide sequence which is capable of selectively hybridizing to the complement of the DNA coding sequences of OSGPR114 or OSGPR78 will generally have at least 60%, at least 70%, at least 80%, at least 90%, at least 95%, at least 98% or at least 99% sequence identity to the coding sequence of OSGPR114 or OSGPR78 over a region of at least 20, preferably at least 30, for instance at least 40, at least 60, more preferably at least 100, 300, 600, 900 contiguous nucleotides, or most preferably over the full length. Methods of measuring nucleic acid and protein homology are well known in the art. For example the UWGCG Package provides the BESTFIT program which can be used to calculate homology (Devereux J, et. al. (1984) Nucleic Acids Res 12:387-395). Similarly the PILEUP and BLAST algorithms can be used to line up sequences (for example, as described in Altschul, S. F. et. al. (1990) J. Mol. Biol. 215:403-410; Altschul, S. F., et. al. (1997) Nucleic Acids Res. 25:3389-3402). Many different settings are possible for such programs. In accordance with the invention, the default settings may be used.

Any combination of the above mentioned degrees of sequence identity and minimum sizes may be used to define polynucleotides of the invention, with the more stringent combinations (i.e. higher sequence identity over longer lengths) being preferred.

Thus, for example a polynucleotide which has at least 90% sequence identity over 25, preferably over 30 nucleotides forms one aspect of the invention, as does a polynucleotide which has at least 95% sequence identity over 40 nucleotides.

Polynucleotides may be used as a primer, e.g. a PCR primer or a primer for an alternative amplification reaction of a probe, e.g. labelled with a revealing label by conventional means for identifying mutations in OSGPR114 or OSGPR78 that may be implicated in diseases resulting from abnormal control of cell proliferation. Fragments of polynucleotides may be fused to the coding sequence of other proteins, preferably other G-protein coupled receptors, to form a sequence coding for a fusion protein.

Such primers, probes and other fragments will preferably be at least 10, preferably at least 15 or at least 20, for example at least 25, at least 30 or at least 40 nucleotides in length. They will typically be up to 40, 50, 60, 70, 100 or 150 nucleotides in length. Probes and fragments can be longer than 150 nucleotides in length, for example up to 200, 300, 400, 500 nucleotides in length, or even up to a few nucleotides, such as five or ten nucleotides, short of the coding sequences of OSGPR114 or OSGPR78.

The polynucleotides have utility in production of OSGPR114 or OSGPR78 or variant polypeptides, which may take place in vitro, in vivo or ex vivo. The polynucleotides may be used as therapeutic agents in their own right, in gene therapy techniques. The polynucleotides are cloned into expression vectors for these purposes. Such expression vectors are routinely constructed in the art of molecular biology and may for example involve the use of plasmid DNA and appropriate initiators, promoters, enhancers and other elements, such as for example polyadenylation signals which may be necessary, and which are positioned in the correct orientation, in order to allow for protein expression. Other suitable vectors would be apparent to a person skilled in the art. By way of further example in this regard, Molecular Cloning: a Laboratory Manual, 2001, $3^{rd}$ Edition, by Joseph Sambrook and Peter MacCallum (the former Maniatis Cloning manual) provides a good source.

Expression vectors comprise a polynucleotide encoding the desired polypeptide operably linked to a control sequence which is capable of providing for the expression of the coding sequence by a host cell. The term "operably linked" refers to a juxtaposition wherein the components described are in a relationship permitting them to function in their intended manner. A regulatory sequence, such as a promoter, "operably linked" to a coding sequence is positioned in such a way that expression of the coding sequence is achieved under conditions compatible with the regulatory sequence. Thus nucleic acid of this invention is operably linked when it is placed into a functional relationship with another nucleic acid sequence. For example, DNA for a presequence or secretory leader is operably linked to DNA for a polypeptide if it is expressed as a preprotein which participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, operably linked means that the DNA sequences being linked are contiguous and, in the case of a secretory leader, contiguous and in reading frame.

The vectors may be plasmid, virus or phage vectors provided with an origin of replication, optionally a promoter for the expression of the said polynucleotide, and optionally a regulator of the promoter. The vectors may contain one or more selectable marker genes, for example an ampicillin resistance gene in the case of a bacterial plasmid or a resistance gene for a fungal vector. Vectors may be used in vitro, for example for the production of RNA or DNA or used to transfect or transform a host cell, for example, a mammalian host cell. The vectors may also be adapted to be used in vivo, for example in a method of gene therapy.

This invention provides vectors comprising any nucleic acids encoding the OSGPR114 or OSGPR78 receptors of this invention, including vectors adapted for expression in a cell, which vector comprises the regulatory elements necessary for expression of the nucleic acid in the cell operatively linked to the nucleic acid encoding the receptor so as to permit expression thereof. Furthermore this invention also provides vectors which are plasmids.

This invention further provides host cells comprising any of the vectors described herein. The host cell is typically a eukaryotic cell, a mammalian cell, a human cell, an insect cell, a yeast cell or a prokaryotic cell, although is not limited to these. In one embodiment of this invention CHO, CHO-K1, RH7777, Jurkat, HCT4, or RBL243 cells are used. In another HeLa, ASPC-1, HEK-293, or COS7 cells are used.

Recombinant methods for synthesis of the OSGPR114 or OSGPR78 receptors of this invention commence with the construction of a replicable vector containing nucleic acid that encodes the OSGPR114 or OSGPR78 receptor. Vectors typically perform two functions in collaboration with compatible host cells. One function is to facilitate the cloning of the nucleic acid that encodes the OSGPR114 or OSGPR78 receptor, i.e., to produce usable quantities of the nucleic acid. The other function is to direct the expression of the OSGPR114 or OSGPR78 receptor. One or both of these functions are performed by the vector-host system. The vectors will contain different components depending upon the function they are to perform as well as the host cell that is selected.

This invention thus provides vectors that contain nucleic acid encoding the OSGPR114 or OSGPR78 receptor. Typically, this will be DNA that encodes the OSGPR114 or OSGPR78 receptor in its mature form linked at its amino terminus to a secretion signal. This secretion signal preferably is the signal presequence that normally directs the insertion of the wild-type OSGPR114 or OSGPR78 receptor through the plasma membrane. However, suitable secretion signals also include signals from other receptors or from secreted polypeptides of the same or related species.

In instances where the expression of OSGPR114 or OSGPR78 would exert an undesired biological effect on the host cell if induced to accumulate in high concentration in the cell membrane during the growth phase, this potential problem may be overcome by placing the nucleic acid encoding the OSGPR114 or OSGPR78 receptor under the control of an inducible promoter.

In the practice of this invention, for cloning vectors the OSGPR114 or OSGPR78 receptor-encoding nucleic acid ordinarily is present together with a nucleic acid sequence that enables the vector to replicate in a selected host cell independent of the host chromosomes. This sequence is generally an origin of replication or an autonomously replicating sequence. Such sequences are well-known for a variety of bacteria, yeast and higher eukaryotic cells. The origin from the well-known plasmid pBR322 is suitable for *E. coli* bacteria, the 2μ plasmid origin for yeast and various viral origins for mammalian cells (SV40, polyoma, adenovirus or bovine papilloma virus). Less desirably, DNA is cloned by insertion into the genome of a host. This is readily accomplished with *bacillus* species, for example, by inserting into the vector DNA that is complementary to *bacillus* genomic DNA. Transfection of *bacillus* with this vector results in homologous recombination with the genome and insertion of the OSGPR114 or OSGPR78 receptor DNA. However, the recovery of genomic DNA encoding the OSGPR114 or OSGPR78 receptor is more complex than obtaining exogenously replicated viral or plasmid DNA because restriction enzyme digestion is required to recover the OSGPR114 or OSGPR78 receptor DNA from the genome of the cloning vehicle.

In the practice of this invention, expression and cloning vectors should contain a selection gene, also termed a selectable marker. This is a gene that encodes a protein necessary for the survival or growth of a host cell transformed with the vector. The presence of this gene ensures the growth of only those host cells that express the inserts. Typical selection genes encode proteins that (a) confer resistance to antibiotics or other toxins, e.g. ampicillin, neomycin, blasticidin, G-418, mycophenolic acid, hygromycin B, bleomycin, phleomycin, methotrexate or tetracycline, (b) complement auxotrophic deficiencies, or (c) supply critical nutrients not available from complex media, e.g. the gene encoding D-alanine racemase for bacilli.

A suitable selection gene for use in yeast is the TRP1 gene present in the yeast plasmid YRp7 (Stinchcomb et al., 1979, "Nature", 282: 39; Kingsman et al., 1979, "Gene", 7: 141; or Tschemper et al., 1980, "Gene", 10: 157). The TRP1 gene provides a selection marker for a mutant strain of yeast lacking the ability to grow in the absence of tryptophan, for example ATCC No. 44076 or PEP41 (Jones, 1977, "Genetics", 85: 12). The presence of the trp1 lesion in the yeast host cell genome then provides an effective environment for detecting transformation by growth in the absence of tryptophan. Similarly, leu2 deficient yeast strains (ATCC 20,622 or 38,626) are complemented by known plasmids bearing the LEU2 gene.

Examples of suitable selectable markers for mammalian cells are dihydrofolate reductase (DHFR), thymidine kinase or proteins for neomycin resistance. Such markers enable the identification of cells that were competent to take up the OSGPR114 or OSGPR78 receptor nucleic acid. The mammalian cell transformants are placed under selection pressure, which only the transformants are uniquely adapted to survive by virtue of having taken up the marker. Selection pressure is imposed by culturing the transformants in successive rounds of cell culture, in which the concentration of selection agent in the medium is successively increased, thereby leading to amplification of both the selection gene and the DNA encoding the OSGPR114 or OSGPR78 receptor. Increased quantities of OSGPR114 or OSGPR78 receptor are synthesized from the amplified DNA.

For example, selection for DHFR transformed cells is conducted in a culture medium which lacks hypoxanthine, glycine, and thymidine. An appropriate host cell in this case is the Chinese hamster ovary (CHO) cell line deficient in DHFR activity, prepared and propagated as described by Urlaub and Chasin, 1980, "Proc. Nat'l. Acad, Sci. USA" 77: 4216.

A particularly useful DHFR is a mutant DHFR that is highly resistant to methotrexate (MTX) (EP 117,060A). This selection agent can be used with any otherwise suitable host, notwithstanding the presence of endogenous DHFR. One simply includes sufficient MTX in the medium to inactivate all of the endogenous DHFR, whereupon MTX selection becomes solely a function of amplification of the mutant DHFR DNA. Most eukaryotic cells which are capable of adsorbing MTX appear to be methotrexate sensitive. One such useful cell line is a CHO line, CHO-K1 (ATCC No. CCL 61).

Other methods, vectors and host cells suitable for adaptation to the synthesis of the OSGPR114 or OSGPR78 receptor of this invention in recombinant vertebrate cell culture are described in M. J. Gething et al., Nature 293: 620-625 (1981); N. Mantei et al., Nature 281: 40-46; EP 117,060A; EP 117,058A; Molecular Cloning: a Laboratory Manual, 2001, $3^{rd}$ Edition, by Joseph Sambrook and Peter MacCallum, (the former Maniatis Cloning manual) (e.g. ISBN 0-87969-577-3); and Current Protocols in Molecular Biology, Ed. Fred M. Ausubel, et. al. John Wiley & Sons (e.g. ISBN 0-471-50338-X).

Expression vectors of this invention, unlike cloning vectors, should contain a promoter and/or other sequence that is recognized by the host organism for strong transcription of the OSGPR114 or OSGPR78 receptor encoding DNA. This is generally a promoter homologous to the intended host. In the case of vectors for higher eukaryotes, enhancer sequences are useful for further increasing transcription from promoters. Unlike promoters, enhancers do not need to be located 5' to the OSGPR114 or OSGPR78 receptor encoding nucleic acid. Commonly used promoters for prokaryotes include the beta-lactamase and lactose promoter systems (Chang et al., 1978, "Nature", 275: 615; and Goeddel et al., 1979, "Nature", 281; 544), alkaline phosphatase, a tryptophan (trp) promoter system (Goeddel 1980, "Nucleic Acids Res." 8: 4057 and EPO Appln. Publ. No. 36,776) and hybrid promoters such as the tac promoter (H. de Boer et al., 1983, "Proc. Nat'l. Acad. Sci. USA" 80: 21-25). However, other known microbial promoters are suitable. Their nucleotide sequences have been published, thereby enabling a skilled worker operably to ligate them to DNA encoding the OSGPR114 or OSGPR78 receptor in plasmid vectors (Siebenlist et al., 1980, "Cell" 20: 269) using linkers or adaptors to supply any required restriction sites. Promoters for use in prokaryotic systems also will contain a Shine-Dalgarno (S.D.) sequence operably linked to the DNA encoding the OSGPR114 or OSGPR78 receptor.

Suitable promoting sequences in yeast vectors for use in the practice of this invention include *S. cerevisiae* GAL4 and ADH promoters, and *S. pombe* nmt1 and adh promoters, and further include the promoters for metallothionein, 3-phosphoglycerate kinase (Hitzeman et al., 1980, "J. Biol. Chem.", 255: 2073) or other glycolytic enzymes (Hess et al., 1968, "J. Adv. Enzyme Reg.", 7: 149; and Holland, 1978, "Biochemistry", 17: 4900), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters for use in the practice of this invention, which have the additional advantage of transcription controlled by growth conditions, are the promoter regions for alcohol dehydrogenase 2, isocytochrome C, acid phosphatase, degradative enzymes associated with nitrogen metabolism, and the aforementioned metallothionein and glyceralidehyde-3-phosphate dehydrogenase, as well as enzymes responsible for maltose and galactose utilization. Suitable vectors and promoters for use in yeast expression are further described in R. Hitzeman et al., EP 73,657A.

In the practice of this invention, transcription from vectors in mammalian host cells is controlled by promoters and/or enhancers obtained from the genomes of bovine papilloma virus, vaccinia virus, polyoma virus, adenovirus 2, retroviruses, hepatitis-B virus, cytomegalovirus (e.g. IE promoter), spleen focus forming virus, murine stem cell virus, Moloney murine leukemia virus (e.g. MMLV LTR), Simian Virus 40 (SV40), HSV (such as the HSV IE promoters), or HPV (particularly the HPV upstream regulatory region (URR)), operably linked to the OSGPR114 or OSGPR78 receptor nucleic acid. The early and late promoters of the SV40 virus are as conveniently obtained as an SV40 restriction fragment, which also contains the SV40 viral origin of replication (Fiers et al., 1978, "Nature", 273: 113). Mammalian promoters also include the metallothionein promoter, which can be induced in response to heavy metals such as cadmium. Of course, promoters or enhancers from the host cell or related species also are useful herein. Mammalian promoters, such as P-actin promoters, may be used. Tissue specific promoters, for example adipose or pancreatic cell specific promoters, may also be used. A suitable mammalian expression vector for practice of this invention is pcDNA3.1. Retrovirus vectors may also be used in the practice of this invention (e.g. rous sarcoma virus (RSV) LTR promoter), including those with inducible elements, e.g. tetracycline responsive elements.

The vector may further include sequences flanking the polynucleotide which comprise sequences homologous to eukaryotic genomic sequences, preferably mammalian genomic sequences, or viral genomic sequences. This will allow the introduction of the relevant polynucleotides into the genome of eukaryotic cells or viruses by homologous recombination. In particular, a plasmid vector comprising the expression cassette flanked by viral sequences can be used to prepare a viral vector suitable for delivering the polynucleotides of the invention to a mammalian cell. Retrovirus vectors for example may be used to stably integrate the polynucleotide into the host genome. Replication-defective adenovirus vectors by contrast remain episomal and therefore allow transient expression.

Expression vectors used in eukaryotic host cells of this invention (yeast, fungi, insect, plant, animal or human) will also contain sequences necessary for the termination of transcription and for stabilizing the mRNA. Such sequences are commonly available from the 3'-untranslated regions of eukaryotic or viral cDNAs. These regions contain regions that are transcribed as polyadenylated segments in the untranslated portion of the mRNA encoding the OSGPR114 or OSGPR78 receptor. The 3' untranslated regions also include transcription termination sites.

Cells are transformed or transfected with the vectors to express the OSGPR114 or OSGPR78 polypeptide or variants thereof. Such cells may be eukaryotic or prokaryotic. They include transient or, preferably, stable higher eukaryotic cell lines such as mammalian cells or insect cells, lower eukaryotic cells such as yeast, and prokaryotic cells such as bacterial cells. Particular examples of cells which may be used to express OSGPR114 or OSGPR78 or a variant polypeptide include mammalian cells such as HEK293T, CHO, CHO-K1, HeLa, ASPC-1, RH7777, Jurkat, HCT4, RBL243 and COS7 cells. Preferably the cell line selected will be one which is not only stable, but also allows for mature glycosylation and cell surface expression of OSGPR114 or OSGPR78 polypeptide or a variant. Cells such as adipose or pancreatic cells expressing OSGPR114 or OSGPR78 receptors or a variant polypeptide may be used in screening assays. Expression may be achieved in transformed oocytes. The OSGPR114 or OSGPR78 polypeptides or a variant may be expressed in cells such as those of adipose or pancreatic tissue of a transgenic non-human animal, preferably a rodent such as a mouse.

Suitable host cells for cloning or expressing the vectors herein are prokaryotes, yeast or higher eukaryotic cells. Prokaryotes include gram negative or gram positive organisms, for example *E. coli* or bacilli. A preferred cloning host is *E. coli* 294 (ATCC 31,446) although other gram negative or gram positive prokaryotes such as *E. coli* B, *E. coli* X1776 (ATCC 31,537), *E. coli* W3110 (ATCC 27,325), *Pseudomonas* species, or *Serratia marcesans* are suitable.

In addition to prokaryotes, eukaryotic microbes such as filamentous fungi or yeast are suitable hosts for the OSGPR114 or OSGPR78 receptor encoding vectors. *Saccharomyces cerevisiae*, or common baker's yeast, is the most commonly used among lower eukaryotic host microorganisms. However, a number of other genera, species and strains are commonly available and useful herein.

The preferred host cells for the expression of functional OSGPR114 or OSGPR78 receptors of this invention are cultures of cells derived from multicellular organisms. OSGPR114 or OSGPR78 receptors or variants thereof may contain hydrophobic regions that are incompatible with lower microorganisms, require complex processing to properly form disulfide bonds or require subunit processing. In addition, it may be desirable to glycosylate the receptor in a fashion similar to the native receptor. All of these functions can be best performed by higher eukaryotic cells. In principle, any higher eukaryotic cell culture is workable, whether from vertebrate or invertebrate culture, although cells from mammals such as humans are preferred. Propagation of such cells in culture is per se well known. See Tissue Culture, Academic Press, Kruse and Patterson, editors (1973), or Culture of Animal Cells: A Manual of Basic Technique, 4th Ed. Author, R. Ian Freshney, John Wiley & Sons., (2000). Examples of useful mammalian host cell lines are VERO and HeLa cells, human 239 cells, quail QT6 cells, NIH-3T3 cells, Chinese hamster ovary cell lines (CHO), W138, BHK, COS-7, HEK293, HeLa, ASPC-1, RH7777, Jurkat, HCT4, RBL243, and MDCK cell lines.

Thus, this invention also provides a cell comprising an OSGPR114 or OSGPR78 receptor. The cell of this invention can be eukaryotic, mammalian, human, insect or yeast. The cell comprising the OSGPR114 or OSGPR78 receptor of this invention can be a stable or transient transfectant.

In embodiments of this invention where purification of the OSGPR114 or OSGPR78 receptor is required, for example from a detergent solubilized membrane preparation containing the OSGPR114 or OSGPR78 receptor, the OSGPR114 or OSGPR78 receptor is readily purified by any of the protein purification techniques commonly practiced in the art, e.g. immunoaffinity chromatography. The recombinant OSGPR114 or OSGPR78 receptor can also be engineered to contain a structural element or epitope to assist in its purification, e.g. poly-histidine, calmodulin-binding peptide, glutathione-S-transferase, or maltose-binding protein.

The present invention is concerned in particular with the use of OSGPR114 or OSGPR78 or a functional variant in screening methods to identify agents that may act as modulators of OSGPR114 or OSGPR78 receptor activity and, in particular, agents that may act as modulators of cell proliferation, particularly inhibitors of cell proliferation that can inhibit tumor growth. Modulators identified by such screening methods are useful in the treatment OSGPR114 or OSGPR78-mediated diseases, including diseases or conditions such as cancer, obesity, certain diseases of the cardiovascular and respiratory systems, including artherosclerosis, restenosis and acetylcholine induced airway hyperresponsiveness, wound healing, reproductive function, abnormal immune system regulation, abnormalities in neuronal growth, survival and signaling, and renal failure associated with renal ischemia. By the term OSGPR114 or OSGPR78-mediated disease, it is meant those diseases or conditions where the modulation of OSGPR114 or OSGPR78 by agonists or antagonists results in a beneficial modification of the disease state or condition.

Any suitable form of assay may be employed to identify a modulator of OSGPR114 or OSGPR78 activity, and/or of cell proliferation or tumor growth. In general terms, such screening methods involve contacting OSGPR114 or OSGPR78 or a variant polypeptide with a test compound and then determining receptor activity. G-protein activation, for example Gi/o-protein or Gs-protein activation, may be determined therefore. Where a test compound affects receptor activity, its effect on cell proliferation can be determined by contacting cells with the test compound and measuring effects on cell proliferation by any of the methods well known in the art (e.g. see Experimental Details below).

OSGPR114 or OSGPR78 modulator activity can be determined in vitro or in vivo by contacting cells expressing OSGPR114 or OSGPR78 or a variant polypeptide with an agent under test and by monitoring the effect mediated by OSGPR114 or OSGPR78 or variant polypeptide. Thus, a test agent may be contacted with isolated cells which express OSGPR114 or OSGPR78 or a variant polypeptide. The cells may be provided in culture. Alternatively, cells may be disrupted and cell membranes isolated and used. OSGPR114 or OSGPR78 receptor protein may also be solubilized with the use of detergents (e.g. non-ionic detergents, such as digitonin), and the receptor purified and reconstituted in lipid vesicles, with other purified proteins as required. Such reconstituted ligand-stimulated GPCRs, that can activate second messenger systems, are well known in the art, and can be used in the practice of this invention.

The OSGPR114 or OSGPR78 or variant polypeptide may be naturally or recombinantly expressed. Preferably, an assay is carried out in vitro using cells expressing recombinant polypeptide or using membranes from such cells. Suitable eucaryotic and procaryotic cells are discussed above. In one embodiment, a cell type known to naturally express OSGPR114 or OSGPR78 receptors is used, e.g. an ovarian, liver, colon, lung, adipose or breast cell.

This invention provides a process for identifying a chemical compound which specifically binds to a mammalian OSGPR114 or OSGPR78 receptor which comprises contacting cells containing DNA encoding, and expressing on their cell surface, the mammalian OSGPR114 or OSGPR78 receptor, wherein such cells do not normally express the mammalian OSGPR114 or OSGPR78 receptor, with the compound under conditions suitable for binding, and detecting specific binding of the chemical compound to the mammalian OSGPR114 or OSGPR78 receptor.

This invention further provides a process for identifying a chemical compound which specifically binds to a mammalian OSGPR114 or OSGPR78 receptor which comprises contacting a membrane preparation from cells containing DNA encoding, and expressing on their cell surface, the mammalian OSGPR114 or OSGPR78 receptor, wherein such cells do not normally express the mammalian OSGPR114 or OSGPR78 receptor, with the compound under conditions suitable for binding, and detecting specific binding of the chemical compound to the mammalian OSGPR114 or OSGPR78 receptor.

In a further embodiment of these processes for identifying a chemical compound which specifically binds to a mammalian OSGPR114 or OSGPR78 receptor the contacting of the cells or membrane preparation with the compound is performed in the presence of a ligand for the OSGPR114 or OSGPR78 receptor, wherein the ligand is an LPA compound. In one embodiment, the LPA is selected from myristoyl lysophosphatidic acid, oleoyl lysophosphatidic acid, palmitoyl lysophosphatidic acid, and stearoyl lysophosphatidic acid, or a functional analog or homolog of one of these compounds.

In one embodiment, the mammalian OSGPR114 or OSGPR78 receptor is a human OSGPR114 or OSGPR78 receptor. In another embodiment, the mammalian OSGPR114 or OSGPR78 receptor has the same or substantially the same amino acid sequence as the human OSGPR114 or OSGPR78 receptor of FIG. 2.

In another embodiment, the mammalian OSGPR114 or OSGPR78 receptor is a mouse OSGPR114 or OSGPR78 receptor. In another embodiment, the mammalian OSGPR114 or OSGPR78 receptor has the same or substantially the same amino acid sequence as the mouse OSGPR114 or OSGPR78 receptor with GenBank Accession numbers AY255621 and NM_175116.

In another embodiment, the mammalian OSGPR114 or OSGPR78 receptor is a rat, dog, bovine, porcine or monkey OSGPR114 or OSGPR78 receptor.

In one embodiment, the compound is not previously known to bind to a mammalian OSGPR114 or OSGPR78 receptor. In one embodiment, the cell is an insect cell. In one embodiment, the cell is a mammalian cell. In another embodiment, the cell is a COS-7, ASPC-1, RH7777, Jurkat, HCT4, or RBL243 cell, a 293 human embryonic kidney cell, a CHO cell, a NIH-3T3 cell, a mouse Y1 cell, or a LM(tk–) cell. In another embodiment, the compound is a compound not previously known to bind to a mammalian OSGPR114 or OSGPR78 receptor. This invention provides a compound identified by the preceding process of this invention.

This invention provides an assay process for identifying a compound that specifically binds to a mammalian OSGPR114 or OSGPR78 receptor, said process comprising: providing either (a) two samples of cells expressing on their cell surface the mammalian OSGPR114 or OSGPR78 receptor, or (b) two samples of a membrane preparation from said cells; contacting one sample with a lysophosphatidic acid ligand known to bind to the receptor, under conditions suitable for binding of said ligand to the receptor, in the presence of a test compound; contacting the second sample with said ligand, under conditions suitable for binding of said ligand to the receptor, in the absence of the test compound; measuring the specific binding of the ligand to the receptor in the presence of the compound; measuring the specific binding of the ligand to the receptor in the absence of the compound; and comparing the binding in the presence and in the absence of the compound being tested, wherein a difference in comparison indicates that the compound binds to the mammalian OSGPR114 or OSGPR78 receptor. The compound identified may be, for example, a competitive or non-competitive antagonist, or a partial agonist.

This invention still further provides a process involving competitive binding for identifying a chemical compound which specifically binds to a mammalian OSGPR114 or OSGPR78 receptor which comprises separately contacting cells expressing on their cell surface the mammalian OSGPR114 or OSGPR78 receptor, wherein such cells do not normally express the mammalian OSGPR114 or OSGPR78 receptor (i.e. the host cells transformed or transfected with vectors to express the OSGPR114 or OSGPR78 polypeptide or variants thereof do not express these polypeptides at significant levels prior to introduction of the vector), with both the chemical compound and an LPA ligand, known to bind to the receptor, and with only the ligand, under conditions suitable for binding of such a ligand to the receptor, and detecting specific binding of the chemical compound to the mammalian OSGPR114 or OSGPR78 receptor, a decrease in the binding of the ligand to the mammalian OSGPR114 or OSGPR78 receptor in the presence of the chemical compound being tested indicating that such chemical compound binds to the mammalian OSGPR114 or OSGPR78 receptor.

This invention also provides a process involving competitive binding for identifying a chemical compound which specifically binds to a mammalian OSGPR114 or OSGPR78 receptor which comprises separately contacting a membrane preparation from cells expressing on their cell surface the mammalian OSGPR114 or OSGPR78 receptor, wherein such cells do not normally express the mammalian OSGPR114 or OSGPR78 receptor, with both the chemical compound and an LPA ligand, known to bind to the receptor, and with only the ligand, under conditions suitable for binding of such a ligand to the receptor, and detecting specific binding of the chemical compound to the mammalian OSGPR114 or OSGPR78 receptor, a decrease in the binding of the ligand to the mammalian OSGPR114 or OSGPR78 receptor in the presence of the chemical compound being tested indicating that such chemical compound binds to the mammalian OSGPR114 or OSGPR78 receptor.

In specific embodiments of these processes the LPA ligand is a naturally occurring LPA. In a further embodiment, LPA is selected from myristoyl lysophosphatidic acid, oleoyl lysophosphatidic acid, palmitoyl lysophosphatidic acid, and stearoyl lysophosphatidic acid, or a functional analog or homolog of one of these compounds.

In one embodiment, the mammalian OSGPR114 or OSGPR78 receptor is a human OSGPR114 or OSGPR78 receptor. In another embodiment, the mammalian OSGPR114 or OSGPR78 receptor is a rat OSGPR114 or OSGPR78 receptor. In another embodiment, the mammalian OSGPR114 or OSGPR78 receptor is a mouse OSGPR114 or OSGPR78 receptor. In a further embodiment, the cell is an insect cell. In another embodiment, the cell is a mammalian cell. In another embodiment, the cell is a yeast cell. In another embodiment, the cell is a ASPC-1, RH7777, Jurkat, HCT4, RBL243 or COS-7 cell, 293 human embryonic kidney cell (HEK-293), a CHO cell, a NIH-3T3 cell, a mouse Y1 cell, or a LM(tk−) cell. In another embodiment, the compound is not previously known to bind to a mammalian OSGPR114 or OSGPR78 receptor. This invention provides a compound identified by the preceding processes of this invention.

This invention provides a method of screening a plurality of compounds not known to bind to a mammalian OSGPR114 or OSGPR78 receptor to identify a compound which specifically binds to the mammalian OSGPR114 or OSGPR78 receptor, said process comprising: providing either (a) two samples of cells expressing on their cell surface the mammalian OSGPR114 or OSGPR78 receptor, or (b) two samples of a membrane preparation from said cells; contacting one sample with a lysophosphatidic acid ligand known to bind to the receptor, under conditions suitable for binding of said ligand to the receptor, in the presence of the plurality of compounds not known to bind to the receptor; contacting the second sample with said ligand, under conditions suitable for binding of said ligand to the receptor, in the absence of the plurality of compounds; measuring specific binding of the ligand to the receptor in the presence of the plurality of compounds; measuring specific binding of the ligand to the receptor in the absence of the plurality of compounds; comparing the binding in the presence and in the absence of the plurality of compounds, wherein a difference in the compared binding results indicates that one or more compounds in the plurality of compounds binds to the mammalian OSGPR114 or OSGPR78 receptor; and determining, when a difference in the compared binding is found, the binding to the mammalian OSGPR114 or OSGPR78 receptor of each compound included in the plurality of compounds, to identify any compound included therein which specifically binds to the mammalian OSGPR114 or OSGPR78 receptor.

This invention provides a method of screening a plurality of chemical compounds not known to bind to a mammalian OSGPR114 or OSGPR78 receptor to identify a compound which specifically binds to the mammalian OSGPR114 or OSGPR78 receptor, which comprises (a) contacting cells transfected with, and expressing, DNA encoding the mammalian OSGPR114 or OSGPR78 receptor with a compound known to bind specifically to the mammalian OSGPR114 or OSGPR78 receptor (e.g. a ligand); (b) contacting the cells of step (a) with the plurality of compounds not known to bind specifically to the mammalian OSGPR114 or OSGPR78 receptor, under conditions permitting binding of compounds known to bind to the mammalian OSGPR114 or OSGPR78 receptor; (c) determining whether the binding of the compound known to bind to the mammalian OSGPR114 or OSGPR78 receptor is reduced in the presence of the plurality of compounds, relative to the binding of the compound in the absence of the plurality of compounds; and if so (d) separately determining the binding to the mammalian OSGPR114 or OSGPR78 receptor of each compound included in the plurality of compounds, so as to thereby identify any compound included therein which specifically binds to the mammalian OSGPR114 or OSGPR78 receptor.

This invention provides a method of screening a plurality of chemical compounds not known to bind to a mammalian OSGPR114 or OSGPR78 receptor to identify a compound which specifically binds to the mammalian OSGPR114 or OSGPR78 receptor, which comprises (a) contacting a membrane preparation from cells transfected with, and expressing, DNA encoding the mammalian OSGPR114 or OSGPR78 receptor with a compound known to bind specifically to the mammalian OSGPR114 or OSGPR78 receptor (e.g. a ligand), and with the plurality of compounds not known to bind specifically to the mammalian OSGPR114 or OSGPR78 receptor, under conditions permitting binding of compounds known to bind to the mammalian OSGPR114 or OSGPR78 receptor; (b) determining whether the binding of a compound known to bind to the mammalian OSGPR114 or OSGPR78 receptor is reduced in the presence of the plurality of compounds, relative to the binding of the compound in the absence of the plurality of compounds; and if so (c) separately determining the binding to the mammalian OSGPR114 or OSGPR78 receptor of each compound included in the plurality of compounds, so as to thereby identify any compound included therein which specifically binds to the mammalian OSGPR114 or OSGPR78 receptor.

In specific embodiments of these methods the compound known to bind to the mammalian OSGPR114 or OSGPR78 receptor is an LPA ligand. In one embodiment it is a naturally occurring LPA. In a further embodiment, LPA is selected from myristoyl lysophosphatidic acid, oleoyl lysophosphatidic acid, palmitoyl lysophosphatidic acid, and stearoyl lysophosphatidic acid, or a functional analog or homolog of one of these compounds.

In one embodiment, the mammalian OSGPR114 or OSGPR78 receptor is a human OSGPR114 or OSGPR78 receptor. In a further embodiment, the mammalian OSGPR114 or OSGPR78 receptor is a rat OSGPR114 or OSGPR78 receptor. In another embodiment, the mammalian OSGPR114 or OSGPR78 receptor is a mouse OSGPR114 or OSGPR78 receptor. In another embodiment, the cell is a mammalian cell. In another embodiment, the cell is a yeast cell. In another embodiment the cell is a CHO, RH7777, Jurkat, HCT4, RBL243, or COS-7 cell, a 293 human embryonic kidney cell, a LM(tk−) cell, a CHO cell, a mouse Y1 cell, or an NIH-3T3 cell.

This invention provides a method of detecting expression of a mammalian OSGPR114 or OSGPR78 receptor by detecting the presence of mRNA coding for the mammalian OSGPR114 or OSGPR78 receptor which comprises obtaining total mRNA from the cell and contacting the mRNA so obtained with a nucleic acid probe according to this invention under hybridizing conditions, detecting the presence of mRNA hybridized to the probe, and thereby detecting the expression of the mammalian OSGPR114 or OSGPR78 receptor by the cell.

This invention provides a method of detecting the presence of a mammalian OSGPR114 or OSGPR78 receptor on the surface of a cell which comprises contacting the cell with an antibody according to this invention under conditions permitting binding of the antibody to the receptor, detecting the presence of the antibody bound to the cell, and thereby detecting the presence of the mammalian OSGPR114 or OSGPR78 receptor on the surface of the cell.

This invention provides a method of determining the physiological effects of varying levels of activity of mammalian OSGPR114 or OSGPR78 receptors which comprises producing a transgenic, nonhuman mammal in accordance with this invention whose levels of mammalian OSGPR114 or OSGPR78 receptor activity are varied by use of an inducible promoter which regulates mammalian OSGPR114 or OSGPR78 receptor expression.

This invention provides a method of determining the physiological effects of varying levels of activity of mammalian OSGPR114 or OSGPR78 receptors which comprises producing a panel of transgenic, nonhuman mammals in accordance with this invention each expressing a different amount of mammalian OSGPR114 or OSGPR78 receptor.

This invention provides a method for identifying an antagonist capable of alleviating an abnormality wherein the abnormality is alleviated by decreasing the activity of a mammalian OSGPR114 or OSGPR78 receptor comprising administering a compound to a transgenic, nonhuman mammal according to this invention, and determining whether the compound alleviates any physiological and/or behavioral abnormality displayed by the transgenic, nonhuman mammal as a result of overactivity of a mammalian OSGPR114 or OSGPR78 receptor, the alleviation of such abnormality identifying the compound as an antagonist. In one embodiment, the mammalian OSGPR114 or OSGPR78 receptor is a human OSGPR114 or OSGPR78 receptor. In a further embodiment, the mammalian OSGPR114 or OSGPR78 receptor is a rat OSGPR114 or OSGPR78 receptor. In another embodiment, the mammalian OSGPR114 or OSGPR78 receptor is a mouse OSGPR114 or OSGPR78 receptor. The invention provides an antagonist identified by the preceding method according to this invention. This invention provides a composition, e.g. a pharmaceutical composition, comprising an antagonist according to this invention and a carrier, e.g. a pharmaceutically acceptable carrier. This invention provides a method of treating an abnormality in a subject wherein the abnormality is alleviated by decreasing the activity of a mammalian OSGPR114 or OSGPR78 receptor which comprises administering to the subject an effective amount of the pharmaceutical composition according to this invention so as to thereby treat the abnormality. In one embodiment of this invention the abnormality is a tumor.

This invention provides a method for identifying an agonist capable of alleviating an abnormality in a subject wherein the abnormality is alleviated by increasing the activity of a mammalian OSGPR114 or OSGPR78 receptor comprising administering a compound to a transgenic, nonhuman mammal according to this invention, and determining whether the compound alleviates any physiological and/or behavioral abnormality displayed by the transgenic, nonhuman mammal, the alleviation of such an abnormality identifying the compound as an agonist. In one embodiment, the mammalian OSGPR114 or OSGPR78 receptor is a human OSGPR114 or OSGPR78 receptor. In a further embodiment, the mammalian OSGPR114 or OSGPR78 receptor is a rat OSGPR114 or OSGPR78 receptor. In another embodiment, the mammalian OSGPR114 or OSGPR78 receptor is a mouse OSGPR114 or OSGPR78 receptor. This invention provides an agonist identified by the preceding method according to this invention. This invention provides a composition, e.g. a pharmaceutical composition, comprising an agonist identified by the method according to this invention and a carrier, e.g. a pharmaceutically acceptable carrier.

This invention provides a method of treating an abnormality in a subject wherein the abnormality is alleviated by increasing the activity of a mammalian OSGPR114 or OSGPR78 receptor which comprises administering to the subject an effective amount of the pharmaceutical composition according to this invention so as to thereby treat the abnormality.

This invention provides a method for diagnosing a predisposition to a disorder associated with the activity of a specific mammalian allele of OSGPR114 or OSGPR78 which comprises: (a) obtaining DNA of subjects suffering from the disorder; (b) performing a restriction digest of the DNA with a panel of restriction enzymes; (c) electrophoretically separating the resulting DNA fragments on a sizing gel; (d) contacting the resulting gel with a nucleic acid probe capable of specifically hybridizing with a unique sequence included within the sequence of a nucleic acid molecule encoding a mammalian OSGPR114 or OSGPR78 receptor and labeled with a detectable marker; (e) detecting labeled bands which have hybridized to the DNA encoding a mammalian OSGPR114 or OSGPR78 receptor to create a unique band pattern specific to the DNA of subjects suffering from the disorder; (f) repeating steps (a)-(e) with DNA obtained for diagnosis from subjects not yet suffering from the disorder; and (g) comparing the unique band pattern specific to the DNA of subjects suffering from the disorder from step (e) with the band pattern from step (f) for subjects not yet suffering from the disorder so as to determine whether the patterns are the same or different and thereby diagnose predisposition to the disorder if the patterns are the same.

In one embodiment, the disorder is a disorder associated with the activity of a specific mammalian OSGPR114 or OSGPR78 receptor allele is diagnosed.

This invention provides a method of preparing a purified mammalian OSGPR114 or OSGPR78 receptor according to this invention which comprises: (a) culturing cells which express the mammalian OSGPR114 or OSGPR78 receptor; (b) recovering the mammalian OSGPR114 or OSGPR78 receptor from the cells; and (c) purifying the mammalian OSGPR114 or OSGPR78 receptor so recovered.

This invention provides a method of preparing the purified mammalian OSGPR114 or OSGPR78 receptor according to this invention which comprises: (a) inserting a nucleic acid encoding the mammalian OSGPR114 or OSGPR78 receptor into a suitable expression vector; (b) introducing the resulting vector into a suitable host cell; (c) placing the resulting host cell in suitable conditions permitting the production of the mammalian OSGPR114 or OSGPR78 receptor; (d) recovering the mammalian OSGPR114 or OSGPR78 receptor so produced; and optionally (e) isolating and/or purifying the mammalian OSGPR114 or OSGPR78 receptor so recovered.

This invention provides a process for determining whether a chemical compound is a mammalian OSGPR114 or OSGPR78 receptor agonist which comprises contacting cells transfected with and expressing DNA encoding the mammalian OSGPR114 or OSGPR78 receptor with the compound under conditions permitting the activation of the mammalian OSGPR114 or OSGPR78 receptor, and detecting any increase in mammalian OSGPR114 or OSGPR78 receptor activity, so as to thereby determine whether the compound is a mammalian OSGPR114 or OSGPR78 receptor agonist.

This invention provides a process for determining whether a chemical compound is a mammalian OSGPR114 or OSGPR78 receptor antagonist which comprises contacting cells transfected with and expressing DNA encoding the mammalian OSGPR114 or OSGPR78 receptor with the compound in the presence of a known mammalian OSGPR114 or OSGPR78 receptor agonist, under conditions permitting the activation of the mammalian OSGPR114 or OSGPR78 receptor, and detecting any decrease in mammalian OSGPR114 or OSGPR78 receptor activity, so as to thereby determine whether the compound is a mammalian OSGPR114 or OSGPR78 receptor antagonist.

In one embodiment, the mammalian OSGPR114 or OSGPR78 receptor is a human OSGPR114 or OSGPR78 receptor. In another embodiment, the mammalian OSGPR114 or OSGPR78 receptor is a rat OSGPR114 or OSGPR78 receptor. In another embodiment, the mammalian OSGPR114 or OSGPR78 receptor is a mouse OSGPR114 or OSGPR78 receptor.

This invention provides a composition, for example a pharmaceutical composition, which comprises an amount of a mammalian OSGPR114 or OSGPR78 receptor agonist determined by a process according to this invention effective to increase activity of a mammalian OSGPR114 or OSGPR78 receptor and a carrier, for example, a pharmaceutically acceptable carrier. In one embodiment, the mammalian OSGPR114 or OSGPR78 receptor agonist is not previously known.

This invention provides a composition, for example a pharmaceutical composition, which comprises an amount of a mammalian OSGPR114 or OSGPR78 receptor antagonist determined by a process according to this invention effective to reduce activity of a mammalian OSGPR114 or OSGPR78 receptor and a carrier, for example, a pharmaceutically acceptable carrier. In one embodiment, the mammalian OSGPR114 or OSGPR78 receptor antagonist is not previously known.

This invention provides a method of preparing a composition comprising a compound which specifically binds to a mammalian OSGPR114 or OSGPR78 receptor, which comprises identifying a compound that specifically binds to a mammalian OSGPR114 or OSGPR78 receptor by a process comprising: providing either (a) two samples of cells expressing on their cell surface the mammalian OSGPR114 or OSGPR78 receptor, or (b) two samples of a membrane preparation from said cells; contacting one sample with a lysophosphatidic acid ligand known to bind to the receptor, under conditions suitable for binding of said ligand to the receptor, in the presence of a test compound; contacting the second sample with said ligand, under conditions suitable for binding of said ligand to the receptor, in the absence of the test compound; measuring specific binding of the ligand to the receptor in the presence of the compound; measuring specific binding of the ligand to the receptor in the absence of the compound; and comparing the binding in the presence and in the absence of the compound being tested, wherein a difference in the binding of the ligand to the mammalian OSGPR114 or OSGPR78 receptor indicates that the compound binds to the mammalian OSGPR114 or OSGPR78 receptor; and admixing the compound so identified, or a functional analog or homolog of said compound, with a carrier, thereby preparing said composition.

This invention provides a method of preparing a composition, for example a pharmaceutical composition, comprising a chemical compound which specifically binds to a mammalian OSGPR114 or OSGPR78 receptor, which comprises separately contacting cells expressing on their cell surface the mammalian OSGPR114 or OSGPR78 receptor, wherein such cells do not normally express the mammalian OSGPR114 or OSGPR78 receptor, with both a test chemical compound and an LPA ligand, known to bind to the receptor, and with only the ligand, under conditions suitable for binding of such a ligand to the receptor, and detecting specific binding of the test chemical compound to the mammalian OSGPR114 or OSGPR78 receptor, a decrease in the binding of the ligand to the mammalian OSGPR114 or OSGPR78 receptor in the presence of the test chemical compound indicating that said test chemical compound binds specifically to the mammalian OSGPR114 or OSGPR78 receptor, and admixing the test chemical so identified, or a functional analog or homolog of said test chemical, with a carrier, thereby preparing said composition. In one embodiment of this method the mammalian OSGPR114 or OSGPR78 receptor is a human OSGPR114 or OSGPR78 receptor. In another embodiment it is a rat or mouse OSGPR114 or OSGPR78 receptor.

This invention provides a method of preparing a composition, for example a pharmaceutical composition, comprising a chemical compound which specifically binds to a mammalian OSGPR114 or OSGPR78 receptor, which comprises separately contacting a membrane preparation from cells expressing on their cell surface the mammalian OSGPR114 or OSGPR78 receptor, wherein such cells do not normally express the mammalian OSGPR114 or OSGPR78 receptor, with both a test chemical compound and an LPA ligand, known to bind to the receptor, and with only the ligand, under conditions suitable for binding of such a ligand to the receptor, and detecting specific binding of the test chemical compound to the mammalian OSGPR114 or OSGPR78 receptor, a decrease in the binding of the ligand to the mammalian OSGPR114 or OSGPR78 receptor in the presence of the test chemical compound indicating that said test chemical compound binds specifically to the mammalian OSGPR114 or OSGPR78 receptor, and admixing the test chemical so identified, or a functional analog or homolog of said test chemical, with a carrier, thereby preparing said composition. In one embodiment of this method the mammalian OSGPR114 or OSGPR78 receptor is a human OSGPR114 or OSGPR78 receptor. In another embodiment it is a rat or mouse OSGPR114 or OSGPR78 receptor.

This invention provides a process for determining whether a chemical compound specifically binds to and modulates activation of a mammalian OSGPR114 or OSGPR78 receptor, said process comprising: providing two samples of cells expressing on their cell surface the mammalian OSGPR114 or OSGPR78 receptor, wherein activation of the receptor produces a second messenger response; contacting one sample, in the presence of a test compound, with a second compound known to activate the receptor, under conditions suitable for activation of the receptor; contacting the second sample, in the absence of the test compound, with the second compound known to activate the receptor, under conditions suitable for activation of the receptor; measuring the second messenger response in the presence of the test compound, measuring the second messenger response in the absence of the test compound; and comparing the second messenger response in the presence and in the absence of the compound being tested, wherein a difference in the second messenger response from the mammalian OSGPR114 or OSGPR78 receptor indicates that the compound modulates activation of a mammalian OSGPR114 or OSGPR78 receptor. The compound identified may, for example, antagonize activation of the receptor by the second compound, either competitively or non-competitively, or may be an agonist or a partial agonist.

This invention provides a process for determining whether a chemical compound specifically binds to and activates a mammalian OSGPR114 or OSGPR78 receptor, which comprises contacting cells producing a second messenger response and expressing on their cell surface the mammalian OSGPR114 or OSGPR78 receptor, wherein such cells do not normally express the mammalian OSGPR114 or OSGPR78 receptor, with the chemical compound under conditions suitable for activation of the mammalian OSGPR114 or OSGPR78 receptor, and measuring the second messenger response in the presence and in the absence of the chemical compound, a change, e.g. an increase, in the second messenger response in the presence of the chemical compound indicating that the compound activates the mammalian OSGPR114 or OSGPR78 receptor.

In one embodiment, the second messenger response comprises chloride channel activation and the change in second messenger is an increase in the level of chloride current. In another embodiment, the second messenger response comprises a change in intracellular calcium levels and the change in second messenger is an increase in the measure of intracellular calcium. In another embodiment, the second messenger response comprises release of inositol phosphate and the change in second messenger is an increase in the level of inositol phosphate. In another embodiment, the second messenger response comprises release of arachidonic acid and the change in second messenger is an increase in the level of arachidonic acid. In yet another embodiment, the second messenger response comprises GTPγS ligand binding and the change in second messenger is an increase in GTPγS ligand binding. In another embodiment, the second messenger response comprises activation of MAP kinase and the change in second messenger response is an increase in MAP kinase activation. In a further embodiment, the second messenger response comprises cAMP accumulation and the change in second messenger response is an increase in cAMP accumulation. In another embodiment, the second messenger response comprises a change in intracellular sodium ion levels and the change in second messenger is an increase in the measure of intracellular sodium ions. In another embodiment, the second messenger response comprises a change in intracellular potassium ion levels and the change in second messenger is an increase in the measure of intracellular potassium ions.

Where the second messenger response being measured comprises GTPγS ligand binding, the key GPCR activation step of guanine nucleotide exchange on the G-protein α-subunit is being assessed. This is a very early event in the signal transduction cascade, and as such is an attractive event to monitor, because it is less subject to amplification or modification than more distal events that can be used to monitor OSGPR114 or OSGPR78 receptor activity.

This invention provides a process for determining whether a chemical compound specifically binds to and inhibits activation of a mammalian OSGPR114 or OSGPR78 receptor, which comprises separately contacting cells producing a second messenger response and expressing on their cell surface the mammalian OSGPR114 or OSGPR78 receptor, wherein such cells do not normally express the mammalian OSGPR114 or OSGPR78 receptor, with both the chemical compound and a second chemical compound known to activate the mammalian OSGPR114 or OSGPR78 receptor, and with only the second chemical compound, under conditions suitable for activation of the mammalian OSGPR114 or OSGPR78 receptor, and measuring the second messenger response in the presence of only the second chemical compound and in the presence of both the second chemical compound and the chemical compound, a smaller change, e.g. increase, in the second messenger response in the presence of both the chemical compound and the second chemical compound than in the presence of only the second chemical compound indicating that the chemical compound inhibits activation of the mammalian OSGPR114 or OSGPR78 receptor.

In one embodiment, the second messenger response comprises chloride channel activation and the change in second messenger response is a smaller increase in the level of chloride current in the presence of both the chemical compound and the second chemical compound than in the presence of only the second chemical compound. In another embodiment, the second messenger response comprises change in intracellular calcium levels and the change in second messenger response is a smaller increase in the measure of intracellular calcium in the presence of both the chemical compound and the second chemical compound than in the presence of only the second chemical compound. In another embodiment, the second messenger response comprises release of inositol phosphate and the change in second messenger response is a smaller increase in the level of inositol phosphate in the presence of both the chemical compound and the second chemical compound than in the presence of only the second chemical compound. In another embodiment, the second messenger response comprises a change in intracellular sodium ion levels and the change in second messenger is a smaller increase in the measure of intracellular sodium ions. In another embodiment, the second messenger response comprises a change in intracellular potassium ion levels and the change in second messenger is a smaller increase in the measure of intracellular potassium ions.

In one embodiment, the second messenger response comprises activation of MAP kinase and the change in second messenger response is a smaller increase in the level of MAP kinase activation in the presence of both the chemical compound and the second chemical compound than in the presence of only the second chemical compound. In another embodiment, the second messenger response comprises change in cAMP levels and the change in second messenger response is a smaller change in the level of cAMP in the presence of both the chemical compound and the second chemical compound than in the presence of only the second chemical compound. In another embodiment, the second messenger response comprises release of arachidonic acid and the change in second messenger response is an smaller increase in the level of arachidonic acid levels in the presence of both the chemical compound and the second chemical compound than in the presence of only the second chemical compound. In a further embodiment, the second messenger response comprises GTPγS ligand binding and the change in second messenger is a smaller increase in GTPγS ligand binding in the presence of both the chemical compound and the second chemical compound than in the presence of only the second chemical compound.

This invention provides a process for determining whether a chemical compound specifically binds to and enhances activation of a mammalian OSGPR114 or OSGPR78 receptor, which comprises separately contacting cells producing a second messenger response and expressing on their cell surface the mammalian OSGPR114 or OSGPR78 receptor, wherein such cells do not normally express the mammalian OSGPR114 or OSGPR78 receptor, with both the chemical compound and a second chemical compound known to activate the mammalian OSGPR114 or OSGPR78 receptor, and with only the second chemical compound, under conditions suitable for activation of the mammalian OSGPR114 or OSGPR78 receptor, and measuring the second messenger response in the presence of only the second chemical compound and in the presence of both the second chemical compound and the chemical compound, a larger change in the second messenger response in the presence of both the chemical compound and the second chemical compound than in the presence of only the second chemical compound indicating that the chemical compound enhances activation of the mammalian OSGPR114 or OSGPR78 receptor. In one embodiment the chemical compound that enhances activation of the mammalian OSGPR114 or OSGPR78 receptor is an allosteric or allotopic agonist.

In one embodiment, the second messenger response comprises chloride channel activation and the change in second messenger response is a greater increase in the level of chloride current in the presence of both the chemical compound and the second chemical compound than in the presence of only the second chemical compound. In another embodiment, the second messenger response comprises change in intracellular calcium levels and the change in second messenger response is a larger increase in the measure of intracellular calcium in the presence of both the chemical compound and the second chemical compound than in the presence of only the second chemical compound. In another embodiment, the second messenger response comprises release of inositol phosphate and the change in second messenger response is a larger increase in the level of inositol phosphate in the presence of both the chemical compound and the second chemical compound than in the presence of only the second chemical compound. In another embodiment, the second messenger response comprises a change in intracellular sodium ion levels and the change in second messenger is a larger increase in the measure of intracellular sodium ions. In another embodiment, the second messenger response comprises a change in intracellular potassium ion levels and the change in second messenger is a larger increase in the measure of intracellular potassium ions.

In one embodiment, the second messenger response comprises activation of MAP kinase and the change in second messenger response is a larger increase in the level of MAP kinase activation in the presence of both the chemical compound and the second chemical compound than in the presence of only the second chemical compound. In another embodiment, the second messenger response comprises change in cAMP levels and the change in second messenger response is a larger change in the level of cAMP in the presence of both the chemical compound and the second chemical compound than in the presence of only the second chemical compound. In another embodiment, the second messenger response comprises release of arachidonic acid and the change in second messenger response is a larger increase in the level of arachidonic acid levels in the presence of both the chemical compound and the second chemical compound than in the presence of only the second chemical compound. In a further embodiment, the second messenger response comprises GTPγS ligand binding and the change in second messenger is a larger increase in GTPγS ligand binding in the presence of both the chemical compound and the second chemical compound than in the presence of only the second chemical compound.

In one embodiment of the above processes the second messenger response is measured by a change in reporter gene activity. Examples of reporter gene include, but are not limited to, secreted alkaline phosphatase, luciferase, and β-galactosidase. Commonly used promoters In mammalian systems examples of promoters that can be used with such reporter genes include, but are not limited to, CREB-responsive, NFAT-responsive, NFkB-responsive, SRE-responsive, and CyclinD1 promoters In one embodiment, the mammalian OSGPR114 or OSGPR78 receptor is a human OSGPR114 or OSGPR78 receptor. In a further embodiment, the mammalian OSGPR114 or OSGPR78 receptor is a rat OSGPR114 or OSGPR78 receptor. In another embodiment, the mammalian OSGPR114 or OSGPR78 receptor is a mouse OSGPR114 or OSGPR78 receptor. In another embodiment, the cell is an insect cell. In another embodiment, the cell is a yeast cell. In another embodiment, the cell is a mammalian cell. In another embodiment, the mammalian cell is a CHO, RH7777, Jurkat, HCT4, RBL243, or COS-7 cell, a 293 human embryonic kidney cell, NIH-3T3 cell or LM(tk−) cell. In another embodiment, the compound is not previously known to bind to a mammalian OSGPR114 or OSGPR78 receptor.

In a preferred embodiment of the above processes of the invention, the second compound is an LPA compound. In an alternative embodiment the second compound is any of the compounds described in WO 02/29001; US 2003/0027800 A1; U.S. Pat. No. 6,380,177; Hasegawa, Y., et al. (2003) J. Biol. Chem. 278(14):11962-9; Heise, C. E., et al. (2001) Mol. Pharmacol 60(6):1173-80; Hooks, S. B., et al. (2001) J Biol Chem. 276(7):4611-21; Hopper, D. W., et al. (1999) J. Med. Chem. 42(6):963-70; Tigyi, G. (2001) Mol Pharmacol. 60(6): 1161-4; Yokoyama, K., et al. (2002). Biochim. Biophys. Acta 1582(1-3): 295-308; Gueguen, G., et al. (1999). Biochemistry 38(26): 8440-50; Lynch, K. R. and T. L. Macdonald (2002). Biochim. Biophys. Acta 1582(1-3): 289-94; Sardar, V. M., et al. (2002) Biochim. Biophys. Acta 1582: 309-307 or Virag, T., et al. (2003) Mol Pharmacol. 63(5):1032-42 as compounds that activate edg or LPA receptors. In a further embodiment, LPA is selected from myristoyl lysophosphatidic acid, oleoyl lysophosphatidic acid, palmitoyl lysophosphatidic acid, and stearoyl lysophosphatidic acid, or a functional analog or homolog of one of these compounds. In an alternative embodiment the lysophosphatidic acid is selected from 1-myristoyl lysophosphatidic acid, 1-oleoyl lysophosphatidic acid, 1-palmitoyl lysophosphatidic acid, and 1-stearoyl lysophosphatidic acid.

This invention provides a compound determined by a process or method according to this invention and a composition, for example, a pharmaceutical composition, which comprises an amount of a mammalian OSGPR114 or OSGPR78 receptor agonist determined to be such by a process according to this invention effective to increase activity of the mammalian OSGPR114 or OSGPR78 receptor and a carrier, for example, a pharmaceutically acceptable carrier. In one embodiment, the mammalian OSGPR114 or OSGPR78 receptor agonist is not previously known.

This invention provides a compound determined by a process or method according to this invention and a composition, for example, a pharmaceutical composition, which comprises an amount of a mammalian OSGPR114 or OSGPR78 receptor antagonist determined to be such by a process according to this invention, effective to reduce activity of the mammalian OSGPR114 or OSGPR78 receptor and a carrier, for example, a pharmaceutically acceptable carrier. In one embodiment, the mammalian OSGPR114 or OSGPR78 receptor antagonist is not previously known.

The compounds determined by a process or method according to this invention may be selective modulators of OSGPR114 or OSGPR78 activity, may be selective modulators of OSGPR114 and OSGPR78 activity but not active on other LPA receptors, may be selective modulators of OSGPR114 and/or OSGPR78 activity and active on a limited number of other LPA receptors (e.g. one, two or three), or may be modulators of all LPA receptors, in the latter case not necessarily with equivalent potency.

This invention provides a method of screening a plurality of chemical compounds not known to activate a mammalian OSGPR114 or OSGPR78 receptor to identify a compound which activates the mammalian OSGPR114 or OSGPR78 receptor which comprises: (a) contacting cells transfected with and expressing the mammalian OSGPR114 or OSGPR78 receptor with the plurality of compounds not known to activate the mammalian OSGPR114 or OSGPR78 receptor, under conditions permitting activation of the mammalian OSGPR114 or OSGPR78 receptor; (b) determining whether the activity of the mammalian OSGPR114 or OSGPR78 receptor is increased in the presence of one or more of the compounds; and if so (c) separately determining whether the activation of the mammalian OSGPR114 or OSGPR78 receptor is increased by any compound included in the plurality of compounds, so as to thereby identify each compound which activates the mammalian OSGPR114 or OSGPR78 receptor. In one embodiment, the mammalian OSGPR114 or OSGPR78 receptor is a human OSGPR114 or OSGPR78 receptor. In a further embodiment, the mammalian OSGPR114 or OSGPR78 receptor is a rat OSGPR114 or OSGPR78 receptor. In another embodiment, the mammalian OSGPR114 or OSGPR78 receptor is a mouse OSGPR114 or OSGPR78 receptor.

This invention provides a method of screening a plurality of chemical compounds not known to inhibit the activation of a mammalian OSGPR114 or OSGPR78 receptor to identify a compound which inhibits the activation of the mammalian OSGPR114 or OSGPR78 receptor, which comprises: (a) contacting cells transfected with and expressing the mammalian OSGPR114 or OSGPR78 receptor with the plurality of compounds in the presence of a known mammalian OSGPR114 or OSGPR78 receptor agonist, under conditions permitting activation of the mammalian OSGPR114 or OSGPR78 receptor; (b) determining whether the extent or amount of activation of the mammalian OSGPR114 or OSGPR78 receptor is reduced in the presence of one or more of the compounds, relative to the extent or amount of activation of the mammalian OSGPR114 or OSGPR78 receptor in the absence of such one or more compounds; and if so (c) separately determining whether each such compound inhibits activation of the mammalian OSGPR114 or OSGPR78 receptor for each compound included in the plurality of compounds, so as to thereby identify any compound included in such plurality of compounds which inhibits the activation of the mammalian OSGPR114 or OSGPR78 receptor.

In one embodiment, the mammalian OSGPR114 or OSGPR78 receptor is a human OSGPR114 or OSGPR78 receptor. In a further embodiment, the mammalian OSGPR114 or OSGPR78 receptor is a rat OSGPR114 or OSGPR78 receptor. In another embodiment, the mammalian OSGPR114 or OSGPR78 receptor is a mouse OSGPR114 or OSGPR78 receptor. In another embodiment, the cell is a yeast cell. In another embodiment, the cell is a mammalian cell. In another embodiment, the mammalian cell is an adipose, breast, ovarian, colon, lung or liver cell. In another embodiment, the cell is a CHO, RH7777, Jurkat, HCT4, RBL243, or COS-7 cell, a 293 human embryonic kidney cell, a LM(tk−) cell, a CHO cell, a mouse Y1 cell, or an NIH-3T3 cell.

This invention provides a composition, for example a pharmaceutical composition, comprising a compound identified by a method according to this invention in an amount effective to increase mammalian OSGPR114 or OSGPR78 receptor activity and a carrier, for example, a pharmaceutically acceptable carrier.

This invention provides a composition, for example, a pharmaceutical composition, comprising a compound identified by a method according to this invention in an amount effective to decrease mammalian OSGPR114 or OSGPR78 receptor activity and a carrier, for example, a pharmaceutically acceptable carrier.

This invention provides a method of treating an abnormality in a subject wherein the abnormality is alleviated by increasing the activity of a mammalian OSGPR114 or OSGPR78 receptor which comprises administering to the subject a compound which is a mammalian OSGPR114 or OSGPR78 receptor agonist in an amount effective to treat the abnormality. In one embodiment, the abnormality is a regulation of a steroid hormone disorder, an epinephrine release disorder, a gastrointestinal disorder, a cardiovascular disorder, an electrolyte balance disorder, hypertension, diabetes, a respiratory disorder, asthma, a reproductive function disorder, an immune disorder, an endocrine disorder, a musculoskeletal disorder, a neuroendocrine disorder, a cognitive disorder, a memory disorder, somatosensory and neurotransmission disorders, a motor coordination disorder, a sensory integration disorder, a motor integration disorder, a dopaminergic function disorder, an appetite disorder, obesity, a sensory transmission disorder, an olfaction disorder, an autonomic nervous system disorder, pain, psychotic behavior, affective disorder, migraine, cancer, proliferative diseases, wound healing, tissue regeneration, blood coagulation-related disorders, developmental disorders, or ischemia-reperfusion injury-related diseases.

This invention provides a method of treating an abnormality in a subject wherein the abnormality is alleviated by decreasing the activity of a mammalian OSGPR114 or OSGPR78 receptor which comprises administering to the subject a compound which is a mammalian OSGPR114 or OSGPR78 receptor antagonist in an amount effective to treat the abnormality. In one embodiment, the abnormality is a regulation of a steroid hormone disorder, an epinephrine release disorder, a gastrointestinal disorder, a cardiovascular disorder, an electrolyte balance disorder, hypertension, diabetes, a respiratory disorder, asthma, a reproductive function disorder, an immune disorder, an endocrine disorder, a musculoskeletal disorder, a neuroendocrine disorder, a cognitive disorder, a memory disorder, somatosensory and neurotransmission disorders, a motor coordination disorder, a sensory integration disorder, a motor integration disorder, a dopaminergic function disorder, an appetite disorder, obesity, a somatosensory neurotransmission disorder, an olfaction disorder, an autonomic nervous system disorder, pain, psychotic behavior, affective disorder, migraine, cancer, proliferative diseases, wound healing, tissue regeneration, blood coagulation-related disorders, developmental disorders, or ischemia-reperfusion injury-related diseases.

This invention provides a process for making a composition of matter which specifically binds to a mammalian OSGPR114 or OSGPR78 receptor which comprises identifying a chemical compound using a process in accordance with this invention and then synthesizing the chemical compound or a novel structural and functional analog or homolog thereof. In one embodiment, the mammalian OSGPR114 or OSGPR78 receptor is a human OSGPR114 or OSGPR78 receptor. In another embodiment, the mammalian OSGPR114 or OSGPR78 receptor is a rat OSGPR114 or OSGPR78 receptor. In another embodiment, the mammalian OSGPR114 or OSGPR78 receptor is a mouse OSGPR114 or OSGPR78 receptor.

This invention provides a process for preparing a composition, for example, a pharmaceutical composition which comprises admixing a carrier, for example, a pharmaceutically acceptable carrier, and a pharmaceutically effective amount of a chemical compound identified by a process in accordance with this invention or a novel structural and functional analog or homolog thereof. In one embodiment, the mammalian OSGPR114 or OSGPR78 receptor is a human OSGPR114 or OSGPR78 receptor. In another embodiment, the mammalian OSGPR114 or OSGPR78 receptor is a rat OSGPR114 or OSGPR78 receptor. In another embodiment, the mammalian OSGPR114 or OSGPR78 receptor is a mouse OSGPR114 or OSGPR78 receptor.

Thus, once the gene for a targeted receptor subtype such as OSGPR114 or OSGPR78 is cloned, it is placed into a recipient cell which then expresses the targeted receptor subtype on its surface. This cell, which expresses a single population of the targeted human receptor subtype, is then propagated resulting in the establishment of a cell line. This cell line, which constitutes a drug discovery system, is used in two different types of assays: binding assays and functional assays. In binding assays, the affinity of a compound for both the receptor subtype that is the target of a particular drug discovery program and other receptor subtypes that could be associated with side effects are measured. These measurements enable one to predict the potency of a compound, as well as the degree of selectivity that the compound has for the targeted receptor subtype over other receptor subtypes. The data obtained from binding assays also enable chemists to design compounds toward or away from one or more of the relevant subtypes, as appropriate, for optimal therapeutic efficacy. In functional assays, the nature of the response of the receptor subtype to the compound is determined. Data from the functional assays show whether the compound is acting to inhibit or enhance the activity of the receptor subtype, thus enabling pharmacologists to evaluate compounds rapidly at their ultimate human receptor subtypes targets permitting chemists to rationally design drugs that will be more effective and have fewer or substantially less severe side effects than existing drugs.

Approaches to designing and synthesizing receptor subtype-selective compounds are well known and include traditional medicinal chemistry and the newer technology of combinatorial chemistry, both of which are supported by computer-assisted molecular modeling. With such approaches, chemists and pharmacologists use their knowledge of the structures of the targeted receptor subtype and compounds determined to bind and/or activate or inhibit activation of the receptor subtype to design and synthesize structures that will have activity at these receptor subtypes.

Combinatorial chemistry involves automated synthesis of a variety of novel compounds by assembling them using different combinations of chemical building blocks. The use of combinatorial chemistry greatly accelerates the process of generating compounds. The resulting arrays of compounds are called libraries and are used to screen for compounds ("lead compounds") that demonstrate a sufficient level of activity at receptors of interest. Using combinatorial chemistry it is possible to synthesize "focused" libraries of compounds anticipated to be highly biased toward the receptor target of interest.

Once lead compounds are identified, whether through the use of combinatorial chemistry or traditional medicinal chemistry or otherwise, a variety of homologs and analogs are prepared to facilitate an understanding of the relationship between chemical structure and biological or functional activity. These studies define structure activity relationships which are then used to design drugs with improved potency, selectivity and pharmacokinetic properties. Combinatorial chemistry is also used to rapidly generate a variety of structures for lead optimization. Traditional medicinal chemistry, which involves the synthesis of compounds one at a time, is also used for further refinement and to generate compounds not accessible by automated techniques. Once such drugs are defined the production is scaled up using standard chemical manufacturing methodologies utilized throughout the pharmaceutical and chemistry industry.

In one aspect of this invention, OSGPR114 or OSGPR78 receptor activity is monitored by measuring a Gi/o-coupled readout. Gi/o-coupled readout can be monitored using an electrophysiological method to determine the activity of G-protein regulated $Ca^{2+}$ or $K^+$ channels or by using fluorescent dye to measure changes in intracellular $Ca^{2+}$ levels. Other methods that can typically be used to monitor receptor activity involved measuring levels of or activity of GTPγS or cAMP.

Yeast assays may be used to screen for agents that modulate the activity of OSGPR114 or OSGPR78 or variant polypeptides. A typical yeast assay involves heterologously expressing OSGPR114 or OSGPR78 or a variant polypeptide in a modified yeast strain containing multiple reporter genes, typically FUS1p-HIS-3 and FUS1p-lacZ, each linked to an endogenous MAPK cascade-based signal transduction pathway. This pathway is normally linked to pheromone receptors, but can be coupled to foreign receptors by replacement of the yeast G-protein with yeast/mammalian G-protein chimeras. Strains may also contain further gene deletions, such as deletions of SST2 and FAR1, to potentiate the assay. Ligand activation of the heterologous receptor can be monitored for example either as cell growth in the absence of histidine or with a suitable substrate for beta-galactosidase (lacZ). Such technology is well known in the art. See for example WO 99/14344, WO 00/12704, or U.S. Pat. No. 6,100,042.

Alternatively melanophore assays may be used to screen for modulators of OSGPR114 or OSGPR78. OSGPR114 or OSGPR78 or a variant polypeptide can be heterologously expressed in *Xenopus laevis* melanophores and their activation or inhibition can be measured by either melanosome dispersion or aggregation. Basically, melanosome dispersion is promoted by activation of adenylate cyclase or phospholipase C, i.e. Gs and Gq mediated signalling respectively, whereas aggregation results from activation of Gi-protein resulting in inhibition of adenylate cyclase. Hence, ligand activation of the heterologous receptor can be measured simply by measuring the change in light transmittance through the cells or by imaging the cell response.

Preferably, control experiments are carried out on cells which do not express OSGPR114 or OSGPR78 or a variant polypeptide to establish whether the observed responses are the result of activation of the OSGPR114 or OSGPR78 or the variant polypeptide.

Suitable test substances which can be tested in the above assays include combinatorial libraries, defined chemical entities, peptide and peptide mimetics, oligonucleotides and natural product libraries, such as display (e.g. phage display libraries) and antibody products. In one embodiment, the test substance is an LPA compound or a closely related compound. Assays may also be carried out using known ligands of other G-protein coupled receptors to identify additional ligands which act as agonists of OSGPR114 or OSGPR78.

Test substances may be used in an initial screen of, for example, 10 substances per reaction, and the substances of these batches which show inhibition or activation tested individually. Test substances may be used at a concentration of from 1 nM to 1000 µM, preferably from 1 µM to 100 µM, more preferably from 1 µM to 10 µM.

Agents which modulate OSGPR114 or OSGPR78 activity and which have been identified by assays in accordance with the invention can be used in the treatment or prophylaxis of diabetes, obesity or feeding disorders which are responsive to regulation of OSGPR114 or OSGPR78 receptor activity, and are one embodiment of this invention Agents which inhibit OSGPR114 or OSGPR78 receptor activity and/or which have been identified as inhibitors of cell proliferation are a preferred embodiment. In particular, such agents may be used in the treatment of certain cancers, including, but not limited to, ovarian cancer and other gynecological cancers, cancers of the lung, prostate, pancreas, colon, breast, esophagus, kidney and stomach, and glioma, lymphoma, leukemia and melanoma, and also obesity, atherosclerosis, restenosis, renal ischemia, and certain reproductive disorders.

In an alternative embodiment, agents which activate OSGPR114 or OSGPR78 receptor activity and/or which have been identified as stimulators of cell proliferation are also useful. In particular, such agents may be used in the treatment of wound healing and immune system disorders requiring activation of immune system cells (e.g. T-cells).

The amount of a OSGPR114 or OSGPR78 modulator which is required to achieve the desired biological effect will, of course, depend on a number of factors, for example, the mode of administration and the precise clinical condition of the recipient. In general, the daily dose will be in the range of 0.1-1000 mg/kg, typically 0.1-100 mg/kg. An intravenous dose may, for example, be in the range of 0.01 mg to 100 mg/kg, typically 0.01 to 10 mg/kg, which may conveniently be administered as an infusion of from 0.1 µg to 1 mg, per minute. Infusion fluids suitable for this purpose may contain, for example, from 0.01 µg to 0.1 mg, per milliliter. Unit doses may contain, for example, from 0.01 µg to 1 g of a OSGPR114 or OSGPR78 modulator. Thus ampoules for injection may contain, for example, from 0.01 µg to 0.1 g and orally administrable unit dose formulations, such as tablets or capsules, may contain, for example, from 0.1 mg to 1 g.

An OSGPR114 or OSGPR78 modulator may be employed in the treatment of a OSGPR114 or OSGPR78 mediated disease as the compound per se, but is preferably presented with an acceptable carrier in the form of a pharmaceutical formulation. The carrier must, of course, be acceptable in the sense of being compatible with the other ingredients of the formulation and must not be deleterious to the recipient. The carrier may be a solid or a liquid, or both, and is preferably formulated with the OSGPR114 or OSGPR78 modulator as a unit-dose formulation, for example, a tablet, which may contain from 0.05% to 95% by weight of the OSGPR114 or OSGPR78 modulator.

The formulations include those suitable for oral, rectal, topical, buccal (e.g. sub-lingual) and parenteral (e.g. subcutaneous, intramuscular, intradermal or intravenous) administration. Formulations suitable for oral administration may be presented in discrete units, such as capsules, cachets, lozenges or tablets, each containing a predetermined amount of a OSGPR114 or OSGPR78 modulator; as a powder or granules; as a solution or a suspension in an aqueous or non-aqueous liquid; or as an oil-in-water or water-in-oil emulsion. In general, the formulations are prepared by uniformly and intimately admixing the active OSGPR114 or OSGPR78 modulator with a liquid or finely divided solid carrier, or both, and then, if necessary, shaping the product. For example, a tablet may be prepared by compressing or moulding a powder or granules of the OSGPR114 or OSGPR78 modulator optionally with one or more accessory ingredients. Compressed tablets may be prepared by compressing, in a suitable machine, the compound in a free-flowing form, such as a powder or granules optionally mixed with a binder, lubricant, inert diluent and/or surface active/dispersing agent(s). Moulded tablets may be made by moulding, in a suitable machine, the powdered compound moistened with an inert liquid diluent.

Formulations suitable for buccal (sub-lingual) administration include lozenges comprising a OSGPR114 or OSGPR78 modulator in a flavoured base, usually sucrose and acacia or tragacanth, and pastilles comprising the OSGPR114 or OSGPR78 modulator in an inert base such as gelatin and glycerin or sucrose and acacia.

Formulations of the present invention suitable for parenteral administration conveniently comprise sterile aqueous preparations of an OSGPR114 or OSGPR78 modulator, preferably isotonic with the blood of the intended recipient.

These preparations are preferably administered intravenously, although administration may also be effected by means of subcutaneous, intramuscular, or intradermal injection. Such preparations may conveniently be prepared by admixing the OSGPR114 or OSGPR78 modulator with water and rendering the resulting solution sterile and isotonic with the blood. Injectable compositions according to the invention will generally contain from 0.1 to 5% w/w of the OSGPR114 or OSGPR78 modulator.

Formulations suitable for rectal administration are preferably presented as unit-dose suppositories. These may be prepared by admixing a OSGPR114 or OSGPR78 modulator with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which may be used include vaseline, lanolin, polyethylene glycols, alcohols, and combinations of two or more thereof. The OSGPR114 or OSGPR78 modulator is generally present at a concentration of from 0.1 to 15% w/w of the composition, for example, from 0.5 to 2%.

Alternatively, agents which up-regulate OSGPR114 or OSGPR78 expression or nucleic acids encoding OSGPR114 or OSGPR78 or a variant polypeptide may be administered to the mammal. Nucleic acid, such as RNA or DNA, preferably DNA, is provided in the form of a vector, which may be expressed in the cells of a human or other mammal under treatment. Preferably such up-regulation or expression following nucleic acid administration will enhance OSGPR114 or OSGPR78 activity.

OSGPR114 or OSGPR78 antisense nucleic acid or RNAi may also be used to decrease OSGPR114 or OSGPR78 protein levels and thus OSGPR114 or OSGPR78 activity, for use in cell proliferation disorders requiring inhibition of cell proliferation (e.g. cancer), or other OSGPR114 or OSGPR78 mediated diseases that would benefit from a decrease in OSGPR114 or OSGPR78 activity.

Nucleic acid encoding OSGPR114 or OSGPR78 or variant polypeptide may be administered to a human or other mammal by any available technique. For example, the nucleic acid may be introduced by injection, preferably intradermally, subcutaneously or intramuscularly. Alternatively, the nucleic acid may be delivered directly across the skin using a nucleic acid delivery device such as particle-mediated gene delivery. The nucleic acid may be administered topically to the skin, or to the mucosal surfaces for example by intranasal, oral, intravaginal, intrarectal administration.

Uptake of nucleic acid constructs may be enhanced by several known transfection techniques, for example those including the use of transfection agents. Examples of these agents include cationic agents, for example, calcium phosphate and DEAE-dextran and lipofectants, for example, lipofectam and transfectam. The dosage of the nucleic acid to be administered can be altered. Typically the nucleic acid is administered in the range of 1 pg to 1 mg, preferably to 1 pg to 10 μg nucleic acid for particle mediated gene delivery and 10 μg to 1 mg for other routes.

Polynucleotides encoding OSGPR114 or OSGPR78 or a variant polypeptide can also be used to identify mutation(s) in OSGPR114 or OSGPR78 genes which may be implicated in human disorders. Identification of such mutation(s) may be used to assist in diagnosis of feeding disorders and conditions associated with feeding disorders such as obesity, type II diabetes, insulin resistance and metabolic syndrome (syndrome X), or susceptibility to such disorders and in assessing the physiology of such disorders.

Antibodies (either polyclonal or preferably monoclonal antibodies, chimeric, single chain, Fab fragments) which are specific for the OSGPR114 or OSGPR78 polypeptides or a variant thereof can be generated. Such antibodies may for example be useful in purification, isolation or screening methods involving immunoprecipitation techniques and may be used as tools to elucidate further the function of OSGPR114 or OSGPR78 or a variant thereof, or indeed as therapeutic agents in their own right. Such antibodies may be used to block ligand binding to the receptors. A variety of protocols for competitive binding or immunoradiometric assays to determine the specific binding capability of an antibody are well known in the art (see for example Maddox et. al, J. Exp. Med. 158: 1211, 1993).

The activators, inhibitors, polynucleotides and antibodies for use in the instant invention may be used in combination with one or more other therapeutic agents. In one embodiment, in the treatment of cancer, other anticancer agents may be used in combination with an OSGPR114 or OSGPR78 receptor inhibitor, including, but not limited to alkylating agents, such as cyclophosphamide (CTX; cytoxan), chlorambucil (CHL; leukeran), cisplatin (CisP; platinol) busulfan (myleran), melphalan, carmustine (BCNU), streptozotocin, triethylenemelamine (TEM), mitomycin C, and the like alkylating agents; anti-metabolites, such as methotrexate (MTX), etoposide (VP16; vepesid) 6-mercaptopurine (6MP), 6-thiocguanine (6TG), cytarabine (Ara-C), 5-fluorouracil (5FU), dacarbazine (DTIC), and the like anti-metabolites; antibiotics, such as actinomycin D, doxorubicin (DXR; adriamycin), daunorubicin (daunomycin), bleomycin, mithramycin and the like antibiotics; alkaloids, such as vinca alkaloids such as vincristine (VCR), vinblastine, and the like; and other antitumor agents, such as taxol and taxol derivatives, the cytostatic agents, glucocorticoids such as dexamethasone (DEX; decadron) and corticosteroids such as prednisone, nucleoside enzyme inhibitors such as hydroxyurea, amino acid depleting enzymes such as asparaginase, and similar, diverse antitumor agents.

The use of the cytotoxic agents described above in chemotherapeutic regimens is generally well characterized in the cancer therapy arts, and their use herein falls under the same considerations for monitoring tolerance and effectiveness and for controlling administration routes and dosages, with some adjustments. For example, the actual dosages of the cytotoxic agents may vary depending upon the patient's cultured cell response determined by using the present histoculture methods. Generally, the dosage will be reduced compared to the amount used in the absence of agents that affect OSGPR114 or OSGPR78.

Typical dosages of an effective cytotoxic agent can be in the ranges recommended by the manufacturer, and where indicated by in vitro responses or responses in animal models, can be reduced by up to about one order of magnitude concentration or amount. Thus, the actual dosage will depend upon the judgment of the physician, the condition of the patient, and the effectiveness of the therapeutic method based on the in vitro responsiveness of the primary cultured malignant cells or histocultured tissue sample, or the responses observed in the appropriate animal models.

In one embodiment of this invention a protein-tyrosine kinase inhibitor may be used as a therapeutic agent in combination with an OSGPR114 or OSGPR78 receptor inhibitor of this invention. The protein-tyrosine kinase inhibitor may be, for example, an EGFR inhibitor, an IGFR inhibitor, a src kinase inhibitor, a PDGFR inhibitor, a HER2 kinase inhibitor, or an inhibitor of other protein-tyrosine kinases regulated by LPA, or an inhibitor of other protein-tyrosine kinases that are involved in causing abnormal cell growth or cancer. In one aspect of this invention these combinations are used for the treatment of the following disorders—cancers of the colon, lung, ovarian, breast, prostate, pancreas, esophagus, liver and stomach, and glioma, leukemia, lymphoma, and melanoma. In one embodiment the EGFR inhibitor is Tarceva (OSI-774), Iressa (gefinitib, ZD-1839) or an EGFR antibody (e.g. Erbitux (C225)).

In an alternative embodiment, in the treatment of obesity, Orlistat, Sibutramine, or a cannabinoid CB1 receptor antagonist may be used in combination with an OSGPR114 or OSGPR78 receptor modulator. The invention thus provides in a further aspect the use of a combination of an OSGPR114 or OSGPR78 modulator and at least one other therapeutic agent in the treatment of OSGPR114 or OSGPR78 mediated disorders.

When the activators, inhibitors and polynucleotides and antibodies are used in combination with other therapeutic agents, the agents may be administered either sequentially or simultaneously by any convenient route.

The combinations referred to above may conveniently be presented for use in the form of a pharmaceutical formulation and thus pharmaceutical formulations comprising a combination as defined above optimally together with a pharmaceutically acceptable carrier or excipient comprise a further aspect of the invention. The individual components of such combinations may be administered either sequentially or simultaneously in separate or combined pharmaceutical formulations.

When combined in the same formulation it will be appreciated that the two components must be stable and compatible with each other and the other components of the formulation and may be formulated for administration. When formulated separately they may be provided in any convenient formulation, conveniently in such a manner as are known for such compounds in the art.

When in combination with a second therapeutic agent active against the same disease, the dose of each component may differ from that when the compound is used alone. Appropriate doses will be readily appreciated by those skilled in the art.

Compounds of the invention that are identified as modulators of OSGPR114 or OSGPR78 activity can be screened by a variety of means known in the art to demonstrate their pharmacological activity. Compounds that have anti-cancer or anti-tumor activity for instance, can be identified in vivo using animal bioassay techniques known to those of ordinary skill in the art. Test compounds and appropriate vehicle controls can be administered by any of a number of routes (e.g., the oral route, a parenteral route) to experimental subjects and the size and growth of tumors can be monitored over the course of therapy. The experimental subjects are humans or test animals (e.g., rats, mice).

The inhibitory effective amount of a compound can be determined using art-recognized methods, such as by establishing dose response curves in suitable animal models and extrapolating to human; extrapolating from suitable in vitro data; or by determining effectiveness in clinical trials. Suitable doses of compounds of the invention depend upon the particular medical application, such as the severity of the disease, the weight of the individual, age of the individual, half-life in circulation, etc., and can be determined readily by the skilled artisan. The number of doses, daily dosage and course of treatment may vary from individual to individual.

The effects of compounds that modulate OSGPR114 or OSGPR78 activity on cell proliferation can be monitored by any of the many methods known to those of ordinary skill in the art, or modifications thereof (e.g. see Methods section herein).

The effects of compounds that modulate OSGPR114 or OSGPR78 activity on apoptosis can be monitored by any of the many methods known to those of ordinary skill in the art, or modifications thereof. Specific examples of apoptosis assays are exemplified in the following references. Assays for apoptosis in lymphocytes are disclosed by: Li et. al., (1995) Science 268:429-431; Gibellini et. al. (1995) Br. J. Haematol. 89:24-33; Martin et al. (1994) J. Immunol. 152:330-42; Terai et al., (1991) J. Clin Invest. 87:1710-5; Dhein et al. (1995) Nature 373:438-441; Katsikis et al. (1995) J. Exp. Med. 1815: 2029-2036; Westendorp et al. (1995) Nature 375:497; and DeRossi et al. (1994) Virology 198:234-44. Assays for apoptosis in fibroblasts are disclosed by: Vossbeck et al. (1995) Int. J. Cancer 61:92-97; Goruppi et al. (1994) Oncogene 9:1537-44; Fernandez et. al. (1994) Oncogene 9:2009-17; Harrington et al. (1994) EMBO J., 13:3286-3295; and Itoh et al., (1993) J. Biol. Chem. 268:10932-7. Assays for apoptosis in neuronal cells are disclosed by: Melino et al. (1994) Mol. Cell Biol. 14:6584-6596; Rosenblaum et al. (1994) Ann. Neurol. 36:864-870; Sato et. al. (1994) J. Neurobiol. 25:1227-1234; Ferrari et al. (1995) J. Neurosci. 1516:2857-2866; Talley et. al. (1995) Mol. Cell Biol. 1585:2359-2366; Talley et al. (1995) Mol. Cell. Biol. 15:2359-2366; and Waikinshaw et al. (1995) J. Clin. Invest. 95:2458-2464. Assays for apoptosis in insect cells are disclosed by: Clem et al. (1991) Science 254:1388-90; Crook et al. (1993) J. Virol: 67:2168-74; Rabizadeh et al. (1993) J. Neurochem. 61:2318-21; Birnbaum et al. (1994) J. Virol. 68:2521-8, 1994; and Clem et al. (1994) Mol. Cell. Biol. 14:5212-5222.

The effects of compounds that modulate OSGPR114 or OSGPR78 activity on cell motility, invasion and metastasis can be monitored by any of the many methods known to those of ordinary skill in the art, or modifications thereof (e.g. see Methods section herein). A typical assay for measuring cellular chemotaxis utilizes a so-called "Boyden chamber" (Boyden S. (1962) J. Exp. Med. 115:453-66), or similar apparatus, in which the cells migrate through a filter that has pore openings that are smaller than the cell diameter. Typically, cells of a particular type are placed in a chamber on one side of the filter and a chemotactic agent is placed in a chamber on the other side. Results are usually quantified by counting the number of cells that have migrated through the filter.

The effects of compounds that modulate OSGPR114 or OSGPR78 activity on angiogenesis or proangiogenic factor secretion by cells can be monitored by any of the many methods known to those of ordinary skill in the art, or modifications thereof. Angiogenesis can be considered to be the result of three distinct cellular activities: proliferation, migration and differentiation. Assays exist which model each of these phases separately. Simple in vitro tests measure changes in proliferation of a range of cell types and assess migration over basement membrane proteins. Current in vitro assay systems, which depend on provision of a protein matrix, effectively measure the ability of endothelial cells to differentiate. Assay systems measuring differentiation involve the formation of cord-like structures by endothelial cells. All such systems depend on supplying the cells with exogenous basement membrane proteins on which the cells migrate to form tubules. Cell migration occurs over relatively short time periods of 2-16 hours to give a three dimensional structure. In addition to the basement membrane proteins, many of the systems require the provision of growth factors to produce acceptable tubule formation. The time scale over which tubules are formed provides an excellent test for inhibition of differentiation.

Other angiogenesis assays that measure the complete process are based on in vivo systems. Three frequently used systems are the rabbit corneal pocket, the hamster cheek pouch and the chicken chorioallantoic membrane (CAM) assays (Folkman, J. and Brem, H. (1992) Angiogenesis and inflammation. In: "Inflammation. Basic Principles and Clinical Correlates". Eds Gallin, J. I., et. al., Raven Press, New York; Folkman, J. (1985) Adv. Cancer Res. 43:175; Folkman, J. and Klagsbrun, M. (1987) Science 235:442; Folkman, J. (1985) Perspect. Biol. Med. 29:10). In each system an angiogenic substances is implanted in the cornea, cheek pouch or the CAM in order to induce angiogenesis. In all three assays a sustained-release polymeric vehicle is used for delivery of the angiogenic substance and inhibitor compounds ((Langer, R and Folkman, J. (1976) Nature 263:797).

An alternative assay system (Yan, et al., (1993) J. Clin. Invest., 91:986-996) measures human angiogenesis, invasion and metastasis in a chimeric mouse:human model, and is referred to as the experimental human angiogenesis assay. It is a useful assay model for in vivo angiogenesis because the transplanted skin grafts closely resemble normal human skin histologically. In this model, human cancer cell invasion and neovascularization are occurring wherein actual human blood vessels and tissue are growing from the grafted human skin into the human tumor tissue on the surface of the grafted human skin. The origin of the neovascularization into the human graft can be demonstrated by immunohistochemical staining of the neovasculature with human-specific endothelial cell markers. The invasion and metastasis of human cancer cells may be monitored also. The assay can be used to demonstrate regression of neovascularization based on both the amount and extent of regression of new vessel growth. Effects on the invasion and metastasis of any cancer tissue transplanted upon the grafted skin are easily monitored. The assay is particularly useful because there is an internal control for toxicity in the assay system. The SCID mouse is exposed to any test reagent, and therefore the health of the mouse is an indication of toxicity.

The effects of compounds that modulate OSGPR114 or OSGPR78 activity on tumor growth can be monitored by any of the many methods known to those of ordinary skill in the art, or modifications thereof. For example, the efficacy of the compounds can be tested in animal models. For example, the efficacy of the compound alone or in combination with conventional anti-tumor agents such as cytotoxic/anti-neoplastic agents and anti-angiogenic agents can be compared to the conventional agents alone. Typically, a tumor of a given size is present in a rat or mouse. The mouse is treated with the agent and the size of the tumor is measured over time. The mean survival time of the animals can also be measured. The compounds modulating OSGPR114 or OSGPR78 receptor activity that are used must actively bind the receptor in the animal which is to be tested. Xenografts can be implanted into the animal to test the ability of species specific compounds to inhibit. Suitable test animals include, but are not limited to, inbred rats such as Fischer 344 and Lewis rats, and athymic NCR-NU mice.

Compounds of the invention that are identified as modulators of OSGPR114 or OSGPR78 activity can be screened by a variety of means known in the art to demonstrate pharmacological activity in obesity. Body fat reducing compounds, for instance, can be identified in vivo using animal bioassay techniques known to those of ordinary skill in the art. Test compounds and appropriate vehicle or caloric controls can be administered by any of a number of routes (e.g., the oral route, a parenteral route) to experimental subjects and the weight of the subjects can be monitored over the course of therapy. The experimental subjects are humans or test animals (e.g., rats, mice).

The effect of the compound on appetite or in inducing hypophagia or reduced food intake can be assessed, for instance, by monitoring the food consumption of the test subjects (e.g., measuring the amount eaten or not eaten by a subject in terms of food weight or caloric content). The effect of the compounds on appetite can also be assessed by subjective means including questionnaires as to appetite or food cravings levels by human subjects. The effect of the test compounds on lipid metabolism can be assessed by monitoring blood lipids and fatty acid oxidation. The techniques for these assessments are well known to those of ordinary skill in the art. The studies may be acute, subacute, chronic, or subchronic with respect to the duration of administration and or follow-up of the effects of the administration.

Body fat reduction can be determined, for instance, by directly measuring changes in body fat of the animal or by measuring changes in the body weight of the animal. The animal may be selected from the group consisting of a mouse, a rat, a guinea pig, or a rabbit. The animal may also be an ob/ob mouse, a db/db mouse, or a Zucker rat or other animal model for a weight-associated disease. Clinical studies in humans may also be conducted.

Compounds of the invention can be administered to an animal to determine whether they affect food intake and body weight, body fat, appetite, food seeking behavior, or modulate fatty acid oxidation. Animals can be, for example, obese or normal guinea pigs, rats, mice, or rabbits. Suitable rats include, for example, Zucker rats. Suitable mice include, for example, normal mice, ALS/LtJ, C3.SW-H-$2^b$/Snj, (NON/LtJxNZO/H1J)F1, NZO/H1J, ALR/LtJ, NON/LtJ, KK.Cg-AALR/LtJ, NON/LtJ, KK.Cg-A$^Y$/J, B6.HRS(BKS)-Cpe$^{fat}$/+, B6.129P2-Gck$^{tm/Efr}$, B6.V-Lep$^{ob}$, BKS.Cg-m +/+ Lep$^{rd}$b, and C57BL/6J with diet induced obesity.

Administration of an appropriate amount the candidate compound may be by any means known in the art such as, for example, oral or rectal, parenteral such as, for example, intraperitoneal, intravenous, subcutaneous, subdermal, intranasal, or intramuscular. Preferably administration may be intraperitoneal or oral. An appropriate effective amount of the candidate compound may be determined empirically as is known in the art. An appropriate effective amount may be an amount sufficient to effect a loss of body fat or a loss in body weight or reduction in food consumption in the animal over time. The candidate compound can be administered as often as required to effect a loss of body fat or loss in body weight, for example, hourly, every six, eight, twelve, or eighteen hours, daily, or weekly. Formulations suitable for oral administration include (a) liquid solutions, such as an effective amount of the candidate compound suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

Injection, solutions, and suspensions, can be prepared from sterile powders, granules, and tablets of the kind previously described. Formulations suitable for parenteral administration, include, for example, aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

The dose administered to the animal is sufficient to effect a change in body weight, body fat, and/or fatty acid oxidation over time. Such a dose can be determined according to the efficacy of the particular candidate compound employed and the condition of the animal, as well as the body weight or surface area of the animal. The size of the dose also will be determined by the existence, nature, and extent of any adverse side-effects that accompany the administration of a candidate compound; the $LD_{50}$ of the candidate compound; and the side-effects of the candidate compound at various concentrations. In general, the dose will range from 0.1-50 mg per kg, preferably 1-25 mg per kg, most preferably 1-20 mg per kg body weight. The determination of dose response relationships is well known to one of ordinary skill in the art.

Body weight reduction is typically determined by direct measurements of the change in body fat or by loss of body weight. Body fat and body weight of the animals is determined before, during, and after the administration of the candidate compound. Changes in body fat are measured by any means known in the art such as, for example, fat fold measurements with calipers, bioelectrical impedance, hydrostatic weighing, or dual x-ray absorbiometry (e.g. DEXA). Preferably animals demonstrate at least 2%, 5%, 8%, or 10% loss of body fat. Changes in body weight can be measured by any means known in the art such as, for example, on a portable scale, on a digital scale, on a balance scale, on a floor scale, or a table scale. Preferably animals demonstrate at least 2%, 5%, 10%, or 15% loss of body weight. Body weight reduction is measured before administration of the candidate compound and at regular intervals during and after treatment. Preferably, body weight is measured every 5 days, more preferably every 4 days, even more preferably every 3 days, yet more preferably every 2 days, most preferably every day.

Changes in fatty acid metabolism can be measured by looking at fatty acid oxidation in cells from major fat burning tissues such as, for example, liver (Beynen, et al. Diabetes 28:828 (1979)), muscle (Chiasson Lab. Anat. of Rat, (1980)), heart (Flink, et al. J Biol. Chem. 267: 9917 (1992)), and adipocytes (Rodbell, J. Biol. Chem. 239: 375 (1964)), Cells may be from primary cultures or from cell lines. Cells may be prepared for primary cultures by any means known in the art including, for example, enzymatic digestion and dissection. Suitable cell lines are known to those in the art. Suitable hepatocyte lines are, for example, Fao, MH1C1, H-4-II-E, H4TG, H4-II-E-C3, McA-RH7777, McA-RH8994, N1-S1 Fudr, N1-S1, ARL-6, Hepa 1-6, Hepa-1c1c7, BpRc1, tao BpRc1, NCTC clone 1469, PLC/PRF/5, Hep 3B2.1-7 [Hep 3B], Hep G2 [HepG2], SK-HEP-1, and WCH-17. Suitable skeletal muscle cell lines are, for example, L6, L8, C8, NOR-10, BLO-11, BC3H1, G-7, G-8, C2C12, P19, Sol8, SJRH30 [RMS 13], and QM7. Suitable cardiac cell lines are, for example, H9c2(2-1), P19, CCD-32Lu, CCD-32Sk, Girardi, and FBHE. Suitable adipocyte lines are, for example, NCTC clone 929 [derivative of Strain L; L-929; L cell], NCTC 2071, L-M, L-M(TK−) [LMTK−; LM(tk−)], A9 (APRT and HPRT negative derivative of Strain L), NCTC clone 2472, NCTC clone 2555, 3T3-L1, J26, J27-neo, J27-B7, MTKP 97-12 pMp97b [TKMp97-12], L-NGC-5HT2, Ltk-11, L-alpha-1b, L-alpha-2A, L-alpha-K, and B82.

The rate of fatty acid oxidation may be measured by $^{14}$C-oleate oxidation to ketone bodies (Guzman and Geelen, Biochem. J. 287:487 (1982)) and/or $^{14}$C-oleate oxidation to $CO_2$ (Fruebis, PNAS 98:2005 (2001); Blazquez et. al., J Neurochem 71:1597 (1998)). Lipolysis may be measured by fatty acid or glycerol release by using appropriate labeled precursors or spectrophotometric assays (Serradeil-Le Gal, FEBS Lett., 475:150 (2000)). For analysis of $^{14}$C-oleate oxidation to ketone bodies, freshly isolated cells or cultured cell lines can be incubated with $^{14}$C-oleic acid for an appropriate time, such as, for example, 30, 60, 90, 120, or 180 minutes. The amount of $^{14}$C radioactivity in the incubation medium can be measured to determine their rate of oleate oxidation. Oleate oxidation can be expressed as nmol oleate produced in x minutes per g cells. For analysis of lypolysis/glycerol release, freshly isolated cells or cultured cells lines can be washed then incubated for an appropriate time. The amount of glycerol released into the incubation media can provide an index for lipolysis.

Many alternative experimental methods known in the art may be successfully substituted for those specifically described herein in the practice of this invention, as for example described in many of the excellent manuals and textbooks available in the areas of technology relevant to this invention (e.g. Using Antibodies, A Laboratory Manual, edited by Harlow, E. and Lane, D., 1999, Cold Spring Harbor Laboratory Press, (e.g. ISBN 0-87969-544-7); Roe B. A. et. al. 1996, DNA Isolation and Sequencing (Essential Techniques Series), John Wiley & Sons. (e.g. ISBN 0-471-97324-0); Methods in Enzymology: Chimeric Genes and Proteins", 2000, ed. J. Abelson, M. Simon, S. Emr, J. Thorner. Academic Press; Molecular Cloning: a Laboratory Manual, 2001, $3^{rd}$ Edition, by Joseph Sambrook and Peter MacCallum, (the former Maniatis Cloning manual) (e.g. ISBN 0-87969-577-3); Current Protocols in Molecular Biology, Ed. Fred M. Ausubel, et. al. John Wiley & Sons (e.g. ISBN 0-471-50338-X); Current Protocols in Protein Science, Ed. John E. Coligan, John Wiley & Sons (e.g. ISBN 0-471-11184-8); and Methods in Enzymology: Guide to protein Purification, 1990, Vol. 182, Ed. Deutscher, M. P., Academic Press, Inc. (e.g. ISBN 0-12-213585-7)), or as described in the many university and commercial websites devoted to describing experimental methods in molecular biology.

This invention will be better understood from the Experimental Details which follow. However, one skilled in the art will readily appreciate that the specific methods and results discussed are merely illustrative of the invention as described more fully in the claims which follow thereafter, and are not to be considered in any way limited thereto.

EXPERIMENTAL DETAILS

Materials and Methods

Lipid Compounds

All LPA compounds used in the experiments described herein were purchased from Sigma-Aldrich (USA) or Avanti Polar Lipids (Alabaster, Ala., USA), and were all of sn1 configuration. LPA compounds can also be synthesized by methods known in the art (e.g. see Bandoh, K. et. al. (2000) FEBS Letters 478:158-165, and references cited therein).

Cell Lines and Reagents

Cell lines were purchased from the American Type Culture Collection and maintained in a suitable growth medium (e.g. DMEM) supplemented with Fetal Bovine Serum (e.g. 10% FBS). pcDNA 3.1 mammalian expression vector, PCR Blunt cloning vector, and DH5α competent *E. coli* cells were purchased from Invitrogen Life Corporation. PCR reagents were from Roche Molecular Systems, Inc. (N808-0228). Restriction endonucleases were from New England Biolabs, Inc. The primers used for PCR were synthesized by ACGT, Inc. Transfection reagents were purchased from Roche.

Cloning of Human and Mouse OSGPR114 or OSGPR78 Receptors

The OSGPR114 and OSGPR78 human and mouse genes are single exon genes of approximately 1.1 and 1.0 kilobase pairs in length with a 67.91% and 35.94% GC content respectively. The receptor genes were PCR amplified from 0.1 g human genomic DNA samples in a 25 µl reaction volume using the appropriate oligonucleotides 1-4 (FIG. 11) at 0.5 µM each, 0.5 mM dNTP mix, 1.5×Pfu buffer, and 2.5 units Pfu-turbo enzyme (Stratagene). PCR cycling conditions were set as follows: 2 minute hold at 95° C.; 35 cycles of template denaturing 15 seconds at 95° C., primer annealing 30 seconds at 55° C., primer extension 1 minute 30 seconds at 72° C.; 7 minute hold at 72° C.; final hold at 4° C. PCR DNA was purified from PCR reaction mix according to QIAGEN's QIAquick PCR purification spin column protocol.

Resulting DNA fragments were consecutively digested in a 1001 final reaction volume with appropriate restriction enzymes (1 unit/µg DNA) using manufacturers defined conditions for optimal enzyme use. The oligonucleotides were designed to create an NcoI restriction site at the receptor gene's ATG initiation codon. Following fragment digestion, DNA was gel purified from a 1.5% agarose gel using a QIAquick gel extraction protocol (QIAGEN).

The OSGPR114 and OSGPR78 genes were cloned into a yeast expression vector at the NcoI/XbaI restriction sites in a (cohesive) sticky-end ligation reaction. Ligation reactions were set up at a 3:1 insert to vector ratio using 25 ng digested parent yeast expression vector. The 20 µl reaction mix containing the DNA, 1× ligase buffer, and 20 units T4 DNA ligase, was incubated at room temperature for 1 hour. In the resulting construct, GPCR expression is under the control of the PGK promoter while the N-terminus of the receptor gene is fused to an 89 amino acid Mfα1-Leader sequence. Mfα1 is responsible for transporting the receptor to the cell membrane and is crucial for the performance of the FUS1p-LacZ yeast assay.

The receptor-vector was then transformed into TOPTEN chemically competent *E. coli* cells (Invitrogen). Between 1 µl and 5 µl ligation reaction product was introduced to 50 µl cells and incubated on ice for 30 minutes. Cells were then heat shocked for 30 seconds at 42° C., followed by 1 hour incubation in 250 µl S.O.C. media at 37° C. with agitation (225 rpm). After the 1 hour growth period, cells were spread out on LB agar plates with ampicillin and incubated overnight at 37° C. *E. coli* transformants containing ampicillin resistance were picked the following day and set up for plasmid isolation according to QIAGEN's miniprep protocol. DNA was analyzed by restriction digest using enzyme combination BglII/BamHI. Miniprep DNA digests resulting in a 7.6 kb+1.2 kb banding pattern on an agarose gel confirmed which plasmids contained the OSGPR114/OSGPR78 gene. Sequencing analysis of several clones was conducted. In a BLAST pairwise sequence alignment, the resulting sequence data from two individual DNA preparations were found to be 100% identical with the OSGPR114 sequence found in the literature. Two distinct sequences were identified from the samples of human genomic DNA for the OSGPR78 gene, one of which was consistent with the published sequence of OSGPR78 and one that contained a conservative Valine to Isoleucine amino acid substitution at position 33. It is feasible that this may reflect a polymorphism of the receptor, as the same change was observed in different PCR reactions from the same sample.

OSGPR114 and OSGPR78 were subcloned into pcDNA3.1, zeo mammalian expression vector from the yeast expression vectors by EcoRI/BamHI (for OSGPR114) or HindIII/Xho (for OSGPR78) digestion of the parent plasmid and pcDNA plasmid and the fragment from the yeast expression vector digestion ligated to the pcDNA3.1 digestion.

The rat, mouse, dog, or other mammalian homologs of OSGPR114 or OSGPR78 receptor sequences can readily be cloned by comparable methods.

Host Cells for Expression of Recombinant OSGPR114 or OSGPR78

A broad variety of host cells can be used to study heterologously expressed proteins. These cells include but are not limited to mammalian cell lines such as; Cos-7, CHO, LM(tk-), HEK293, RH7777, Jurkat, HCT4, RBL243, COS7 cells etc.; insect cell lines such as; Sf9, Sf21, etc.; amphibian cells such as *Xenopus* oocytes; assorted yeast strains; assorted bacterial cell strains; and others. Culture conditions for each of these cell types is specific and is known to those familiar with the art.

COS-7 cells are grown on 150 mm plates in DMEM with supplements (Dulbecco's Modified Eagle Medium with 10% bovine calf serum, 4 mM glutamine, 100 units/mL penicillin/100/g/mL streptomycin) at 37° C., 5% CO2. Stock plates of COS-7 cells are trypsinized and split 1:6 every 3-4 days.

CHO cells are grown on 150 mm plates in HAM's F-12 medium with supplements (10% bovine calf serum, 4 mM L-glutamine and 100 units/mL penicillin/100 µg/mL streptomycin) at 37° C., 5% CO2. Stock plates of CHO cells are trypsinized and split 1:8 every 3-4 days.

Transient Expression

DNA encoding proteins to be studied can be transiently expressed in a variety of mammalian, insect, amphibian, yeast, bacterial and other cell lines by several methods, such as, calcium phosphate-mediated, DEAE-dextran mediated, liposomal-mediated, viral-mediated, electroporation-mediated and microinjection delivery. Each of these methods may require optimization of assorted experimental parameters depending on the DNA, cell line, and the type of assay to be subsequently employed.

A typical protocol for the electroporation method as applied to Cos-7 cells is described as follows. Cells to be used for transfection are split 24 hours prior to the transfection to provide flasks which are subconfluent at the time of transfection. The cells are harvested by trypsinization resuspended in their growth media and counted. $5 \times 10^6$ cells are suspended in 300 µL of DMEM and placed into an electroporation cuvette. 8 µg of receptor DNA plus 8 µg of any additional DNA needed (e.g. G protein expression vector, reporter construct, antibiotic resistance marker, mock vector, etc.) is added to the cell suspension, the cuvette is placed into a BioRad Gene Pulser and subjected to an electrical pulse (Gene Pulser settings: 0.25 kV voltage, 950 µF capacitance). Following the pulse, 800 µL of complete DMEM is added to each cuvette and the suspension transferred to a sterile tube. Complete medium is added to each tube to bring the final cell concentration to 1×10⁵ cells/100 μL. The cells are then plated as needed depending upon the type of assay to be performed.

Stable Expression

Heterologous DNA can be stably incorporated into host cells, causing the cell to perpetually express a foreign protein. Methods for the delivery of the DNA into the cell are similar to those described above for transient expression but require the co-transfection of an ancillary gene to confer drug resistance on the targeted host cell. The ensuing drug resistance can be exploited to select and maintain cells that have taken up the DNA. An assortment of resistance genes are available including but not restricted to neomycin, kanamycin, and hygromycin. For the purposes of studies concerning the receptor of this invention, stable expression of a heterologous receptor protein is typically carried out in, mammalian cells including but not necessarily restricted to, CHO, HEK293, LM(tk-), ASPC-1, RH7777, Jurkat, HCT4, RBL243, COS7 cells etc.

In addition native cell lines that naturally carry and express the nucleic acid sequences for the receptor may be used without the need to engineer the receptor complement.

Quantitative Expression Analysis of OSGPR114 and OSGPR78

Quantitative RT-PCR by the ABI Prism 7700 Sequence Detector (TaqMan) was used to determine tissue specific expression of OSGPR114/OSGPR78 in a variety of human tissues and cell lines. Initially, RNA is isolated from these tissues according to Clontech's Nucleospin RNA II Protocol and kit for cultured cells. The cells are lysed using a kit buffer containing B-mercaptoethanol. The lysate is filtered and cleared using ethanol. The RNA in solution binds to provided nucleospin columns. Once bound to the column, the RNA is treated with a DNase, washed with buffers supplied in the kit, and eluted with nuclease-free water in ribonuclease-free tubes. The RNA yield is estimated using UV spectrophotometry with a conversion of 1.0 A260 unit RNA=40 μg/mL.

1 μg RNA is used for first-strand cDNA synthesis with SUPERSCRIPT II (Invitrogen) in a final RT-PCR reaction volume of 20 μl. The initial 11 μl reaction mixture containing 0.5 μg oligo (dT) 12-18, 1 μg RNA, and 500 μM dNTP mix, was heated to 65° C. for 5 minutes followed by a brief cooling on ice. This reaction volume was increased to 19 μl using 1× first-strand buffer, 0.01M DTT, and 40 units RNaseOUT-Ribonuclease Inhibitor (Ambion), and the reactions were heated to 42° C. for 2 minutes. Finally, 200 units SUPERSCRIPT II were added to the (+) reactions and water was added to the (-) No RT control reactions, making the final RT-PCR reaction volume 20 μl. The reactions were cycled once at 42° C. for 30 minutes, 45° C. for 15 minutes, 49° C. for 15 minutes, and 72° C. for 10 minutes. The total volume of the cDNA reaction was 20 μl containing 1ug RNA starting material. This starting material was diluted 1:20 in the reaction mixture. Therefore, the theoretical cDNA yield was 50 ng/μl. Samples were diluted two-fold to titrate the theoretical yield to 25 ng/μl.

cDNA (+) and No RT control samples were plated in 96 well PCR plates (Applied Biosystems) (with optical caps) for TaqMan/expression profiling using the expression oligonucleotide listed. Amplification TaqMan mix includes 1× TaqMan Universal PCR Master Mix (Applied Biosystems), 0.9 μM primer, 0.3 μM TaqMan probe, and 25 ng cDNA sample, for a total reaction volume of 25 μl. The reactions are cycled 40 times at 50° C. for 2 minutes, 95° C. for 10 minutes, 95° C. for 15 seconds, and 60° C. for 1 minute. A control plate using TFIIB primers and probe was used to confirm the presence of cDNA in the (+) samples, as well as, the absence of cDNA in the No RT controls. TFIIB is a transcription factor expressed in most cell lines. Therefore, TFIIB data is used for normalizing/standardizing expression data (Data are expressed as a ratio of gene expression/TFIIB expression).

The fluorogenic (TaqMan) probes (e.g. FIG. 12) are designed such that the oligonucleotide contains a 5'-reporter dye and a downstream, 3'-quencher dye. The reporter dye, such as FAM (6-carboxy-fluorescein), is a fluorescent dye linked to the 5' end of the nucleotide via a covalent bond. Located at the 3' end, TAMRA (6-carboxy-tetramethylrhodamine) is responsible for quenching the fluorescent reporter dye. This suppressive activity is due to the close proximity of the reporter dye and the quencher dye when the probe is intact. TaqMan probes are designed to hybridize to a sequence region internal to the target gene and no other gene (determined by BLAST analysis of designed oligonucleotide sequences). Gene-specific forward and reverse primers are also designed to hybridize the sequence regions flanking the probe hybridization sequence.

TaqMan PCR master mix contains AmpliTaq Gold polymerase. Because 5'-3' nuclease activity is characteristic of Taq polymerases, these polymerases have the ability to cleave nucleotides off the template DNA strand during 5' to 3' polymerization and amplification. Therefore, in a PCR reaction containing OSGPR114- or OSGPR78-Tqn1 in addition to OSGPR114 or OSGPR78 forward and reverse primers, the receptor probe will be cleaved from the DNA template during OSGPR114/OSGPR78-F1 primer extension. Upon cleavage of the 5' end of the probe, the reporter dye is released into solution and separated from the quencher dye. This results in the increase of reporter fluorescence during every PCR cycle. Therefore, the greater the fluorescence, the greater the amplification (and expression) of the target gene. The amount of fluorescence measured by the ABI Prism 7700 Sequence Detector is related to the amount of expressed OSGPR114 or OSGPR78 in genomic DNA equivalents.

TaqMan expression profiling was completed for OSGPR114 and OSGPR78 using Marathon-Ready cDNAs prepared from normal human tissues (Clontech), and in-house cDNAs made from tumor cell lines and from matched pairs of tumor and normal tissue using the aforementioned protocols.

Expression of OSGPR114 in Mammalian Cells

To set up secondary assays for the OSGPR114, cDNA encoding for the OSGPR114 (plasmid OP-T7403, pDNA3.1/OSGPR114, zeo) was stably transfected into CHO cells. Cells were selected in growing medium containing 0.2 mg/mL zeocin. Four stable clones were isolated by limited dilution. Total RNAs were isolated from untransfected CHO cells as well CHO/OSGPR114 clones. First strand cDNA was synthesized and used as templates. mRNA level was quantitated by PCR with Taqman using the OSGPR114 specific primers and the probe.

Membrane Preparations

Cell membranes expressing the receptor protein according to this invention are useful for certain types of assays including but not restricted to ligand binding assays, GTP-γ-S binding assays, and others. The specifics of preparing such cell membranes may in some cases be determined by the nature of the ensuing assay but typically involve harvesting whole cells and disrupting the cell pellet by sonication in ice cold buffer (e.g. 20 mM Tris-HCl, 5 mM EDTA, pH 7.4). The resulting crude cell lysate is cleared of cell debris by low speed centrifugation at 200×g for 5 min at 4° C. The cleared supernatant is then centrifuged at 40,000×g for 20 min at 4° C., and the resulting membrane pellet is washed by suspending in ice cold buffer and repeating the high speed centrifugation step.

The final washed membrane pellet is resuspended in assay buffer. Protein concentrations are determined by the method of Bradford (1976) using bovine serum albumin as a standard. The membranes may be used immediately or frozen for later use.

Alternatively, plasma membrane-containing P2 particulate fractions are readily prepared from cell pastes frozen at −80° C. after harvest. All procedures are carried out at 4° C. Cell pellets are resuspended in 1 mL of 10 mM Tris-HCl and 0.1 mM EDTA, pH 7.5 (buffer A) and by homogenisation for 20 s with a polytron homogeniser followed by passage (5 times) through a 25-guage needle. Cell lysates are centrifuged at 1,000 g for 10 min in a microcentrifuge to pellet the nuclei and unbroken cells and P2 particulate fractions are recovered by microcentrifugation at 16,000 g for 30 min. P2 particulate fractions are resuspended in buffer A and stored at −80° C. until required. Protein concentrations are determined using the bicinchoninic acid (BCA) procedure (Smith, P. K. et al. (1985) Analytical Biochemistry, 150:76-85) using BSA as a standard.

Generation of Baculovirus

The coding region of DNA encoding the OSGPR114 or OSGPR78 receptor disclosed herein may be subcloned into pBlueBacIII into existing restriction sites or sites engineered into sequences 5' and 3' to the coding region of the polypeptides. To generate baculovirus, 0.5 µg of viral DNA (BaculoGold) and 3 µg of DNA construct encoding a polypeptide may be co-transfected into 2×10$^6$ *Spodoptera frugiperda* insect Sf9 cells by the calcium phosphate co-precipitation method, as outlined by Pharmingen (in "Baculovirus Expression Vector System: Procedures and Methods Manual"). The cells then are incubated for 5 days at 27° C.

The supernatant of the co-transfection plate may be collected by centrifugation and the recombinant virus plaque purified. The procedure to infect cells with virus, to prepare stocks of virus and to titer the virus stocks are as described in Pharmingen's manual.

Yeast Assays

The yeast cell-based reporter assays have previously been described in the literature (e.g. see Miret J. J., et. al. (2002) J. Biol. Chem. 277:6881-6887; Campbell R. M., et. al. (1999) Bioorg Med. Chem. Lett. 9:2413-2418; King K., et. al. (1990) Science. 250:121-123); WO 99/14344; WO 00/12704; and U.S. Pat. No. 6,100,042). Briefly, yeast cells have been engineered such that the endogenous yeast G-alpha (GPA1) has been deleted and replaced with G-protein chimeras constructed using multiple techniques. Additionally the endogenous yeast alpha-cell GPCR, STE3 has been deleted to allow for a homologous expression of a mammalian GPCR of choice. In the yeast, elements of the pheromone signaling transduction pathway, which are conserved in eukaryotic cells (for example, the mitogen-activated protein kinase pathway), drive the expression of Fus1. By placing β-galactosidase (LacZ) under the control of the Fus1 promoter (Fus1p), a system has been developed whereby receptor activation leads to an enzymatic read-out. Different yeast strains (e.g. FIG. 6) denote the presence of different G-alpha chimeras (see "yeast reporter assays" in Results section below for definitions).

Yeast cells are transformed by an adaptation of the Lithium acetate method described by Agatep et. al. (Agatep, R., et. al. (1998) Transformation of *Saccharomyces cerevisiae* by the lithium acetate/single-stranded carrier DNA/polyethylene glycol (LiAc/ss-DNA/PEG) protocol. Technical Tips Online, Trends Journals, Elsevier). Briefly, yeast cells are grown overnight on yeast tryptone plates (YT). Carrier single-stranded DNA (10 µg), 2 µg of each of two Fus1p-LacZ reporter plasmids (one with URA3 selection marker and one with TRP1), 2 µg of OSGPR114 or OSGPR78 in yeast expression vector (2µ origin of replication) and a lithium acetate/polyethylene glycol/TE buffer is pipetted into an Epindorf tube. The yeast expression plasmid containing the receptor/no receptor control has a LEU2 marker. Yeast cells are inoculated into this mixture and the reaction proceeds at 30° C. for 60 minutes. The yeast cells are then heat-shocked at 42° C. for 15 minutes. The cells are then washed and spread on selection plates. The selection plates are synthetic defined yeast media minus LEU, URA and TRP (SD-LUT). After incubating at 30° C. for 2-3 days, colonies that grow on the selection plates are then tested in the LacZ assay.

In order to perform fluorometric enzyme assays for β-galactosidase, yeast cells were grown overnight in liquid SD-LUT media to an unsaturated concentration (i.e. the cells are still dividing and have not yet reached stationary phase). They are diluted in fresh media to an optimal assay concentration and 90 µL of yeast cells were added to 96-well black polystyrene plates (Costar). Compounds, dissolved in ethanol and diluted in a 1% BSA solution to 10× concentration, were added to the plates and the yeast are placed at 30° C. for 4 h. After 4 h, the substrate for the β-galactosidase is added to each well. The substrate may yield a fluorescent or colorimetric read-out upon the activity of the β-galactosidase. In these experiments, Fluorescein di (β-D-galactopyranoside) was used (FDG), a substrate for the enzyme that releases fluorescein, allowing a fluorometric read-out. 20/L of 500 µM FDG was used. After incubation of the cells with the substrate for 30-60 mins, 20 µL of 1 M sodium carbonate is added to terminate the reaction and enhance the fluorescent signal. The plates were then read in a fluorometer at 485/535 nm. As an alternate read-out system, the yeast are also engineered with a Fus1p-HIS gene which means that activation of the receptor can also be measured through the growth of the yeast in a histamine deficient media.

Melanophore Assays

Polypeptide of the invention can be heterologously expressed in *Xenopus laevis* melanophores and its activation can be measured by either melanosome dispersion or aggregation. Basically, melanosome dispersion is promoted by activation of adenylate cyclase or phospholipase C i.e. Gs and Gq mediated signalling, respectively, whereas aggregation results from activation of Gi/o G proteins resulting in inhibition of adenylate cyclase. Hence, ligand activation of the OSGPR114 or OSGPR78 can be measured simply by measuring the change in light transmittance through the cells or by imaging the cell response.

Assays for Compound Screening

OSGPR114 or OSGPR78 modulator activity can be determined by contacting cells expressing an OSGPR114 or OSGPR78 polypeptide of the invention with a substance under investigation and by monitoring the effect mediated by the polypeptides. The cells expressing the polypeptide may be in vitro or in vivo. The polypeptide of the invention may be naturally or recombinantly expressed. Preferably, the assay is carried out in vitro using cells expressing recombinant polypeptide. Typically, receptor activity can be monitored indirectly by measuring a Gi/o-coupled readout. Gi/o coupled readout can typically be monitored using an electrophysiological method to determine the activity of G-protein regulated $Ca^+$ or $K^+$ channels or by using a fluorescent dye to measure changes in intracellular $Ca^{2+}$ levels. Other methods that can typically be used to monitor receptor activity involve measuring levels of or activity of labeled bound GTPγs or cAMP.

Preferably, control experiments are carried out on cells which do not express the polypeptide of the invention to establish whether the observed responses are the result of activation of the polypeptide.

Mammalian cells, such as HEK293, CHO, COS7, RH7777, Jurkat, HCT4, and RBL243 cells over-expressing the protein of choice are generated for use in the assay. Cell lines which maybe employed as suitable hosts include i) CHO cells transfected to stably express PLC 2, a PLC isoform which allows Gi/o G proteins to elicit $Ca^{2+}$ mobilization, or ii) CHO cells transfected to stably express the Gq family G-protein $G_{16}$ together with a suitable reporter construct gene e.g. the Gq responsive NFAT (nuclear factor activator of T cells) promoter controlling expression of luciferase. Expression of $G_{16}$ permits a wide variety of non-Gq coupled receptors to mobilize $Ca^{2+}$.

96 and 384 well plate high throughput screens (HTS) are employed using a) fluorescence based calcium indicator molecules, including but not limited to dyes such as Fura-2, Fura-Red, Fluo 3 and Fluo 4 (Molecular Probes); or b) reporter gene read-out. Secondary screening involves the same technology. A brief screening assay protocol is as follows:—

Mammalian cells stably over-expressing the protein are cultured in black wall, clear bottom, tissue culture coated 96 or 384 well plates with a volume of 100 μL cell culture medium in each well 3 days before use in a FLIPR (Fluorescence Imaging Plate Reader—Molecular Devices). Cells were incubated with 4 μM Fluo-3 at 30° C. in 5% $CO_2$ for 90 mins and then washed once in Tyrodes buffer containing 3 mM probenecid. Basal fluorescence is determined prior to compound additions. Activation results in an increase in intracellular calcium which can be measured directly in the FLIPR.

The binding of a modulator to a polypeptide of the invention can also be determined directly. For example, a radiolabeled test substance can be incubated with the polypeptide of the invention and binding of the test substance to the polypeptide can be monitored. Typically, the radiolabeled test substance can be incubated with cell membranes containing the polypeptide until equilibrium is reached. The membranes can then be separated from a non-bound test substance and dissolved in scintillation fluid to allow the radioactive content to be determined by scintillation counting. Non-specific binding of the test substance may also be determined by repeating the experiment in the presence of a saturating concentration of a non-radioactive ligand.

Labeled Ligand Binding Assays

Cells expressing the receptor according to this invention may be used to screen for ligands for said receptors, for example, by labeled ligand binding assays. Once a ligand is identified the same assays may be used to identify agonists or antagonists of the receptor that may be employed for a variety of therapeutic purposes.

In an embodiment, labeled ligands are placed in contact with either membrane preparations or intact cells expressing the receptor in multi-well microtiter plates, together with unlabeled compounds, and binding buffer. Binding reaction mixtures are incubated for times and temperatures determined to be optimal in separate equilibrium binding assays. The reaction is stopped by filtration through GF/B filters, using a cell harvester, or by directly measuring the bound ligand. If the ligand was labeled with a radioactive isotope such as $^3H$, $^{14}C$, $^{125}I$, $^{35}S$, $^{32}P$, $^{33}P$, etc., the bound ligand may be detected by using liquid scintillation counting, scintillation proximity, or any other method of detection for radioactive isotopes. For example, see above for $^3H$-LPA assay. If the ligand was labeled with a fluorescent compound, the bound labeled ligand may be measured by methods such as, but not restricted to, fluorescence intensity, time resolved fluorescence, fluorescence polarization, fluorescence transfer, or fluorescence correlation spectroscopy. In this manner agonist or antagonist compounds that bind to the receptor may be identified as they inhibit the binding of the labeled ligand to the membrane protein or intact cells expressing the receptor. Non-specific binding is defined as the amount of labeled ligand remaining after incubation of membrane protein in the presence of a high concentration (e.g., 100-1000×$K_D$) of unlabeled ligand. In equilibrium saturation binding assays membrane preparations or intact cells transfected with the receptor are incubated in the presence of increasing concentrations of the labeled compound to determine the binding affinity of the labeled ligand. The binding affinities of unlabeled compounds may be determined in equilibrium competition binding assays, using a fixed concentration of labeled compound in the presence of varying concentrations of the displacing ligands.

For example, in one method employed herein, membranes from untransfected CHO cells as well as OSGPR114 stable clones were prepared using the method described by Griffin et al (1998). Membranes were homogenized in buffer containing 50 mM Tris, 5 mM $MgCl_2$, 2.5 mM EDTA, 0.1% fatty acid free BSA, pH 7.4. Assays were performed in a reaction mixture containing 501 of membrane suspension (~3 g/well), 25 μl of [$^3H$]-LPA (final concentration=56 nM:25 μl aliquot counted to determine precise concentration employed). Non-specific binding was measured in the presence of 10 μM LPA. Incubations were carried out in triplicate for 60 minutes at 37° C. Reactions were terminated by rapid filtration over GF/B filters presoaked in ice cold wash buffer for 90 minutes. The filters were then washed 6 times with 0.3 mL of ice cold 50 mM Tris, 5 mM $MgCl_2$, 2.5 mM EDTA, 0.1% fatty acid free BSA, pH 7.4. The filters were dried, covered with Microscint-20, dark adapted for 5 minutes, and counted on a 2 minute tritium protocol on a Packard TopCount LSC.

Functional Assays

Cells expressing the OSGPR114 or OSGPR78 receptor DNA may be used to screen for additional ligands to the OSGPR114 or OSGPR78 receptor using functional assays. The same assays, in the presence of a ligand, may be used to identify agonists or antagonists of the OSGPR114 or OSGPR78 receptor that may be employed for a variety of therapeutic purposes. It is well known to those in the art that the over-expression of a GPCR can result in the constitutive activation of intracellular signaling pathways. In the same manner, over-expression of the OSGPR114 or OSGPR78 receptor in any cell line as described above, can result in the activation of the functional responses described below, and any of the assays herein described can be used to screen for both agonist and antagonist ligands of the OSGPR114 or OSGPR78 receptor.

A wide spectrum of assays can be employed to screen for the presence of OSGPR114 or OSGPR78 receptor ligands. These assays range from traditional measurements of total inositol phosphate accumulation, cAMP levels, intracellular calcium mobilization, and potassium or sodium currents, for example; to systems measuring these same second messengers but which have been modified or adapted to be of higher throughput, more generic and more sensitive; to cell based assays reporting more general cellular events resulting from receptor activation such as metabolic changes, differentiation, cell division/proliferation. Description of several such assays follow.

Adenylate Cyclase/Cyclic AMP (cAMP) Assay

The adenylate cyclase assay is performed with an alpha-screen cAMP assay kit (Promega). The manufacturer's protocol is followed. Briefly, cells known to endogenously express moderate levels of OSGPR114 or OSGPR78 are lysed from the culture flask using a lysis buffer (0.1% BSA in PBS containing 20 mM rolipram and 0.54% TWEEN20), washed with PBS and diluted in assay buffer (0.1% BSA in PBS containing 20 mM rolipram) to a concentration of 600,000 cells/mL. White polystyrene 96-well plates are used for the assay. The following reagents are added to the wells: 5 mL forskolin (4× in assay buffer, $4 \times 10^{-4}$ M) or 5 µl assay buffer+ 5 mL LPA/vehicle control (LPA (4×) is dissolved in a 0.1% BSA in water solution)+5 mL acceptor beads (Stock solution is 90 mg/mL; 12 mL/0.5 mL stimulation buffer is used for the assay)+5 mL cells to initiate assay. The plate is incubated at room temperature for 30 min. For the standard cAMP curve used to quantify the data, 5 mL water+5 mL 4× cAMP in assay buffer+5 mL acceptor beads+5 mL cells are added to the plate. To terminate the assay, 10 µl of the donor beads solution is added (30 nM biotin-cAMP/60 mg streptavidin-donor beads in 1 mL lysis buffer). The plates are incubated overnight, protected from light. A Fusion-aHT counter was used to read the plates according to the kit's instructions.

In an alternative assay for measuring camp levels, a Cre-SEAP assay is used. HEK-293-Galpha16 cells stably expressing the cre-SEAP (cyclicAMP response element containing promoter driving expression of the secreted alkaline phosphatase gene) reporter construct, and transiently transfected with either the OSGPR114 or OSGPR78 vector or empty vector control, are grown to between ~$0.5 \times 10^6$ and $1 \times 10^7$ cells/dish and seeded at $4 \times 10^4$ cells/well on poly-D-lysine coated clear-bottom 96-well tissue culture plates. The cells are left to adhere to the plates in media for 24 h at 37° C. The media is aspirated and the cells arrested by serum starvation for a further 24 h in 200 mL of colorless DMEM.

After serum arrest, the starvation media is aspirated and 90 mL fresh colorless DMEM containing 0.1% BSA is added. 10 µL of 10× compound (or DMSO/H2O control) is added and the plates incubated at 37° C. for 7 h. Conditioned media (12.5 mL) is then transferred to a 96 well white flat-bottom plate. Next, 37.5 mL of 1× Tropix Dilution Buffer is added to the transferred culture media. 50 mL of Tropix Assay Buffer is also added. The plate is then incubated at room temperature for 5 minutes. Finally, 50 mL Tropix Reaction Buffer Diluent containing a 1:20 dilution of the CSPD Chemiluminescent Substrate is added. The plate is incubated at room temperature for 60 minutes and luminescence measured.

The receptor-mediated stimulation or inhibition of cyclic AMP (cAMP) formation by adenylate cyclase may also be assayed in cells expressing the receptors by the following assay. According to this method, cells are plated in 96-well plates or other vessels and preincubated in a buffer such as HEPES buffered saline (NaCl (150 mM), CaCl$_2$ (1 mM), KCl (5 mM), glucose (10 mM)) supplemented with a phosphodiesterase inhibitor such as 5 mM theophylline, with or without protease inhibitor cocktail (For example, a typical inhibitor cocktail contains 2 µg/mL aprotinin, 0.5 mg/mL leupeptin, and 10 µg/mL phosphoramidon.) for 20 min at 37° C., in 5% $CO_2$. Test compounds are added with or without 10 mM forskolin and incubated for an additional 10 min at 37° C. The medium is then aspirated and the reaction stopped by the addition of 100 mM HCl or other methods. The plates are stored at 4° C. for 15 min, and the cAMP content in the stopping solution is measured by radioimmunoassay. Radioactivity may be quantified using a gamma counter equipped with data reduction software. Specific modifications may be performed to optimize the assay for the receptor or to alter the detection method of cAMP.

According to a further method, cells are washed 2 times with HEPES buffered saline, as described above, and incubated overnight. On the day of the experiment, cells are washed 2 times with HEPES supplemented with a phosphodiesterase inhibitor such as 5 mM theophylline, with or without protease inhibitor cocktail (For example, a typical inhibitor cocktail contains 21 g/mL aprotinin, 0.5 mg/mL leupeptin, and 10 µg/mL phosphoramidon.) for 20 min at 37° C., in 5% $CO_2$. Test compounds are added with or without 10 mM forskolin and incubated for an additional 10 min at 37° C. The medium is then aspirated and the reaction stopped by the addition of 100 mM HCl or other methods. The plates are stored at 4° C. for 15 min, and the cAMP content in the stopping solution is measured by radioimmunoassay. Radioactivity may be quantified using a gamma counter equipped with data reduction software. Specific modifications may be performed to optimize the assay for the receptor or to alter the detection method of cAMP.

Arachidonic Acid Release Assay

Cells expressing the receptor are seeded into 96 well plates or other vessels and grown for 3 days in medium with supplements $^3$H-arachidonic acid (specific activity=0.75 µCi/mL) is delivered as a 100 µL aliquot to each well and samples are incubated at 37° C., 5% $CO_2$ for 18 hours. The labeled cells are washed three times with medium. The wells are then filled with medium and the assay is initiated with the addition of test compounds or buffer in a total volume of 250 µL. Cells are incubated for 30 min at 37° C., 5% $CO_2$. Supernatants are transferred to a microtiter plate and evaporated to dryness at 75° C. in a vacuum oven. Samples are then dissolved and resuspended in 25 µL distilled water. Scintillant (300 µL) is added to each well and samples are counted for $^3$H in a Trilux plate reader. Data are analyzed using nonlinear regression and statistical techniques available in the GraphPAD Prism package (San Diego, Calif.).

Inositol Phosphate Assay

OSGPR114 or OSGPR78 receptor-mediated activation of the inositol phosphate (IP) second messenger pathways can be assessed by radiometric measurement of IP products.

In a 96 well microplate format assay, cells are plated at a density of 70,000 cells per well and allowed to incubate for 24 hours. The cells are then labeled with 0.5 µCi [$^3$H]-myo-inositol overnight at 37° C., 5% $CO_2$. Immediately before the assay, the medium is removed and replaced with 90 µL of PBS containing 10 mM LiCl. The plates are then incubated for 15 min at 37° C., 5% $CO_2$. Following the incubation, the cells are challenged with agonist (10 µL/well; 10× concentration) for 30 min at 37° C., 5% $CO_2$. The challenge is terminated by the addition of 100 µL of 50% v/v trichloroacetic acid, followed by incubation at 4° C. for greater than 30 minutes. Total IPs are isolated from the lysate by ion exchange chromatography. Briefly, the lysed contents of the wells are transferred to a Multiscreen HV filter plate (Millipore) containing Dowex AG1-X8 (200-400 mesh, formate form). The filter plates are prepared adding 100 µL of Dowex AG1-X8 suspension (50% v/v, water: resin) to each well. The filter plates are placed on a vacuum manifold to wash or elute the resin bed. Each well is first washed 2 times with 200 µL of 5 mM myo-inositol. Total [$^3$H]inositol phosphates are eluted with 75 µL of 1.2M ammonium formate/0.1M formic acid solution into 96-well plates. 200 µL of scintillation cocktail is added to each well, and the radioactivity is determined by liquid scintillation counting.

Intracellular Calcium Mobilization Assays

The intracellular free calcium concentration may be measured by microspectrofluorimetry using the fluorescent indicator dye Fura-2/AM (Bush et. al., (1991) J. Neurochem. 57: 562-574). Cells expressing the receptor are seeded onto a 35 mm culture dish containing a glass coverslip insert and allowed to adhere overnight. Cells are then washed with HBS and loaded with 100 µL of Fura-2/AM (10 µM) for 20 to 40 min. After washing with HBS to remove the Fura-2/AM solution, cells are equilibrated in HBS for 10 to 20 min. Cells are then visualized under the 40× objective of a Leitz Fluovert FS microscope and fluorescence emission is determined at 510 nM with excitation wavelengths alternating between 340 nM and 380 nM. Raw fluorescence data are converted to calcium concentrations using standard calcium concentration curves and software analysis techniques.

In another method, the measurement of intracellular calcium can also be performed on a 96-well (or higher) format and with alternative calcium-sensitive indicators, preferred examples of these are: aequorin, Fluo-3, Fluo-4, Fluo-5, Calcium Green-1, Oregon Green, and 488 BAPTA. After activation of the receptors with agonist ligands the emission elicited by the change of intracellular calcium concentration can be measured by a luminometer, or a fluorescence imager; a preferred example of this is the fluorescence imager plate reader (FLIPR).

Cells expressing the receptor of interest are plated into clear, flat-bottom, black-wall 96-well plates (Costar) at a density of 80,000-150,000 cells per well and allowed to incubate for 48 hr at 5% $CO_2$, 37° C. The growth medium is aspirated and 100 µL of loading medium containing fluo-3 dye is added to each well. The loading medium contains: Hank's BSS (without phenol red) (Gibco), 20 mM HEPES (Sigma), 0.1 or 1% BSA (Sigma), dye/pluronic acid mixture (e.g. 1 mM Flou-3, AM (Molecular Probes) and 10% pluronic acid (Molecular Probes) mixed immediately before use), and 2.5 mM probenecid (Sigma) (prepared fresh). The cells are allowed to incubate for about 1 hour at 5% $CO_2$, 37° C.

During the dye loading incubation the compound plate is prepared. The compounds are diluted in wash buffer (Hank's BSS (without phenol red), 20 mM HEPES, 2.5 mM probenecid) to a 4× final concentration and aliquoted into a clear v-bottom plate (Nunc). Following the incubation the cells are washed to remove the excess dye. A Denley plate washer is used to gently wash the cells 4 times and leave a 100 µL final volume of wash buffer in each well. The cell plate is placed in the center tray and the compound plate is placed in the right tray of the FLIPR. The FLIPR software is setup for the experiment, the experiment is run and the data are collected. The data are then analyzed using an excel spreadsheet program. Antagonist ligands are identified by the inhibition of the signal elicited by agonist ligands.

For example, in one method employed herein, CHO and CHO-114 cells were seeded at a concentration of 50K cells/well in 200 mL growth media in clear, flat-bottom 96-well black assay plates and incubated overnight at 37 C. The growth media is aspirated from the cells and a dye solution (100 mL) added to each well. The dye solution consists of 2 mM probenecid, 2 mM HBSS, 10 mM Fluo-3 in a growth media minus antibiotics solution. The cells are loaded with the dye for 1 h at 37 C before aspiration and rinsing with wash buffer (20 mM HBSS+2 mM Probenecid). Compound plates are then prepared with 4× compound/control. 150 ul of wash buffer is added to each well. Once the FLIPR is fully calibrated, compound is added to the plate and the release of calcium measured using 0.4 exposure length and a laser set at 0.3 W.

GTPγS Functional Assay

Membranes from cells expressing the receptor are suspended in assay buffer (e.g., 50 mM Tris, 100 mM NaCl, 5 mM $MgCl_2$, 10 µM GDP, pH 7.4) with or without protease inhibitors (e.g., 0.1% bacitracin). Membranes are incubated on ice for 20 minutes, transferred to a 96-well Millipore microtiter GF/C filter plate and mixed with GTP.γ$^5$S (e.g., 250,000 cpm/sample, specific activity .about.1000 Ci/mmol) plus or minus unlabeled GTPγS (final concentration= 100 µM). Final membrane protein concentration.apprxeq. 90 µg/mL. Samples are incubated in the presence or absence of test compounds for 30 min. at room temperature, then filtered on a Millipore vacuum manifold and washed three times with cold (4° C.) assay buffer. Samples collected in the filter plate are treated with scintillant and counted for $^{35}$S in a Trilux (Wallac) liquid scintillation counter. It is expected that optimal results are obtained when the receptor membrane preparation is derived from an appropriately engineered heterologous expression system, i.e., an expression system resulting in high levels of expression of the receptor and/or expressing G-proteins having high turnover rates (for the exchange of GDP for GTP). GTPγS assays are well-known to those skilled in the art, and it is contemplated that variations on the method described above, such as are described by Tian et al. (1994) Molecular Pharm. 45: 524-553 or Lazareno and Birdsall (1993) Br. J. Pharmacol. 109: 1120-1127, may be used.

Alternatively, high affinity [$^{35}$S]-GTPγS binding assays are performed in 96-well format using a method modified from Wieland and Jakobs (Wieland, T. & Jakobs, K. H. (1994) Method. Enzymol. 237: 3-13). Membranes (10 µg per point) are diluted to about 0.1 mg/mL in assay buffer (20 mM HEPES, 100 mM NaCl, 10 mM $MgCl_2$, pH7.4) supplemented with saponin (10 mg/l) and pre-incubated with 40 µM GDP. Various concentrations of ligand (e.g. LPA) are added, followed by [$^{35}$S]-GTPγS (~1200 Ci/mmol, Amersham) at 0.3 nM (total vol. of 100 [d) and binding is allowed to proceed at room temperature for 30 min. Non-specific binding is determined by the inclusion of 0.6 mM GTP. Wheatgerm agglutinin SPA beads (Amersham; 0.5 mg) in 25/L assay buffer are added and the whole is incubated at room temperature for 30 min with agitation. Plates are centrifuged at 1500 g for 5 min and bound [$^{35}$S]-GTPγS is determined by scintillation counting.

Alternatively, instead of [$^{35}$S]-GTPγS, a time-resolved fluorescence based GTP binding assay using a non-radioactive, non-hydrolyzable GTP analog such as GTP-Eu (Perkin Elmer™) can be employed.

Furthermore, several methods that increase the utility of such assays outside of the pertussis-toxin-sensitive G-proteins can be employed. Methods involving the expression of GPCRs, and also G proteins of interest, in various insect cell lines that express low levels of G-protein orthologues can be used (e.g. see Windh, R. T. and Manning, D. R. (2002) Methods Enzymol. 344:3-14). Introduction of a GPCR and a mammalian G protein into such cells using baculoviral-based expression vectors can provide high signal to background in [$^{35}$S]-GTPγS binding assays. Immunocapture of [$^{35}$S]-GTPγS-bound G-proteins and GPCR-G-protein fusion proteins can also be employed to enhance signal to background (e.g. see Milligan, G. (2003) Trends in Pharmacol. Sci. 24:87-90).

For example, in one method employed herein, membranes from untransfected CHO cells as well as OSGPR114 stable clones were prepared using the method described by Griffin et al (1998). Membranes were homogenized in buffer containing 50 mM Tris, 3 mM MgCl2, 100 mM NaCl, 1 mM EDTA, 1 uM GDP, 0.1% fatty acid free BSA, 0.01% Saponin, pH 7.4.

Assays were carried out in a reaction mixture containing 50 mL of membrane suspension (~5 mg/well), 50 mL of [$^{35}$S]-GTPgS binding (final concentration ~0.5 nM: 50 mL aliquot counted to determine precise concentration employed) and either 50 mL of assay buffer, 50 mL of unlabeled GTPgS (defining nonspecific binding: final concentration is 10 mM) or 50 mL of each concentration of LPA. Incubations were carried out in triplicate for 60 minutes at 37° C. Reactions were terminated by rapid filtration over GF/B filters presoaked in ice cold wash buffer for 90 minutes. The filters were then washed 6 times with 0.3 mL of ice cold wash buffer
(50 mM Tris, 5 mM MgCl2, pH 7.4). The filters were dried, covered with Microscint-20, dark adapted for 5 minutes, and counted on a 2 minute [35S] protocol on a Packard TopCount LSC.

Microphysiometric Assay

Because cellular metabolism is intricately involved in a broad range of cellular events (including receptor activation of multiple messenger pathways), the use of microphysiometric measurements of cell metabolism can in principle provide a generic assay of cellular activity arising from the activation of any receptor regardless of the specifics of the receptor's signaling pathway (Williams, C. (2000) Current Opinion Biotech. 11:42-46).

General guidelines for transient receptor expression, cell preparation and microphysiometric recording are described elsewhere (Salon, J. A. and Owicki, J. A., (1996) Meth. Neurosci. 25: 201-224). Typically cells expressing receptors are harvested and seeded at 3×10$^5$ cells per microphysiometer capsule in complete media 24 hours prior to an experiment. The media is replaced with serum free media 16 hours prior to recording to minimize non-specific metabolic stimulation by assorted and ill-defined serum factors. On the day of the experiment the cell capsules are transferred to the microphysiometer and allowed to equilibrate in recording media (low buffer RPMI 1640, no bicarbonate, no serum (Molecular Devices Corporation, Sunnyvale, Calif.) containing 0.1% fatty acid free BSA), during which a baseline measurement of basal metabolic activity is established.

A standard recording protocol specifies a 100 μL/min flow rate, with a 2 min total pump cycle which includes a 30 sec flow interruption during which the acidification rate measurement is taken. Ligand challenges involve a 1 min 20 sec exposure to the sample just prior to the first post challenge rate measurement being taken, followed by two additional pump cycles for a total of 5 min 20 sec sample exposure. Typically, drugs in a primary screen are presented to the cells at 10 μM final concentration. Follow up experiments to examine dose-dependency of active compounds are then done by sequentially challenging the cells with a drug concentration range that exceeds the amount needed to generate responses ranging from threshold to maximal levels. Ligand samples are then washed out and the acidification rates reported are expressed as a percentage increase of the peak response over the baseline rate observed just prior to challenge.

MAP Kinase Assay

MAP kinase (mitogen activated kinase) may be monitored to evaluate receptor activation. MAP kinase is activated by multiple pathways in the cell. A primary mode of activation involves the ras/raf/MEK/MAP kinase pathway. Growth factor (tyrosine kinase) receptors feed into this pathway via SHC/Grb-2/SOS/ras. Gi coupled receptors are also known to activate ras and subsequently produce an activation of MAP kinase. Receptors that activate phospholipase C (such as Gq/G11-coupled) produce diacylglycerol (DAG) as a consequence of phosphatidyl inositol hydrolysis. DAG activates protein kinase C which in turn phosphorylates MAP kinase.

MAP kinase activation can be detected by several approaches. One approach is based on an evaluation of the phosphorylation state, either unphosphorylated (inactive) or phosphorylated (active). The phosphorylated protein has a slower mobility in SDS-PAGE and can therefore be compared with the unstimulated protein using Western blotting. Alternatively, antibodies specific for the phosphorylated protein are available (New England Biolabs) which can be used to detect an increase in the phosphorylated kinase. In either method, cells are stimulated with the test compound and then extracted with Laemmli buffer. The soluble fraction is applied to an SDS-PAGE gel and proteins are transferred electrophoretically to nitrocellulose or Immobilon. Immunoreactive bands are detected by standard Western blotting technique. Visible or chemiluminescent signals are recorded on film and may be quantified by densitometry.

Another approach is based on evaluation of the MAP kinase activity via a phosphorylation assay. Cells are stimulated with the test compound and a soluble extract is prepared. The extract is incubated at 30° C. for 10 min with γ-$^{32}$P-ATP, an ATP regenerating system, and a specific substrate for MAP kinase such as phosphorylated heat and acid stable protein regulated by insulin, or PHAS-I. The reaction is terminated by the addition of $H_3PO_4$ and samples are transferred to ice. An aliquot is spotted onto Whatman P81 chromatography paper, which retains the phosphorylated protein. The chromatography paper is washed and counted for $^{32}$P in a liquid scintillation counter. Alternatively, the cell extract is incubated with γ$^{32}$P ATP, an ATP regenerating system, and biotinylated myelin basic protein bound by streptavidin to a filter support. The myelin basic protein is a substrate for activated MAP kinase. The phosphorylation reaction is carried out for 10 min at 30° C. The extract can then by aspirated through the filter, which retains the phosphorylated myelin basic protein. The filter is washed and counted for $^{32}$P by liquid scintillation counting.

Cell Proliferation Assay

Receptor activation of the receptor may lead to a mitogenic or proliferative response which can be monitored via $^3$H-thymidine uptake. When cultured cells are incubated with $^3$H-thymidine, the thymidine translocates into the nuclei where it is-phosphorylated to thymidine triphosphate. The nucleotide triphosphate is then incorporated into the cellular DNA at a rate that is proportional to the rate of cell growth. Typically, cells are grown in culture for 1-3 days. Cells are forced into quiescence by the removal of serum for 24 hrs. A mitogenic agent is then added to the media. Twenty-four hours later, the cells are incubated with $^3$H-thymidine at specific activities ranging from 1 to 10 μCi/mL for 2-6 hrs. Harvesting procedures may involve trypsinization and trapping of cells by filtration over GF/C filters with or without a prior incubation in TCA to extract soluble thymidine. The filters are processed with scintillant and counted for $^3$H by liquid scintillation counting. Alternatively, adherent cells are fixed in MeOH or TCA, washed in water, and solubilized in 0.05% deoxycholate/0.1 N NaOH. The soluble extract is transferred to scintillation vials and counted for $^3$H by liquid scintillation counting.

Alternatively, cell proliferation can be assayed by measuring the expression of an endogenous or heterologous gene product, expressed by the cell line used to transfect the receptor, which can be detected by methods such as, but not limited to, florescence intensity, enzymatic activity, immunoreactivity, DNA hybridization, polymerase chain reaction, etc.

Assays for Chemotactic Cell Motility and Chemoinvasion

Chemoinvasion is measured by the ability of tumor cells to migrate through a thick layer of MATRI-GEL during a prolonged incubation period (70 hours). This property is distinct from chemotactic cell motility, which involves a much shorter incubation period (20 hours) and a thin layer of MATRI-GEL.

Assays are performed using transwell plates with polycarbonate membrane filters (pore size 8 µm) (Costar Scientific, Cambridge, Mass.). 50 µL aliquots of an aqueous solution of MATRI-GEL (Collaborative Research, Bedford, Mass.) containing 20 µg/mL (for chemotactic motility assay) or 200 µg/mL (for chemoinvasion assay) are added to each well and dried overnight. The filter is fitted onto the lower chamber plate. The lower chamber contains 0.6 mL medium containing a moltility factor, with or without the compound with activity on OSGPR114 or OSGPR78. To the upper chamber is added 100 µL of cell suspension ($5 \times 10^4$ cells/mL for invasion assay, $5 \times 10^5$ cells/mL for motility assay), which is then incubated in 5% $CO_2$ at 37° C. for 70-72 hours (invasion assay) or 20 hours (motility assay). After incubation, cells remaining in the upper chamber are wiped off with a cotton swab, and cells which had migrated to the lower chamber side of the filter are fixed in methanol for 30 seconds and stained with 0.05% toluidine blue. The filter is removed, the stain was solubilized in 10% acetic acid (0.1 mL for invasion assay, 0.5 mL for motility assay), and color intensity (optical density) is quantitated by ELISA reading at 630 nm. A linear relationship is observed between cell number and toluidine blue optical density.

Promiscuous Second Messenger Assays

It is not possible to predict, a priori and based solely upon the GPCR sequence, which of the cell's many different signaling pathways any given receptor will naturally use. It is possible, however, to coax receptors of different functional classes to signal through a pre-selected pathway through the use of promiscuous G-alpha. subunits. For example, by providing a cell based receptor assay system with an endogenously supplied promiscuous G-alpha subunit such as G-alpha$_{15}$ or G-alpha$_{16}$ (i.e. $G_{15}$ or $G_{16}$) or a chimeric G-alpha subunit such as G-alpha$_{qz}$, a GPCR, which might normally prefer to couple through a specific signaling pathway (e.g., $G_s$, $G_t$, $G_q$, $G_o$, etc.), can be made to couple through the pathway defined by the promiscuous Galpha subunit and upon agonist activation produce the second messenger associated with that subunit's pathway. In the case of G-alpha$_{15}$, G-alpha$_{16}$ and/or G-alpha$_{qz}$ this would involve activation of the $G_q$ pathway and production of the second messenger $IP_3$. Through the use of similar strategies and tools, it is possible to bias receptor signaling through pathways producing other second messengers such as $Ca^{2+}$, cAMP, and $K^+$ currents, for example (Milligan, G. and Rees, S. (1999) TIPS 20:118-124).

It follows that the promiscuous interaction of the exogenously supplied G-alpha subunit with the receptor alleviates the need to carry out a different assay for each possible signaling pathway and increases the chances of detecting a functional signal upon receptor activation.

Methods for Recording Currents in *Xenopus* Oocytes

Oocytes are harvested from *Xenopus laevis* and injected with mRNA transcripts as previously described (Quick, M. W. and Lester, H. A., (1994) Meth. Neurosci. 19: 261-279; Smith et. al. (1997) J. Biol. Chem. 272: 24612-24616). The test receptor of this invention and G-alpha. subunit RNA transcripts are synthesized using the T7 polymerase ("Message Machine," Ambion) from linearized plasmids or PCR products containing the complete coding region of the genes. Oocytes are injected with 10 ng of synthetic receptor RNA and incubated for 3-8 days at 17 degrees. Three to eight hours prior to recording, oocytes are injected with 500 pg promiscuous G-alpha subunits mRNA in order to observe coupling to $Ca^{2+}$ activated Cl-currents. Dual electrode voltage clamp (Axon Instruments Inc.) is performed using 3 M KCl-filled glass microelectrodes having resistances of 1-2 MOhm. Unless otherwise specified, oocytes are voltage clamped at a holding potential of −80 mV. During recordings, oocytes are bathed in continuously flowing (1-3 mL/min) medium containing 96 mM NaCl, 2 mM KCl, 1.8 mM $CaCl_2$, 1 mM $MgCl_2$, and 5 mM HEPES, pH 7.5 (ND96). Drugs are applied either by local perfusion from a 10 µL glass capillary tube fixed at a distance of 0.5 mm from the oocyte, or by switching from a series of gravity fed perfusion lines.

Other oocytes may be injected with a mixture of receptor mRNAs and synthetic mRNA encoding the genes for G-protein-activated inward rectifier channels (GIRK1 and GIRK4, U.S. Pat. Nos. 5,734,021 and 5,728,535 or GIRK1 and GIRK2) or any other appropriate combinations (see, e.g., Inanobe, A. et. al. (1999) J. of Neurosci. 19(3): 1006-1017). Genes encoding G-protein inwardly rectifying $K^+$ (GIRK) channels 1, 2 and 4 (GIRK1, GIRK2, and GIRK4) may be obtained by PCR using the published sequences (Kubo, Y. et al., Nature 364:802-806 (1993); Dascal et al., Proc. Natl. Acad. Sci. USA 90:10235-10239 (1993); Krapivinsky et. al., Nature 374:135-141 (1995) and J. Biol. Chem. 270:28777-28779 (1995)) to derive appropriate 5' and 3' primers. Human heart or brain cDNA may be used as template together with appropriate primers.

Heterologous expression of GPCRs in *Xenopus* oocytes has been widely used to determine the identity of signaling pathways activated by agonist stimulation (Gundersen, C. B. et al. (1983), Proc. R. Soc. Lond. B. Biol. Sci. 219(1214): 103-109; Takahashi et al. (1987), Proc. Natl. Acad. Sci. USA 84(14):5063-5067). Activation of the phospholipase C(PLC) pathway is assayed by applying a test compound in ND96 solution to oocytes previously injected with mRNA for the OSGPR114 or OSGPR78 receptor and observing inward currents at a holding potential of approximately −80 mV. The appearance of currents that reverse at −25 mV and display other properties of the Ca2+-activated Cl-channel is indicative of receptor-activation of PLC and release of $IP_3$ and intracellular $Ca^{2+}$. Such activity is exhibited by GPCRs that couple to Gq or $G_{11}$.

Involvement of the Gi/o class of G-proteins in GPCR-stimulated Ca2+-activated Cl-currents is evaluated using PTX, a toxin which inactivates Gi/o G-proteins. Oocytes are injected with 25 ng PTX/oocyte and modulation of Ca2+-activated Cl-currents by OSGPR114 or OSGPR78 receptor is evaluated 2-5 h subsequently.

Elevation of intracellular cAMP can be monitored in oocytes by expression of the cystic fibrosis transmembrane conductance regulator (CFTR) whose Cl⁻-selective pore opens in response to phosphorylation by protein kinase A (Riordan, J. R. (1993) Ann. Rev. Physiol. 55: 609-630). In order to prepare RNA transcripts for expression in oocytes, a template is created by PCR using 5' and 3' primers derived from the published sequence of the CFTR gene (Riordan, J. R. (1993) Ann. Rev. Physiol. 55: 609-630). The 5' primer includes the sequence coding for T7 polymerase so that transcripts can be generated directly from the PCR products without cloning. Oocytes are injected with 10 ng of CFTR mRNA in addition to 10-15 ng mRNA for OSGPR114 or OSGPR78. Electrophysiological recordings are made in ND96 solution after a 2-3 day incubation at 18° C. Currents are recorded under dual electrode voltage clamp (Axon Instruments Inc.) with 3 M KCl-filled glass microelectrodes having resistances of 1-2 Mohm. Unless otherwise specified, oocytes are voltage clamped at a holding potential of −80 mV. During recordings, oocytes are bathed in continuously flowing (1-3 mL/min) medium containing 96 mM NaCl, 2 mM KCl, 1.8 mM $CaCl_2$, 1 mM MgCl$_2$, and 5 mM HEPES, pH 7.5 (ND96). Drugs are applied either by local perfusion from a 10 μL glass capillary tube fixed at a distance of 0.5 mm from the oocyte, or by switching from a series of gravity fed perfusion lines.

Activation of G-protein G$_i$ and G$_o$ can be monitored by measuring the activity of inwardly rectifying K$^+$ (potassium) channels (GIRKs). Activity may be monitored in oocytes that have been co-injected with mRNAs encoding the mammalian receptor plus GIRK subunits. GIRK gene products co-assemble to form a G-protein activated potassium channel known to be activated (i.e., stimulated) by a number of GPCRs that couple to G$_i$ or G$_o$ (Kubo, Y. et al. (1993), Nature 364:802-806; Dascal et al. (1993), Proc. Natl. Acad. Sci. USA 90:10235-10239). Oocytes expressing the mammalian receptor plus the GIRK subunits are tested for test compound responsivity by measuring K$^+$ currents in elevated K$^+$ solution containing 49 mM K$^+$.

Results and Discussion

Cloning of the Full Length Sequences of OSGPR114 and OSGPR78

The human OSGPR114 receptor shares the highest amino acid homology with human OSGPR78 (36%), and 29% with the P2Y5-like (P2Y9) receptor described by Janssens (Janssens et. al. (1997) Biochem. Biophys. Res. Commun. 236(1): 106-112). OSGPR78 shared a 56% homology with this P2Y9 receptor. OSGPR114 and OSGPR78 receptors are only distantly related to other known LPA receptors. Homology clustering analysis with OSGPR114 and OSGPR78 indicates that they align most closely with each other, and the closest relatives from the known superfamily of GPCR are the P2Y nucleotide receptors, the cysteinyl leukotriene receptors and the platelet-activating factor (PAF) receptor.

Expression Profiling Analysis

Gene expression analysis, by quantitative RT-PCR, indicates that there is a wide expression of OSGPR114 in normal human tissues (FIG. 13). The highest expression levels (normalized to TFIIB expression) were observed in the kidney, leukocytes, lung and aorta, with lower additional expression in the liver, pancreas, adipose tissue, cerebellum, hippocampus, small intestine, trachea, thymus, bladder and ovary. Expression of the receptor in other tissues was low relative to these levels, but detectable in all tissues tested.

Gene expression analysis, by quantitative RT-PCR, indicates that there is a high and almost ubiquitous expression of OSGPR78 in normal human tissues (FIG. 13). High expression levels (normalized to TFIIB expression) were observed in all tissues tested, and especially high in peripheral tissues and cells involved in the immune system. The prostate showed the highest expression level in this particular experiment.

It is perhaps not surprising that LPA specific GPCRs are found extensively throughout the body, due to the known role of LPA in modulating a vast variety of physiological processes, including growth and differentiation of cells. The distribution patterns of both OSGPR78 and OSGPR114 are therefore in correlation with the known biological activities of the activating molecule. Similarly, the observation that LPA synthesizing enzymes, and LPA binding proteins, are found free in the circulation and therefore can theoretically deliver LPA to any part of the body, is further consistent with this hypothesis.

A number of human cancer cell lines were also tested for expression of OSGPR114 and OSGPR78, and found to express the receptors (FIG. 3). Cancer cell lines derived from the following tissues of origin were found to express OSGPR114: colon (T84, SW480, LoVo and HCT8), breast (DU4775 and T47D), testicular (577MF) and pancreatic (ASPC-1, Cappan2, CFPAC, HPAFII and Panc1). Cancer cell lines derived from the following tissues of origin were found to express OSGPR78: Brain (T98G), Leukemia (HL60), breast (MDA-MB-435, mcf7, T47D), bladder (AII63, T24), colon (HT29), GI tract (cappan1), pancreatic (ASPC-1, BXPC, Cappan2) and liver (HepG2).

In order to further characterize the expression of OSGPR78 and OSGPR114 in tumors, the expression of these receptors was measured in matched pairs of tumor samples using RT-PCR (FIGS. 4 and 5). The matched pairs were all generated from internal tissue samples, with the exception of a colon matched pair tumor sample purchased directly from Clontech (ID#). Expression of OSGPR78 was observed to be upregulated in 5/8 colon samples with no change in 3/8. OSGPR78 was also upregulated in 2/7 and 2/9 breast and lung samples respectively, with no change observed in the remaining samples. Gene expression of OSGPR114 also showed upregulation in certain matched pairs of tumor samples. OSGPR114 was upregulated in 5/9 lung, 4/7 breast and 4/8 colon samples, with no change in the other samples tested. The demonstration that in over 50% of the cancer matched pairs tested in this study, OSGPR114 gene expression demonstrates the likely importance of this receptor to a variety of cancer types. OSGPR78 gene expression was also increased in greater than 50% of colon cancers tested, with a smaller percentage of breast and colon tumor samples also showing increased gene expression. These particular cancer types were tested due to the number of studies implicating LPA signaling in colon, lung and breast cancers.

In summary, the pattern of gene expression of OSGPR114 and OSGPR78 in malignant cell lines, and in particular, the over-expression of the receptor gene in matched pairs of tumor sample RNAs strongly implicates these genes in the disease of cancer. This observation is consistent with previous demonstrations of increased LPA signaling in cancer. It is therefore highly plausible that the increased LPA signaling seen in carcinogenesis and disease progression is the result of increased LPA signaling through OSGPR114 and OSGPR78 and that moieties which can block the effects of LPA at these receptors would be of therapeutic benefit for the treatment of a range of cancer types. Such receptor antagonists may take the form of small molecules, peptides or antibodies that block the receptor directly, or a downstream target in the OSGPR114 and/or OSGPR78 signaling pathway.

Yeast-Based Reporter Assays

Figure 7:
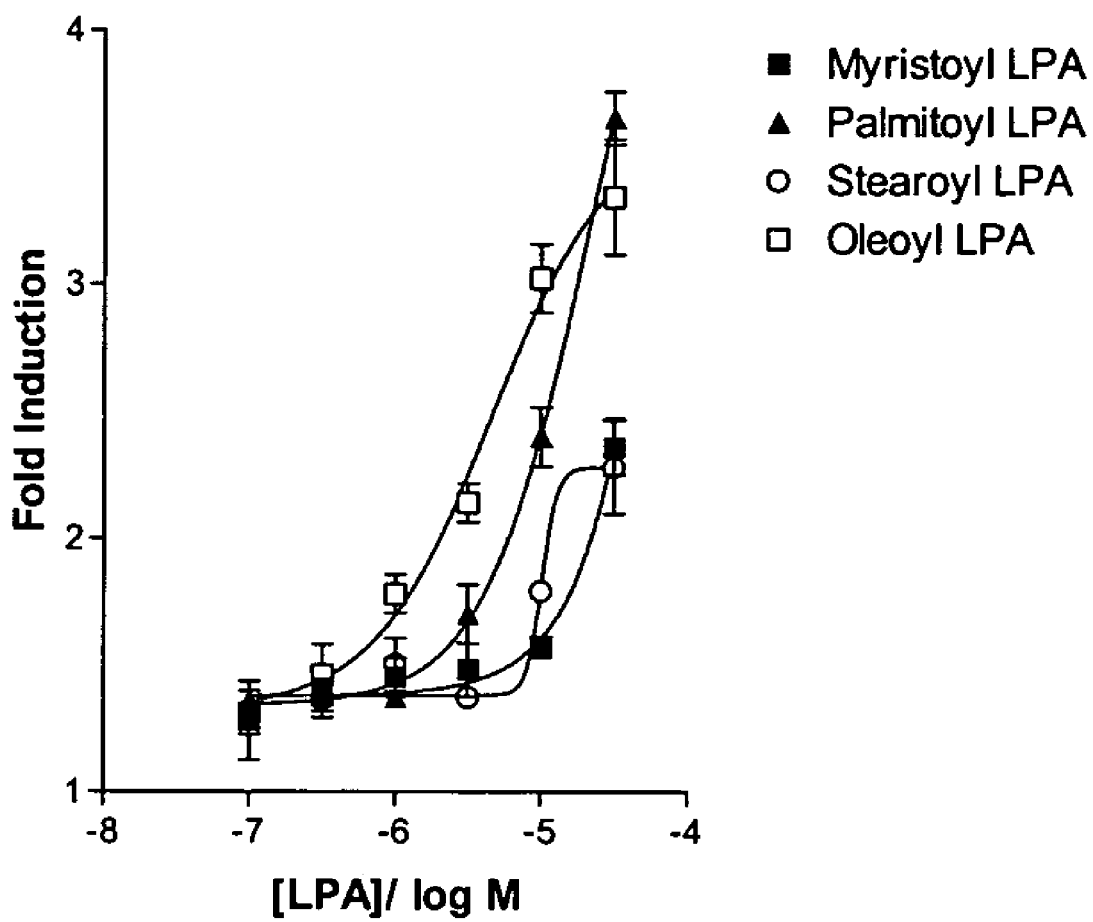
FIG. 7: Effects of different LPA species at OSGPR114. The experiment was conducted as detailed in the Materials and Methods section. Briefly, engineered yeast cells expressing a Galpha chimeric subunit and two reporter genes, URA-Fus1p-LacZ and TRP-Fus1p-LacZ were incubated with LPA. The yeast cells were tested with and without OSGPR114 expression. β-galactosidase activity was measured and the result expressed as a fold-induction over basal β-galactosidase activity. LPA stimulation of fluorescence was only observed in receptor transformed yeast cells and not in vector transformed yeast cells or in yeast cells of similar chimeric backgrounds expressing other receptors.
Figure 8:
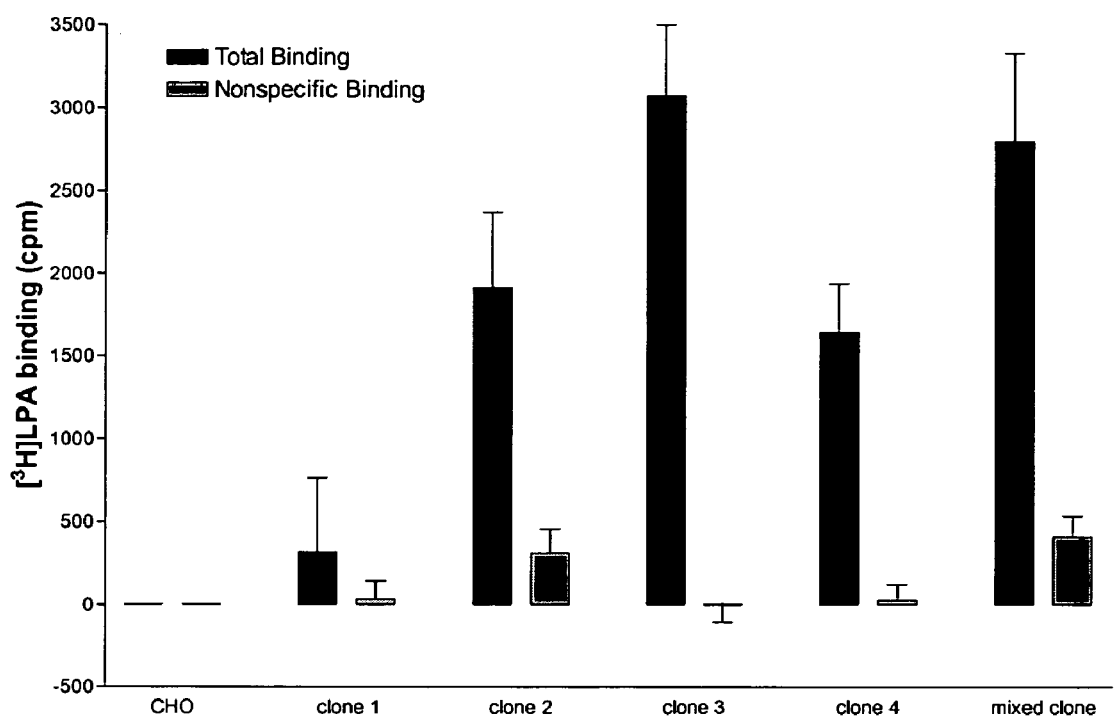
FIG. 8: Specific binding of [3H]LPA (14 nM) in cell membranes derived from OSGPR114-stably tranfected CHO-K1 cells. The experiment was conducted as described in the Materials and Methods section and the data are shown are the result of subtracting CHO-K1 parental cell membrane specific binding from CHO-OSGPR114 specific binding.

Co-expression of the receptor and the reporter genes in yeast imparts a triple selection benefit to the yeast, allowing them to grow in a LEU-URA-TRP deficient media. Colonies that grew on SD-LUT(−) plates, and therefore expressed the plasmids of interest, were tested in the fluorogenic β-galactosidase assay. Due to the homology clustering analysis that indicated that the closest relatives of this orphan GPCR were nucleotide receptors, PAF receptor and leukotriene receptors, various nucleotides, leukotrienes, PAF and related endogenously found biologically active lipids were tested at OSGPRs 114 and 78. Additionally, the prior art had suggested that the nucleotide ADP specifically activates this receptor, and so this compound was also tested in the assay. ADP and ATP were found to have no effect in the yeast-based assay, nor did other nucleotides, PAF, leukotrienes and various other phospholipids and lysophospholipids. However, lysophosphatidic acid (LPA), with a number of lipid backbones (myristoyl, palmitoyl, stearoyl and oleoyl) were all shown to cause an increase in fluorescence in yeast transformed with OSGPR114 or OSGPR78 receptor (FIGS. 6 and 7), but not in vector transformed cells. Oleoyl LPA was the most efficacious and potent of the compounds tested in both the OSGPR78 assay and the OSGPR114 assay.

Multiple yeast strains with different G-protein chimeras were also tested for optimal response to oleoyl LPA and several but not all strains responded to ligand induction. This is normal. Generally, the G alpha chimeras have been designed to mimic mammalian receptors as closely as possible. In a mammalian system, receptors which couple to Galpha i/o family generally will not respond in a Galpha q based read-out. It was found that using the yeast assay chimeras of Galpha q (20156), and Galphas (20202) could produce a response to oleoyl LPA in OSGPR114-transformed yeast. Members of the Galpha i and Galpha 12/13 family chimeras were optimal for LPA response in OSGPR78-transformed yeast (13393, 15074, 13395) (FIG. 6). 20156 and 20202 represent internal nomenclature for yeast expressing sandwich chimeras of the G alpha q and s families and 13393 represents a Galpha chimera which contains the GPA1 with the five terminal amino acids of mammalian Galpha i2. 13395 represents GPA1 with the five terminal amino acids from mammalian Galpha12 and 15074 represents GPA1 with the five terminal amino acids from mammalian Galpha13. The sandwich chimers represent N- and C-terminal sections of the mammalian Galpha, fused to a middle section of the endogenous Galpha from yeast (GPA1). Vector controls in the same yeast strains did not respond to oleoyl LPA, nor did other GPCR expressed in the comparable chimeric yeast backgrounds. Comparison between the OSGPR78 and OSGPR114 demonstrate that, despite the relatively low homology between the receptors, the pharmacology of the receptors was almost identical with respect to the compounds tested in this study.

In summary, OSGPR114 and OSGPR78, when expressed in yeast respond to LPA. This is in contrast to some previous studies (Webb et. al. (1996) Biochem. Biophys. Res. Commun. 219(1):105-110) that suggested the possibility that certain nucleotides may activate OSGPR78. This possibility was not confirmed in our studies, or in other published studies (Li et. al. (1997) Biochem. Biophys. Res. Commun. 236(2):455-60). In terms of efficacy and potency, the optimal endogenously produced agonist tested oleoyl-LPA. The identification of novel receptors that are activated by oleoyl LPA, and other LPA analogs, allows for a speculation as to the potential role of these receptors in the body. Based on our understanding of the physiological effects of LPA and its role in cell growth, differentiation, motility, metastasis, invasion, artherosclerosis, obesity, cardiovascular and respiratory regulation, OSGPR114 and OSGPR78 represent molecular mechanisms by which these effects of LPA in the body may be mediated and therefore act as unique targets for therapeutic intervention in the relevant diseases.

Mammalian Cell Based Assays

Radioligand Binding

Stable transfection of CHO cells with OSGPR114 led to increased specific [3H] oleoyl LPA binding (14 nM) compared to CHO cells transfected with vector alone. The CHO cell membranes control did however demonstrate specific LPA binding. However, when the data are normalized to the CHO cells, the CHO-OSGPR114 membranes demonstrated a significant level of specific LPA binding, suggesting that the radiolabeled LPA was binding to OSGPR114. The CHO-OSGPR114 clone which exhibited the highest level of LPA specific binding, which was also the clone that exhibited the highest level of OSGPR114 mRNA expression was used for subsequent experimentation. The demonstration that OSGPR114 stably transfect CHO cells exhibit significantly higher specific [3H] LPA binding extends the observation from the yeast-based assays that LPA binds to OSGPR114.

The data also demonstrate that CHO cells contain an as yet unidentified form of LPA receptor, which may or may not be one of the known LPA receptors (the hamster homolog).

B) GTPγS Binding

Membranes prepared from the CHO and CHO-OSGPR114 stable transfectants were tested for responses to LPA in the GTPγS binding assay. The GTPγS binding assay is an assay that has proved of high utility for measuring the activation, and antagonism, of GPCR, particularly those receptors which couple to the Gi/o family of G-proteins. Oleoyl LPA, at concentrations from 1 nM to 300 nM was applied to membranes from each of the cell lines. LPA produced concentration-response curves in both CHO membranes and in the stably transfected CHO-OSGPR114 membranes. The observation that the CHO parental cell also produces a LPA dependent concentration response curve in the GTPγS binding assay confirms that the unidentified receptor shown to be present in these membranes in the radioligand binding assay is a GPCR. However, the EC50 value of LPA calculated in the CHO-OSGPR114 stable transfectants was significantly different to the parental CHO membranes, suggesting that LPA activated OSGPR114, as well as the endogenous CHO receptor, and with a higher potency. The EC50 values in the CHO-OSGPR114 and CHO membranes were 137 and 768 nM respectively, with comparable Emax values.

C) FLIPR Assay

CHO, or CHO-OSGPR114, cells were tested in a FLIPR assay, a technique frequently used to measure changes in intracellular calcium concentrations in response to GPCR activation. LPA was added to the cells in the presence or absence of pertussis toxin. Pertussis toxin is an agent known to ADP-ribosylate and thus inactivate members if the Gi/o family of G-proteins and has been frequently used to assess whether G-proteins of this family are involved in the signal transduction pathway of a particular GPCR. In the FLIPR assay, no significant change in intracellular calcium concentration was observed on response to LPA administration in the CHO cells. However, LPA caused a concentration-dependent response in the CHO-OSGPR114 cells with an EC50 of 59 nM, a figure in close agreement with that observed in the GTPγS binding assay. Co-addition of pertussis toxin completely abolished this effect. This result demonstrates that activation of OSGPR114 by LPA can cause an increase in intracellular calcium concentration, an effect mediated by G-proteins of the Gi/o family as indicated by the sensitivity to pertussis toxin.

In summary, the results of the cell and membrane-based assays using expression of OSGPR114 in mammalian cells further confirms the specificity of the response observed in yeast, that OSGPR114 is a novel specific LPA receptor. Interestingly, most of the mitogenic and motogenic responses of LPA in the majority of cell-based assays have demonstrated that the effects of LPA on proliferation and motility are regulated by Gi/o coupled receptors. In proving that OSGPR114 also is a Gi/o coupled LPA-specific receptor lends further weight to the proposal that OSGPR114 is likely to be an important molecular regulator of LPA effects on cell proliferation and motility, enhancing the rationale for its use as a target for anti-cancer therapeutics.

OSGPR114 and OSGPR78 could not have been predicted to be activated by LPA through analysis of the DNA or amino acid sequences of the receptors. They have a very low homology to the known LPA receptors (LPA1-3) and homology-clustering analysis of known and orphan GPCRs, a technique that can be predictive of ligand-receptor coupling systems (Joost and Methner, (2002) Genome Biol. 3(11): research 0063.1-0063.16 (at GenomeBiology website); Vaidehi et. al. (2002) Proc. Natl. Acad. Sci. USA. 99(20):12622-12627), does not demonstrate any predictable relationship between the known LPA receptors and OSGPR114 and OSGPR78. Indeed, a clustering analysis demonstrates that the two closely related GPCR OSGPR114 and OSGPR78 receptors cluster with nucleotide receptors such as the P2Y family and the PAF receptor.

Role of OSGPR114 and OSGPR78 in Cancer Cells

Assessment of the validity of OSGPRs 114 and 78 as cancer targets was approached in three ways. Firstly, in cell lines shown to express the receptors, the effects of LPA on growth and survival was assessed. Secondly, small interfering RNAs (siRNA) specific for the receptors was introduced to cells expressing OSGPR114 and/or OSGPR78 and the effect on cell proliferation/survival measured. Finally, in cells known to express the receptors, the signaling pathways activated by LPA were investigated.

Summary of Results:

In serum-free conditions, LPA induced cellular proliferation and prevented apoptosis of H CT-8 cells, a colon cancer cell line known to express high levels of OSGPR114.

i) Specific siRNAs targeting OSGPR114 inhibited cellular proliferation of all cell lines tested. This growth inhibition was dependent only on the expression of OSGPR114 and not on the presence of other known LPA receptors in these cells. Associated with this growth inhibition in most of the cell lines was an induction of apoptosis.

ii) Specific siRNAs targeting OSGPR78 inhibited cellular proliferation in most cell lines tested. Within a subset of these cell lines, apoptosis was also induced by the introduction of OSGPR78 siRNA 3) In HCT-8 cells, and using activation-specific antibodies, LPA was shown to activate multiple growth and survival pathways, including ERK1/2, Akt, paxillin, Shc, and SHP-2. Transactivation of the receptor-tyrosine kinase, EGFR, was also observed.

Part I: Growth/Survival Effects of LPA in HCT-8 Cells:

The ability of LPA to act as a growth factor, and a survival factor for cells in culture, is well characterized in the literature and is the subject of numerous reviews (For review See Mills and Moolenaar (2003) Nat. Rev. Cancer 3:582-91). Due to the acknowledged presence of three other specific LPA receptors (LPA1-3) and the demonstrated ability of these receptors to transduce some of these growth/survival effects of LPA on cells, it was of interest to determine OSGPR114 may also possess similar biological effects. HCT-8 cells were chosen for this experiment as they have one of the highest expression levels of OSGPR114 within the cell lines expression profiled. Additionally, OSGPR114 is the predominant receptor, although Edg4 is also expressed in these cells at much lower levels The effect of LPA on cell proliferation (Cell TiterGlo assay, Promega) and induction of apoptosis (Apo-One Caspase 3/7 assay, Promega) was measured in the presence and absence of serum. Cell-titer Glo is an assay that quantitates ATP as a measurement of the number of viable cells in a culture. The assay utilizes a luciferase-based luminescent signal. The Apo-One assay utilizes a profluorescent caspase 3/7 consensus substrate to measure the activation of caspase in the sample. The experiments were conducted in serum-free media as it is known that serum contains high concentrations of LPA (of the order of 10-30 uM). Briefly, cells were plated in 96-well plates at a density of 20,000 cells/well. After 24 h the serum-containing media was removed from the cells and replaced with either serum-containing or serum-free media. After 24 h LPA, at concentrations from 1-100 μM was added to the cells. 24 h later the induction of apoptosis and the level of cellular proliferation was measured using the Cell titer-glo or Caspase 3/7 Apo-One assay kits commercially available from Promega. The data are shown in FIG. 1.

LPA acting on HCT-8 cells induced growth of the cells in a concentration dependent manner in serum free conditions, and reversed apoptosis induced through the serum starving of the cells. Due to the high concentration of LPA in serum, no statistically significant effects of LPA were observed in the presence of 10% FCS.

Part II: Effects of OSGPR114 and OSGPR78 siRNAs on Cell Growth and Survival:

The sequence-specific gene silencing induced by double stranded RNA is known as RNA interference (RNAi). It is a powerful technique with which the function of a specific gene can be investigated through its silencing by small interfering RNAs (siRNA). Because of the sequence specificity of the siRNA, only the gene of interest should be effectively silenced. It is a particularly powerful technique for assessing knockdown/inhibition of a gene's function in the absence of a pharmacological inhibitor of the gene (For review see Devereaux et al. (2003) Seminars Cancer Biol. 13:293-300). In order to assess the role of the novel LPA receptors OSGPR114 and OSGPR78, siRNA oligonucleotides (Smart-Pool) specific to either OSGPR114 or OSGPR78 were provided by Dharmacon Inc. Non-specific control oligonucleotides were used as negative controls and siRNA targeting polo-like kinase 1 (PLK1) was used as a positive control as siRNA targeting of this gene has been shown in the literature to induce apoptosis and inhibit cell growth.

With conditions and reagents that were optimized for each cell line tested, the siRNAs (50-75 nM) were introduced into cells known to express a particular receptor of interest. Such optimization included varying the Transfection reagent, the oligonucleotide concentration, the lipid:oligonucleotide ratio, the optimal transfection cell density and the time for optimal gene knockdown. Every cell line displayed its own unique optimal transfection condition profile.

The effects of this transfection upon cell proliferation were measured using a fluorometric 5-bromo-2-deoxyuridine (BrDU) assay (Roche) or a Cell-titer Glo assay (Promega) and the effects upon apoptosis by measuring caspase 3/7 cleavage using the Apo-One caspase kit (Promega). Manufacturers instructions were followed with each kit and either 48 h or 72 h post-transfection endpoints were tested.

The cell lines chosen were picked upon the basis of a demonstration of the expression of the receptor of interest as measured by quantitative RT-PCR. RT-PCR was conducted as previously described. Table 1 shows the relative expression of OSGPR78 or OSGPR114 in cell lines used for the siRNA experiments.

| Cell Line | Origin | OSGPR114 Expression | OSGPR78 expression |
| --- | --- | --- | --- |
| HCT-8 | Colon Cancer | 0.15* | 0.0016* |
| KLE | Endometrial cancer | 1.48E−03 | 4.80E−04 |
| HCT-116 | Colon cancer | 3.60E−04 | 2.30E−05 |
| A2058 | Melanoma | 0* | 0.641* |
| H460 | Lung cancer | 1.90E−07 | 3.50E−05 |
| MDAH-2774 | Ovarian cancer | 4.30E−04 | 1.07E−03 |

Data expressed relative to GAPDH expression except where denoted by * (Data expressed relative to TFIIB)

Table 1. Expression of OSGPR78 and OSGPR114 in cells used for siRNA experiments (N.B. E denotes exponent often; e.g. 1.48E-03=1.48×10$^{-3}$)

FIGS. 2-7 show a summary of the siRNA experiments conducted with OSGPR114 and OSGPR78 specific siRNAs, and the effects of the transfection of these oligonucleotides on cell proliferation and survival in cell lines of interest. All data are expressed as a fraction of (for BrDU/Cell titer glo assays) or fold induction over (for caspase assays) untreated cells. Negative controls (non-specific siRNA) and positive controls (polo-like kinase 1 (PLK1) siRNA) are also shown. PLK1 was used as a positive control as PLK1 siRNA has been demonstrated in the literature to induce apoptosis and inhibit cell growth (Spankuch-Schmitt et al. (2002) J. Nat. Cancer Inst. 94:1863-1877). The transfection reagent, concentration of siRNA oligonucleotide, original cell plating density and the n number are shown in the headers for each graph. A single n number was a single experiment conducted in triplicate and the data averaged. The timepoint used for data generation (either 48 or 72 h post-siRNA transfection is also shown in individual graph titles. Statistical significance is defined as *p<0.05 and ***p<0.001 (One way ANOVA, Dunnett's post-hoc).

Table 2 demonstrates a summary of the effects of OSGPR114 and OSGPR78 siRNAs on growth and proliferation in each of the cell lines tested in this study. An indication of yes illustrates a statistically significant inhibition of cell proliferation or a statistically significant induction of apoptosis.

| Cancer Cell Line | OSGPR114 | | OSGPR78 | |
| --- | --- | --- | --- | --- |
| | Proliferation | Apoptosis | Proliferation | Apoptosis |
| HCT-8 (colon) | Yes | Yes | Not tested | |
| KLE (endometrial) | Yes | No | No | No |
| A2058 (melanoma) | Not tested | | Yes | Yes |
| HCT116 (colon) | Yes | Yes | No | No |
| H460 (lung) | Yes | Yes | Yes | Yes |
| MDAH-2774 (ovarian) (n = 1) | Yes | No | Yes | No |

Table 2: Comparison of data from FIGS. 2-7 showing a summary of the effects on proliferation and apoptosis of OSGPR114 and OSGPR78 siRNA transfection in 6 cell lines.

Summary of siRNA Experiments:

In summary, introduction of siRNAs specific to OSGPR114 induced growth inhibition in five out of five cell lines tested, and induced apoptosis in three of the five cell lines strongly suggesting that this receptor is involved in promoting growth and survival of all cancer cell lines tested. Considering that every cancer cell line tested, derived from a multitude of original tumors, were sensitive to the growth inhibitory effects of OSGPR114 knockdown, it is likely that additional cell lines, from multiple other cancer types will respond similarly. Additionally, the introduction of siRNAs specific to OSGPR78 also inhibited the growth and induced apoptosis in the cell lines in which it was tested, also implicating this receptor as a mediator of growth and survival of certain cancer cells in culture. Again, and similar to the previously stated hypothesis, it is likely that the proliferation of multiple other cancer cell lines, and tumor types, will be sensitive to genetic knockdown of OSGPR78, and that the sensitivity will only be dictated by the expression of the receptor in a particular cancer cell. Furthermore, these data demonstrate that pharmacological inhibitors of the receptors (acting by causing, for example, reduced receptor expression level, reduced receptor activity level, or decreased receptor-stimulated signal transduction activity) will also cause growth inhibition and induce apoptosis in cells that express these receptors. This would allow the use of pharmacological inhibitors of these receptors in disease states where an inhibition of cellular growth and/or an induction of cellular apoptosis would be beneficial, for example for the treatment of cancers.

Figure 9:
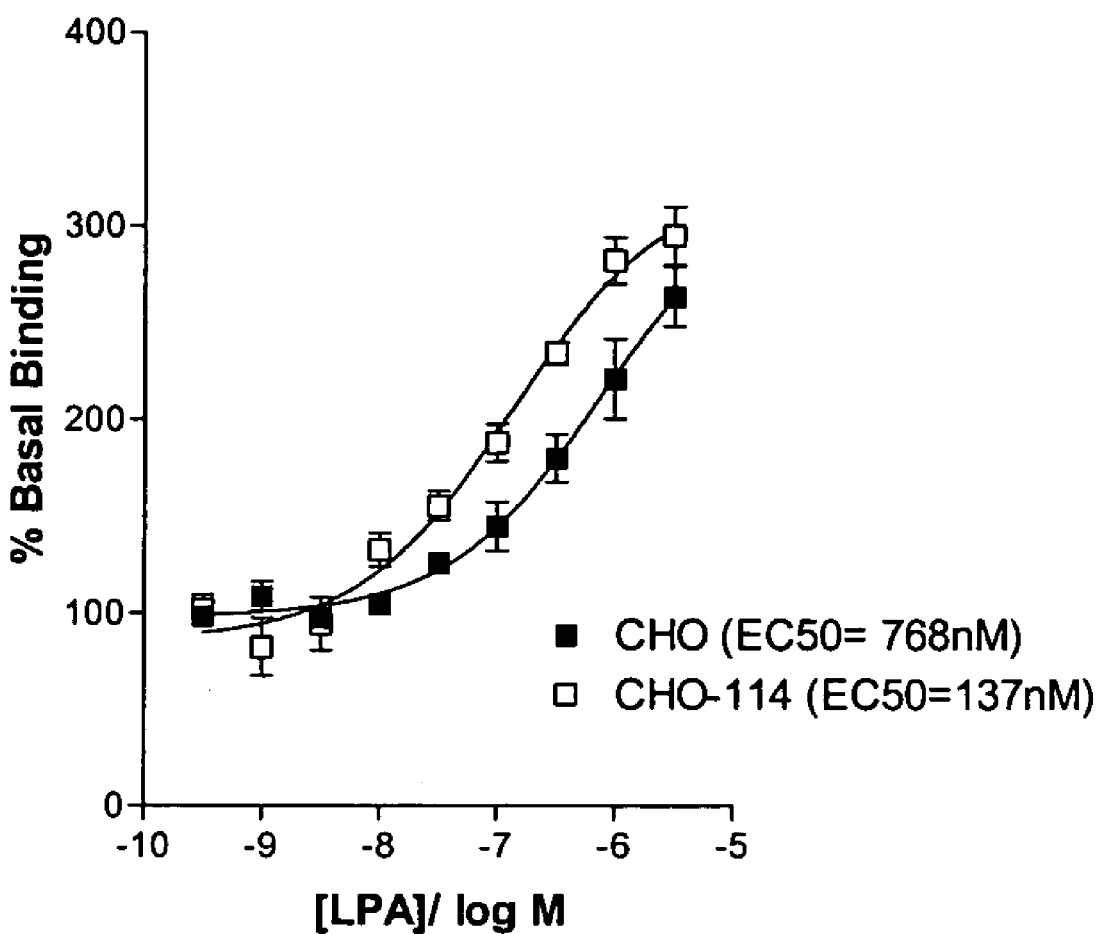
FIG. 9: Stimulation of GTPγS binding in cell membranes prepared from OSGPR114-CHO and CHO-K1 cells. The experiment was conducted as described in the Materials and Methods section.

Part III: LPA Signaling Pathways in HCT-8 Cells:

Introduction:

Many of the genes and signaling pathways that are implicated in oncogenic transformation and tumor growth and survival are known. These have been increasingly well characterized in the public literature over the last 2-3 decades. It was therefore of interest to determine what role OSGPR114 may play in regulating these signaling pathways. In order to determine the roles of the receptor, the effect of LPA on these pathways in cells known to express OSGPR114 was tested. In defining the cancer cell line to use for these studies multiple cancer cell lines were expression profiled not only for OSGPR114 expression but also the expression of other LPA receptors. LPA is known to be a critical growth and survival factor for virtually every cancer cell in culture not least because almost all cells express a multiplicity of LPA receptors. For experiments investigating the signaling pathways of OSGPR114 it was therefore important to use a cancer cell which expressed OSGPR114 at the highest relative levels to other LPA receptors. HCT-8 colon cancer cells were judged to be the best model available for these experiments and a graphical representation of the expression profile of all LPA receptors in these cells is shown in FIG. 9. They were judged to be the best model based on the very high level of OSGPR114 mRNA expressed by these cells, in addition to the lower relative levels of other known LPA receptors in these cells.

ERK Activation:

One of the principal proliferative signaling pathways is the activation of ERK. Multiple growth factor receptors have been shown to induce cellular proliferation as a result of activation of this pathway. LPA has been demonstrated in many cell lines, and acting at different LPA receptors, to activate ERK. However, the ability of LPA acting at OSGPR114 to effect ERK is unknown. HCT-8 cells, which express OSGPR114 at high levels, provide one of the best models available. LPA was found to stimulate ERK in HCT-8 (and ASPC-1, another cell line shown to express OSGPR114) cells. This evidence supporting the hypothesis that LPA, likely acting at least in part at OSGPR114, induces ERK activation, a signaling pathway that is known to stimulate cellular proliferation.

EGFR Transactivation:

The ability of LPA to phosphorylate ERK1/2 has been extensively described in the literature, and three principal mechanisms have been described for this effect. Firstly, LPA receptors have been shown to stimulate ERK via a Gα12/13-Rho based pathway. Additionally, this activation of ERK has been shown to be dependent on two different receptor tyrosine kinase (RTK) transactivation pathways. The first of these pathways involves β-arrestin recruitment and activation of Src, which then transactivates the RTK. The second of these pathways involves Shc which is recruited by LPA and can itself activate membrane-bound metalloproteases (e.g. ADAM10) which causes release of heparin-bound epidermal growth factor (EGF) which can then activate EGF receptor.

EGF and activation of the EGF receptor is a well known proliferative pathway for many cell lines. The possibility of LPA causing transactivation of EGFR in HCT-8 cells was tested as the EGFR signaling pathway is known to be present and active in these cells. From FIG. 11, it is clear that LPA, at a concentration of 10 µM is capable of transactivating EGFR in HCT-8 cells. From the LPA-based literature, the potential for LPA to also transactivate other RTKs, such as PDGFR for example, in these cells is a very likely possibility.

Additional Signaling Pathways Utilized by LPA in HCT-8 Cells:

Many of the growth and survival signaling pathways of cancer cells have been identified. In addition to the stimulation of the mitogen-activated protein kinase pathway demonstrated by the activation of ERK1/2 by LPA, and the transactivation of other known cancer cell growth factor receptors such as EGFR, the effect of LPA on additional known growth and survival signaling was investigated. The protein Shc is an adaptor protein and the protein phosphatase SHP-2 are known to link the activation of multiple growth factor receptors to their downstream signaling pathways in cancer cells (For review see Yart et al. (2003) Current Cancer Drug Targets 3:177-192). These proteins are involved in mitogenic signaling by linking growth stimuli to the Ras-mitogen-activated protein kinase cascade and the PI3K survival pathway. LPA, at a concentration of 10 uM when added to HCT-8 cells, induced the phosphorylation of Shc and SHP-2, further demonstrating the role of LPA receptors in HCT-8 cells acting as growth and survival factors. Additionally, paxillin is a scaffold molecule intricately involved in the regulation of focal adhesions in cancer cells. It is therefore involved in the regulation of cell spreading and motility and is controlled by a multitude of signaling moieties including growth factors, and their downstream signaling molecules. Paxillin recruits these signaling components into specific cell compartments known as focal adhesions (For review, see Schaller (2001) Oncogene 20:6459-72). LPA, acting at other LPA receptors, has been shown in the literature to increase cellular motility as well as increasing cellular growth and survival. By treating HCT-8 cells with LPA (10 uM), the effect of LPA on the phosphorylation of paxillin was measured using activation state specific antibodies (FIG. 12). It was found that LPA caused a highly significant increase in phosphorylated paxillin, further supporting its role not only as a growth and survival factor but also as a regulator of cancer cell motility.

LPA and Akt:

The protein Akt is a well characterized survival pathway for many cancer cells and is a pathway that can be induced by multiple cell growth factors (For review, see Marte and Downward (1997) Trends Biochem. Sci. 22:355-358). FIG. 13 demonstrates the ability of LPA, at a concentration of 10 uM to stimulate phosphorylation of Akt, as detected by a phospho-specific Akt antibody. The cells used for this experiment were a CHO cell line stably transfected with OSGPR114. The cells were treated with vehicle, LPA (10 uM) or EGF (1 uM) for 3 minutes. This experiment demonstrates the ability of LPA, in cells stably over-expressing OSGPR114, to activate this well known survival pathway in cells.

SUMMARY

LPA has been shown to cause the proliferation of HCT-8 cells in serum-free conditions and to prevent apoptosis induced by serum starving. Additionally, siRNA has shown that biochemical inhibition of OSGPR114 and OSGPR78 both inhibits cancer cell proliferation and induces apoptosis. Finally LPA has been shown to stimulate multiple signaling pathways implicated in the growth, survival and motility of cancer cells including ERK1/2, EGFR, Akt, Shc, SHP-2 and paxillin. The activity of LPA in HCT-8 cells, a colon cancer cell line known to highly express OSGPR114, in inducing all of these pathways lends further support to the hypothesis demonstrated with the siRNA and growth measurement experiments that LPA is an important growth and survival factor for cancer cells in vitro, and demonstrates that a pharmacological inhibitor of LPA signaling at OSGPR114 will be beneficial in the treatment of cancer and other proliferative diseases.

INCORPORATION BY REFERENCE

All patents, published patent applications and other references disclosed herein are hereby expressly incorporated herein by reference.

EQUIVALENTS

Those skilled in the art will recognize, or be able to ascertain, using no more than routine experimentation, many equivalents to specific embodiments of the invention described specifically herein. Such equivalents are intended to be encompassed in the scope of the following claims.

What is claimed is:

1. An assay process for identifying a compound that specifically binds to an OSGPR114 receptor, wherein said OSGPR114 receptor comprises an amino acid sequence having at least 95% identity to SEQ ID NO:3, that can induce oleoyl lysophosphatidic acid stimulation of G-protein activity in cells, said process comprising:
   providing either
      (a) two samples of cells expressing on their cell surface the OSGPR114 receptor, or
      (b) two samples of a membrane preparation from said cells;
   contacting one sample with a lysophosphatidic acid ligand known to bind to the receptor, under conditions suitable for binding of said ligand to the receptor, in the presence of a test compound;
   contacting the second sample with said ligand, under conditions suitable for binding of said ligand to the receptor, in the absence of the test compound;
   measuring the specific binding of the ligand to the receptor in the presence of the compound;
   measuring the specific binding of the ligand to the receptor in the absence of the compound; and
   comparing the binding in the presence and in the absence of the compound being tested, wherein a difference in comparison indicates that the compound binds to the OSGPR114 receptor.

2. The process of claim 1, wherein the lysophosphatidic acid has a fatty acid group with a carbon chain length selected from C14, C15, C16, C17, C18, C19, C20, C21 and C22.

3. The process of claim 1, wherein the lysophosphatidic acid is selected from myristoyl lysophosphatidic acid, oleoyl lysophosphatidic acid, palmitoyl lysophosphatidic acid, and stearoyl lysophosphatidic acid.

4. The process of claim 1, wherein the lysophosphatidic acid is selected from 1-myristoyl lysophosphatidic acid, 1-oleoyl lysophosphatidic acid, 1-palmitoyl lysophosphatidic acid, and 1-stearoyl lysophosphatidic acid.

5. The process of claim 1, wherein the lysophosphatidic acid has an alkyl ether or alkenyl ether group.

6. The process of claim 5, wherein the alkyl ether or alkenyl ether group has a carbon chain length selected from C14, C15, C16, C17, C18, C19, C20, C21 and C22.

7. The process of claim 1, wherein the cells are insect cells, mammalian cells, human cells, or yeast cells.

8. The process of claim 1, wherein the cells are NIH-3T3, mouse Y1, CHO, RH7777, Jurkat, HCT4, RBL243, HeLa, ASPC-1, HEK-293, or COS7 cells.

9. The process of claim 1, wherein the OSGPR114 receptor comprises an amino acid sequence having SEQ ID NO:3, that can induce oleoyl lysophosphatidic acid stimulation of G-protein activity in cells.

10. A method of screening a plurality of compounds not known to bind to an OSGPR114 receptor, wherein said OSGPR114 receptor comprises an amino acid sequence having at least 95% identity to SEQ ID NO:3, that can induce oleoyl lysophosphatidic acid stimulation of G-protein activity in cells, to identify a compound which specifically binds to the OSGPR114 receptor, said process comprising:
   providing either
      (a) two samples of cells expressing on their cell surface the OSGPR114 receptor, or
      (b) two samples of a membrane preparation from said cells;
   contacting one sample with a lysophosphatidic acid ligand known to bind to the receptor, under conditions suitable for binding of said ligand to the receptor, in the presence of the plurality of compounds not known to bind to the receptor;
   contacting the second sample with said ligand, under conditions suitable for binding of said ligand to the receptor, in the absence of the plurality of compounds;
   measuring specific binding of the ligand to the receptor in the presence of the plurality of compounds;
   measuring specific binding of the ligand to the receptor in the absence of the plurality of compounds;
   comparing the binding in the presence and in the absence of the plurality of compounds, wherein a difference in the compared binding results indicates that one or more compounds in the plurality of compounds binds to the OSGPR114 receptor; and
   determining, when a difference in the compared binding is found, the binding to the OSGPR114 receptor of each compound included in the plurality of compounds, to identify any compound included therein which specifically binds to the OSGPR114 receptor.

11. The method of claim 10, wherein the lysophosphatidic acid has a fatty acid group with a carbon chain length selected from C14, C15, C16, C17, C18, C19, C20, C21 and C22.

12. The method of claim 10, wherein the lysophosphatidic acid is selected from myristoyl lysophosphatidic acid, oleoyl lysophosphatidic acid, palmitoyl lysophosphatidic acid, and stearoyl lysophosphatidic acid.

13. The method of claim 10, wherein the lysophosphatidic acid is selected from 1-myristoyl lysophosphatidic acid, 1-oleoyl lysophosphatidic acid, 1-palmitoyl lysophosphatidic acid, and 1-stearoyl lysophosphatidic acid.

14. The method of claim 10, wherein the lysophosphatidic acid has an alkyl ether or alkenyl ether group.

15. The method of claim 14, wherein the alkyl ether or alkenyl ether group has a carbon chain length selected from C14, C15, C16, C17, C18, C19, C20, C21 and C22.

16. A method of claim 10, wherein the cells are mammalian cells, human cells, or yeast cells.

17. The method of claim 10, wherein the cells are NIH-3T3, mouse Y1, CHO, RH7777, Jurkat, HCT4, RBL243, HeLa, ASPC-1, HEK-293, or COS7 cells.

18. The method of claim 10, wherein the OSGPR114 receptor comprises an amino acid sequence having SEQ ID NO:3, that can induce oleoyl lysophosphatidic acid stimulation of G-protein activity in cells.

19. A process for determining whether a chemical compound specifically binds to and modulates activation of an OSGPR114 receptor, wherein said OSGPR114 receptor comprises an amino acid sequence having at least 95% identity to SEQ ID NO:3, that can induce oleoyl lysophosphatidic acid stimulation of G-protein activity in cells, said process comprising:
   providing two samples of cells expressing on their cell surface the OSGPR114 receptor, wherein activation of the receptor produces a second messenger response;
   contacting one sample, in the presence of a test compound, with a second compound known to activate the receptor, under conditions suitable for activation of the receptor;
   contacting the second sample, in the absence of the test compound, with the second compound known to activate the receptor, under conditions suitable for activation of the receptor;
   measuring the second messenger response in the presence of the test compound,
   measuring the second messenger response in the absence of the test compound; and comparing the second messenger response in the presence and in the absence of the compound being tested, wherein a difference in the second messenger response from the OSGPR114 receptor indicates that the compound modulates activation of a OSGPR114 receptor.

20. The process of claim 19, wherein the second compound is a lysophosphatidic acid.

21. The process of claim 20, wherein the lysophosphatidic acid has a fatty acid group with a carbon chain length selected from C14, C15, C16, C17, C18, C19, C20, C21 and C22.

22. The process of claim 20, wherein the lysophosphatidic acid is selected from myristoyl lysophosphatidic acid, oleoyl lysophosphatidic acid, palmitoyl lysophosphatidic acid, and stearoyl lysophosphatidic acid.

23. The process of claim 20, wherein the lysophosphatidic acid is selected from 1-myristoyl lysophosphatidic acid, 1-oleoyl lysophosphatidic acid, 1-palmitoyl lysophosphatidic acid, and 1-stearoyl lysophosphatidic acid.

24. The process of claim 20, wherein the lysophosphatidic acid has an alkyl ether or alkenyl ether group.

25. The process of claim 24, wherein the alkyl ether or alkenyl ether group has a carbon chain length selected from C14, C15, C16, C17, C18, C19, C20, C21 and C22.

26. The process of claim 19, wherein the second messenger response comprises chloride channel activation, a change in intracellular calcium ion levels, a release of inositol phosphate, a release of arachidonic acid, GTPγS binding, activation of MAP kinase, cAMP accumulation, a change in intracellular potassium ion levels, or a change in intracellular sodium ion levels.

27. The process of claim 26, wherein the second messenger response is measured by a change in reporter gene activity.

28. The process of claim 27, wherein the reporter gene is selected from secreted alkaline phosphatase, luciferase, and β-galactosidase.

29. The process of claim 19, wherein the OSGPR114 receptor comprises an amino acid sequence having SEQ ID NO:3, that can induce oleoyl lysophosphatidic acid stimulation of G-protein activity in cells.

30. A method of preparing a composition comprising a compound which specifically binds to an OSGPR114 receptor, wherein said OSGPR114 receptor comprises an amino acid sequence having at least 95% identity to SEQ ID NO:3, that can induce oleoyl lysophosphatidic acid stimulation of G-protein activity in cells, by a process comprising:
providing either
(a) two samples of cells expressing on their cell surface the OSGPR114 receptor, or
(b) two samples of a membrane preparation from said cells;
contacting one sample with a lysophosphatidic acid ligand known to bind to the receptor, under conditions suitable for binding of said ligand to the receptor, in the presence of a test compound;
contacting the second sample with said ligand, under conditions suitable for binding of said ligand to the receptor, in the absence of the test compound;
measuring specific binding of the ligand to the receptor in the presence of the compound;
measuring specific binding of the ligand to the receptor in the absence of the compound; and
comparing the binding in the presence and in the absence of the compound being tested, wherein a difference in the binding of the ligand to the OSGPR114 receptor indicates that the compound binds to the OSGPR114 receptor; and
admixing the compound so identified, or a functional analog or homolog of said compound, with a carrier, thereby preparing said composition.

31. The method of claim 30, wherein the lysophosphatidic acid has a fatty acid group with a carbon chain length selected from C14, C15, C16, C17, C18, C19, C20, C21 and C22.

32. The method of claim 30, wherein the lysophosphatidic acid is selected from myristoyl lysophosphatidic acid, oleoyl lysophosphatidic acid, palmitoyl lysophosphatidic acid, and stearoyl lysophosphatidic acid.

33. The method of claim 30, wherein the lysophosphatidic acid is selected from 1-myristoyl lysophosphatidic acid, 1-oleoyl lysophosphatidic acid, 1-palmitoyl lysophosphatidic acid, and 1-stearoyl lysophosphatidic acid.

34. The method of claim 30, wherein the lysophosphatidic acid has an alkyl ether or alkenyl ether group.

35. The method of claim 34 wherein the alkyl ether or alkenyl ether group has a carbon chain length selected from C14, C15, C16, C17, C18, C19, C20, C21 and C22.

36. The method of claim 30, wherein the OSGPR114 receptor comprises an amino acid sequence having SEQ ID NO:3, that can induce oleoyl lysophosphatidic acid stimulation of G-protein activity in cells.

* * * * *